(12) United States Patent
Chung et al.

(10) Patent No.: US 9,216,148 B2
(45) Date of Patent: Dec. 22, 2015

(54) COMPOUND HAVING SKIN-WHITENING, ANTI-OXIDIZING AND PPAR ACTIVITIES AND MEDICAL USE THEREFOR

(75) Inventors: Hae Young Chung, Busan (KR); Hyung Ryong Moon, Busan (KR); Min Hi Park, Busan (KR); Young Mi Ha, Busan (KR); Yun Jung Park, Busan (KR); Ji Young Park, Busan (KR); Jin Ah Kim, Busan (KR); Ji Yeon Lee, Gyeongsangnam-do (KR); Kyung Jin Lee, Busan (KR)

(73) Assignee: Pusan National University Industry-University Cooperation Foundation, Busan (KR)

( * ) Notice: Subject to any disclaimer, the term of this patent is extended or adjusted under 35 U.S.C. 154(b) by 34 days.

(21) Appl. No.: 13/984,573

(22) PCT Filed: Feb. 8, 2012

(86) PCT No.: PCT/KR2012/000899
§ 371 (c)(1),
(2), (4) Date: Oct. 8, 2013

(87) PCT Pub. No.: WO2012/108677
PCT Pub. Date: Aug. 16, 2012

(65) Prior Publication Data
US 2014/0023603 A1 Jan. 23, 2014

(30) Foreign Application Priority Data
Feb. 9, 2011 (KR) .................. 10-2011-0011543

(51) Int. Cl.
*A61K 8/49* (2006.01)
*A61Q 19/02* (2006.01)
(Continued)

(52) U.S. Cl.
CPC . *A61K 8/49* (2013.01); *A61Q 19/02* (2013.01); *A61Q 19/08* (2013.01); *C07D 277/34* (2013.01)

(58) Field of Classification Search
None
See application file for complete search history.

(56) References Cited

U.S. PATENT DOCUMENTS

2003/0073712 A1* 4/2003 Wang et al. .................. 514/277

FOREIGN PATENT DOCUMENTS

| WO | WO 91/17151 A1 | 11/1991 |
| WO | WO 02/056858 A1 | 7/2002 |
| WO | WO 03/074497 A1 | 9/2003 |

(Continued)

OTHER PUBLICATIONS international Search Report for PCT/KR2012/000899 mailed Sep. 5, 2012 from Korean Intellectual Property Office.
PubChemCompound, datasheet [online compond summary] Retrieved from the Internet: <URL: http://pubchem.ncbi.nlm.nih.gov/search/search.cgi>, Aug. 17, 2012.

(Continued)

*Primary Examiner* — Ernst V Arnold
*Assistant Examiner* — Kyung Sook Chang
(74) *Attorney, Agent, or Firm* — Paratus Law Group, PLLC

(57) ABSTRACT

Provided are a novel compound having skin-whitening, anti-oxidizing and PPAR activities and a medical use thereof, and the compound has skin-whitening activities for the suppression of tyrosinase, and accordingly, is useful for use in skin-whitening pharmaceutical composition or cosmetic products; has anti-oxidant activities, and accordingly, is useful for the prevention and treatment of skin-aging; and has PPAR activities, and in particular, PPARα and PPARγ activities, and accordingly, is useful for use in pharmaceutical compositions or health foods which are effective for the prevention and treatment of obesity, metabolic disease, or cardiovascular disease.

1 Claim, 5 Drawing Sheets

(51) Int. Cl.
*A61Q 19/08* (2006.01)
*C07D 277/34* (2006.01)

(56) References Cited

FOREIGN PATENT DOCUMENTS

| WO | WO 2005/119252 A2 | 12/2005 |
| WO | WO 2007/101213 A2 | 9/2007 |

OTHER PUBLICATIONS

Yoshiaki Isobe et al., "Synthesis of pyrimidine derivatives possessing an antioxidative . . . ", Chemical Pharmaceutical Bulletin, 2003, vol. 51, No. 12, pp. 1452-1454.

Xiaofeng Liu et al., "Discovery and SAR of Thiazolidine-2,4-dione Analogues as . . . ", Journal of Medicinal Chemistry, 2010, pp. 2661-2665.

* cited by examiner

COMPOUND HAVING SKIN-WHITENING, ANTI-OXIDIZING AND PPAR ACTIVITIES AND MEDICAL USE THEREFOR

CROSS REFERENCE TO PRIOR APPLICATION

This application is a National Stage Patent Application of PCT International Patent Application No. PCT/KR2012/000899 (filed on Feb. 8, 2012) under 35 U.S.C. §371, which claims priority to Korean Patent Application No. 10-2011-0011543 (filed on Feb. 9, 2011), which are all hereby incorporated by reference in their entirety.

TECHNICAL FIELD

The present invention relates to a novel compound having skin-whitening, anti-oxidizing and PPAR activities and a medical use thereof.

BACKGROUND ART

Human skin color is determined according to amounts of melanin, carotene, and hemoglobin, and from among them, melanin acts as the most determining factor. Melanin pigment is a phenol-based polymer material that has a composite form of black pigment and protein, and blocks ultraviolet light, and people who lacks melanin pigment is very sensitive to sun light and is highly likely to have burns, and even at young ages, the possibility of skin cancer is high. Generally, short-wave ultraviolet light and carcinogen form a free radical that is harmful for skin. Melanin removes the free radical to protect proteins and genes. Accordingly, the wording that melanin is present in great quintiles means that an effective response system for the protection of skin from physical or chemical toxicity materials is provided.

Melanin has a circulating cycle: melanin is generated from tyrosine due to an action of tyrosinase in pigment cells through complicated processes, the generated melanin is transferred to skin cells and consumed and removed when excoriation occurs. This melanin generation process naturally occurs, and in a normal-state skin, excess melanin is not generated. However, when skin responses to external stimuli, for example, ultraviolet light, environmental pollution, or stress, excess melanin is generated so that melanin is not discharged into outside the skin but is transferred to keratinocyte to accumulate in a skin epidermis, thereby causing serious cosmetic problems, such as melasma, freckle, and senile lentigo, promoting skin aging, and inducing skin cancer.

Meanwhile, research into the prevention of melanin pigmentation in skin has been performed in four aspects. First, a tyrosinase synthesis inhibiting material or an antagonist against a matrix of tyrosinase is developed to control the activity of tyrosinase, which is an apoenzyme for melanin synthesis. Second, a material that has toxicity to melanocyte, in which melanin biosynthesis occurs in animals, is developed to decrease the function of melanocyte. Third, a material that reduces dopa, which is an intermediate metabolic material of a melanin synthesis path, is developed to prevent the oxidation of dopa. Finally, an activity of a first enzyme tyrosinase, which is a melanin generator, an activity of a second enzyme DOPA chrome tautomerase that promotes conversion from DOPA chrome to 5,6-dihydroxyindole-2-carboxylc acid (DHICA), and an activity of a third enzyme that promotes conversion from DHICA to indole-5,6-quinone-2-carboxylic acid are simultaneously reduced.

Recently, women in the Asia region desire to have skin that is as white and clean as white porcelain, and regard the whiteness and cleanness as critical criteria for the evaluation of beauty. Accordingly, the development of whitening agents for the treatment of abnormal skin pigmentation and the satisfaction of cosmetic desires is actively being performed.

As a known method of developing a whitening agent, there are a decoloration method performed by reducing a generated melanin pigment and a method of suppressing activities of tyrosinase, which is an enzyme for forming melanin pigment. However, a whitening agent prepared by using tocopherol or vitamins to reduce melanin pigment is known to have very small decoloration effects. Accordingly, an inhibitor that suppresses the generation of melanin pigment by inhibiting activities of tyrosinase is getting attention.

In conventional cosmetic fields, as a whitening material, for example, a material for suppressing activities of tyrosinase enzyme, such as kojic acid or arbutin, hydroquinone, vitamin C (L-Ascorbic acid) and a derivative thereof, and various plant extracts are used. However, use of these materials is limited due to their low stability in a prescription system, leading to decomposition and pigmentation, generation of offensive odor, uncertainty and stability of efficacy and effectiveness at bio-levels. Also, although kojic acid allows a copper ion present in an active site of tyrosinase to adsorb to inhibit enzymatic activities, when mixed in cosmetic products, instability, skin adverse effects, and liver cancer, which was recently identified based on animal tests, may occur, and accordingly, use of the kojic acid in cosmetic products was stopped. Vitamin C and a derivative thereof are highly likely oxidized, and due to this instability, it is difficult for these materials to be used in cosmetic source materials. Hydroquinone has excellent skin whitening effects. However, it has high skin irritation because hydroquinone causes allergy, has toxicity to melanin forming cells, and induces permanent decoloration of skin. Also, in many countries, hydroquinone is defined as carcinogen, and thus, only limited concentration of thereof is allowed for use. Arbutin is a derivative in which gucopyranoside binds to hydroquinone, and has smaller adverse effects than when hydroquinone is used, and suppresses synthesis of a melanin pigment without toxicity to human body. Due to such characteristics, its use for the treatment of skin disorders, in which melanin pigmentation more occurs, has been suggested. However, arbutin partly decomposes by skin enzyme. Accordingly, there is a need to develop an alternative whitening agent that has high efficiency even at small concentrations, smaller adverse effects, and stability.

Also, reactive oxygen species (ROS) refers to an in vivo toxic material associated with oxygen, and examples of ROS are a free radical, such as superoxide, hydroxyl, peroxyl, alkoxyl, or hydroperoxyl, and a non-free radical, such as hydrogen peroxide, hypochlorous acid, ozone, singlet oxygen, or peroxynitrite.

From among these ROS, regarding oxygen toxicity, a superoxide free radical (reactive oxygen or harmful oxygen) is the most frequently researched thereinto and plays a critical role (Fridorich L., Science, 201, pp 175-180, 1978). A free radical, which is a strong oxidizing gent, is an unpaired electron. A free radical is generated during oxidation and reduction reactions of various organisms, and may cause deterioration of eatable oil, or may oxidatively damage on various biomaterials (lipid, protein, nucleic acid, carbohydrate) and through various steps, ultimately, mutants may occur (Yen G C et al., J. Agric. Food Chem., 43, pp 27-32, 1995). Regarding an unsaturated fatty acid of phosphatide which constitutes a biological membrane, a free radical, such as reactive oxygen species, initiates a peroxidative reaction and also the reaction is proceeds consecutively. Accordingly, a peroxidative reaction due to the free radical may increase permeability of a cell membrane and cause overall cytotoxicity, thereby inducing aging or pathological phenomenon of aging-associated disorders to be engaged in cancer generation process. The action of a radical heavily affects progress of various chronic disease, such as atopic disease, cancer, hypertension, myocardial infarction, arteriosclerosis, rheumatis, cataract, Parkinson's disease, which are disorders associated with oxidative stress (DeSouza L C et al., Bioorg. Med. Chem. Lett., 14, pp 5859-5861, 2004), and may weaken the function of an immune system (Pike J et al., Int. J. Vitam. Nutr. Res., 65, pp 117-120, 1995).

Accordingly, anti-oxidation evaluation on an alternative material for the prevention from the oxidative damage is very actively performed. Antioxidants do not remove or absorb oxygen, but react with a free radical so that loss of particular vitamins and necessary amino acids is minimized, and corruption of oil product is delayed or prevented. As a synthesis antioxidant used in foods and medical products, butylated hydroxyanisole (BHA), butylated hydroxytoluene (BHT), propyl galate (PG), and tertiary-butyl hydroquinone (TBHQ) may be used. However, when these antioxidants are administered at high concentrations into test animals, hepatomegaly or cancer may progress. In particular, butylated hydroxytoluene is known to, based on various study results, increase enzymatic activity (microsomal enzyme activity in the liver of lab animals), and thus, stability of these phenol-based synthesis antioxidants is debated, and currently, available amounts thereof are legally limited (Brannen A L, J. Amer. Oil Chem. Soc., 52, pp 59-63, 1975; Ito N et al., J. Natl. Cancer Inst., 70, p 343, 1983; Chan K M et al., J. Food. Sci., 58, pp 1-4, 1993). In response, much research into vegetable-originated natural antioxidants that have high antioxidant effects, are stable, and are prepared at low costs is being performed (Larson R A, Phytochemistry, 27, pp 969-978, 1988). Alongside the recent research into natural materials, secondary metabolite that is included in natural materials is getting attention as a bioactive material, and in particular, research into antioxidants is actively being performed, and examples of known natural antioxidants are tocopherols, flavonoids, gossypols, sesamols, oryzanol, and vitamin C (Huson B et al., Food Chem., 19, pp 537-541, 1987; Frankel, E. N. Food Chem., 57, p 51, 1996; Giese J, Food Technol., 5, pp 73-81, 1996; Pszcczola D E, Food Tech., 55, pp 51-59, 2001). In particular, tocopherol and L-ascorbic acid are preferred as a natural antioxidant, and despite its high stability, when used alone, tocopherol has a low oxidation prevention ability (Halliwell B et al., FASEB J., 2, pp 2867-2870, 1988) and is expensive.

Meanwhile, peroxisome is one of intracellular organelles which cause abnormal metabolism functions, and plays a critical role in metabolism of oxygen, glucose, lipid, and hormone, and widely affects controlling of cell proliferation and differentiation, and inflammatory mediators. Also, peroxisome affects, through lipid metabolism and glucose metabolism, insulin sensitivity, the formation of a cell membrane and mast cells, and oxidative stress, thereby playing a critical role in aging and tumorigenesis. Peroxisome proliferator-activated receptor (PPAR) is one of nuclear receptors that control the expression of gene due to a ligand binding, and various fatty acids act as an endogenous ligand. Up to now, three PPAR are known: a peroxisome proliferator-activated receptor alpha (PPARα), a peroxisome proliferator-activated receptor beta (PPARβ/δ), and a peroxisome proliferator-activated receptor gamma (PPARγ)

PPARα generally exists in blood vessel walls, the liver, the heart, muscle, kidney, and brown adipose tissues, and together with fibrates, which is an agonist, PPARα prevents or delays progress of arteriosclerosis, promotes oxidizing fat to prevent obesity. PPARβ or PPARδ generally exists skin, brain or adipose tissues, is engaged in cholestrol antiport, myelination, and cut recovery, and acts as a controller for fatty acid metabolism and energy homestasis. PPARγ generally exists in adipose tissues, and also in blood vessel endodermis, macrophage, and β cells of pancreas, and controls differentiation of adipocytes and plays a critical role in body lipid homestasis. A compound prepared by completely or incompletely activating PPARγ suppresses differentiation of adipocyte to effectively treat obesity, and the incompletely activated compound is effective for the treatment of hyperglycemia as well as obesity. As described above, to prevent and treat a variety of disease that is controlled by an action of PPAR, there is a need to develop a novel compound to effectively control activities of PPAR.

DETAILED DESCRIPTION OF THE INVENTION

Technical Problem

Provided are novel compounds having skin-whitening activities.

Provided are novel compounds having anti-oxidant activities.

Provided are novel compounds having PPAR activities.

Technical Solution

An embodiment of the present invention provides a compound represented by Formula 1 below:

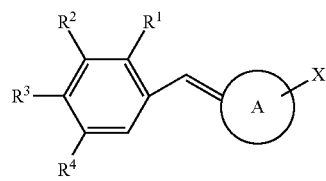

[Formula 1]

wherein $R^1$ to $R^4$ may be identical to or different from each other, and may be any one of H, OH, a $C_1$ to $C_4$ alkoxy, halogen, acetoxy, and benzyloxy, X may be any one of H, phenyl, and $C_1$ to $C_4$ alkyl, and A may be any one of an aromatic ring and a heterocyclic ring, and may be any one of thiazolidine-2,4-dione, pyrimidine-2,4,6(1H,3H,5H)-trione, imidazolidine-2,4-dione, pyrrolidine-2,5-dione, 2-thioxodihydropyrimidine-4,6(1H,5H)-dione, 2-thioxothiazolidine-4-one, 2-imino-1-methylimidazolidine-4-one, 2-methyloxazole-5(4H)-one, 2-thioxoimidazolidine-4-one, 2-iminothiazolidine-4-one, and 2-phenyloxazole-5(4H)-one.

The compound according to the present invention may be a compound represented by Formula 2 below:

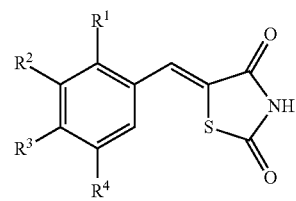

[Formula 2]

wherein $R^1$ to $R^4$ may be identical to or different from each other, and may be any one of H, OH, and a $C_1$ to $C_4$ alkoxy.

The compound according to the present invention may be a compound represented by Formula 3:

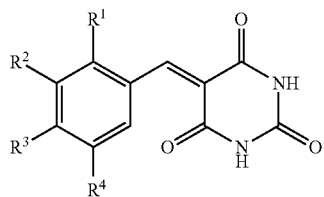

[Formula 3]

wherein $R^1$ to $R^4$ may be identical to or different from each other, and may be any one of H, OH, and a $C_1$ to $C_4$ alkoxy.

The compound according to the present invention may be a compound represented by Formula 4 below:

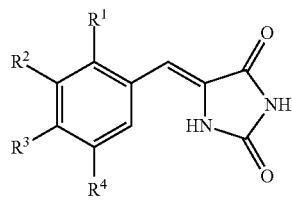

[Formula 4]

wherein $R^1$ to $R^4$ may be identical to or different from each other, and may be any one of H, OH, a $C_1$ to $C_4$ alkoxy, and bromine.

The compound according to the present invention may be a compound represented by Formula 5 below:

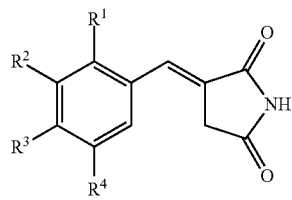

[Formula 5]

wherein $R^1$ to $R^4$ may be identical to or different from each other, and may be any one of H, OH, and a $C_1$ to $C_4$ alkoxy.

The compound according to the present invention may be a compound represented by Formula 6 below:

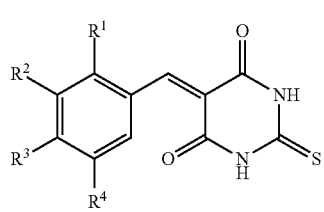

[Formula 6]

wherein $R^1$ to $R^4$ may be identical to or different from each other, and may be any one of H, OH, and a $C_1$ to $C_4$ alkoxy.

The compound according to the present invention may be a compound represented by Formula 7 below:

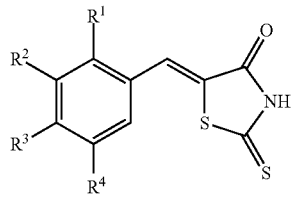

[Formula 7]

wherein $R^1$ to $R^4$ may be identical to or different from each other, and may be any one of H, OH, and a $C_1$ to $C_4$ alkoxy.

The compound according to the present invention may be a compound represented by Formula 8 below:

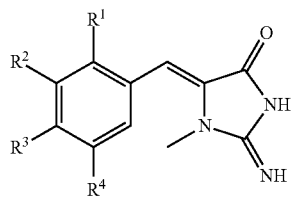

[Formula 8]

wherein $R^1$ to $R^4$ may be identical to or different from each other, and may be any one of H, OH, and a $C_1$ to $C_4$ alkoxy.

The compound according to the present invention may be a compound represented by Formula 9 below:

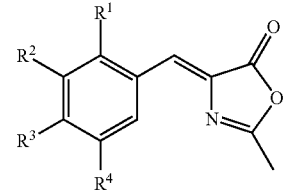

[Formula 9]

wherein $R^1$ to $R^4$ may be identical to or different from each other, and may be any one of H, OH, a $C_1$ to $C_4$ alkoxy, acethoxy, and bromine.

The compound according to the present invention may be a compound represented by Formula 10 below:

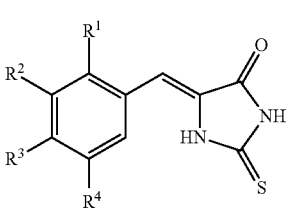

[Formula 10]

wherein $R^1$ to $R^4$ may be identical to or different from each other, and may be any one of H, OH, and a $C_1$ to $C_4$ alkoxy.

The compound according to the present invention may be a compound represented by Formula 11 below:

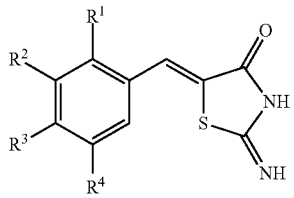

[Formula 11]

wherein $R^1$ to $R^4$ may be identical to or different from each other, and may be any one of H, OH, and a $C_1$ to $C_4$ alkoxy.

The compound according to the present invention may be a compound represented by Formula 12 below:

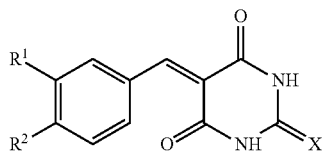

[Formula 12]

wherein $R^1$ and $R^2$ may be different from each other, may be any one of H and benzyloxy, and X may be any one of O and S.

The compound according to the present invention may be a compound represented by Formula 13 below:

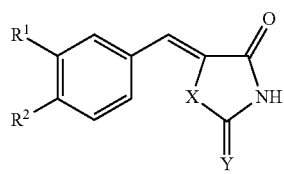

[Formula 13]

wherein $R^1$ and $R^2$ may be different from each other, may be any one of H and benzyloxy, X may be any one of S, $CH_2$, NH, and $NCH_3$, and Y may be any one of O, S, and NH.

The compound according to the present invention may be a compound represented by Formula 14 below:

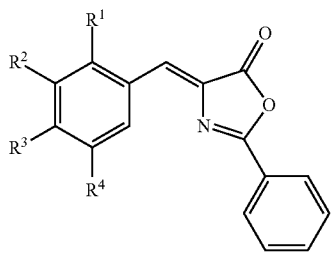

[Formula 14]

wherein $R^1$ to $R^4$ may be identical to or different from each other, and may be any one of H, OH, a $C_1$ to $C_4$ alkoxy, and acethoxy.

The compound according to the present invention may be a compound represented by Formula 15 below:

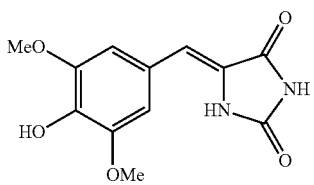

[Formula 15]

Advantageous Effects

Compounds according to the present invention have skin-whitening activities for the suppression of tyrosinase, and accordingly, may be useful for use in skin-whitening pharmaceutical composition or cosmetic products; have anti-oxidant activities, and accordingly, may be useful for the prevention and treatment of skin-aging; and have PPAR activities, and in particular, PPARα and PPARγ activities, and accordingly, may be useful for use in pharmaceutical compositions or health foods which are effective for the prevention and treatment of obesity, metabolic disease, or cardiovascular disease.

BEST MODE

Figure 1:
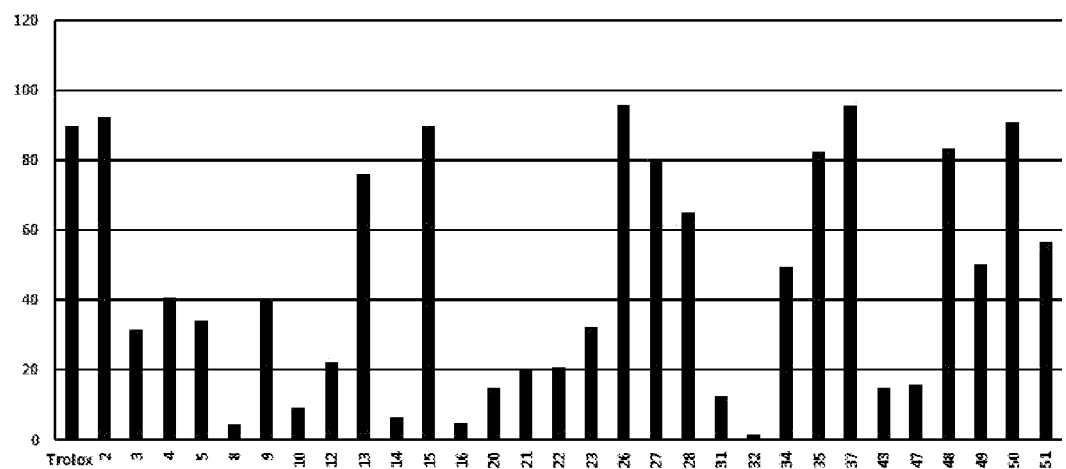
FIGS. 1 to 3 are graphs showing anti-oxidant activities of a compound according to the present invention.

An embodiment of the present invention provides a compound represented by Formula 1 below:

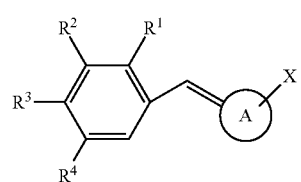

[Formula 1]

wherein $R^1$ to $R^4$ may be identical to or different from each other, and may be any one of H, OH, a $C_1$ to $C_4$ alkoxy, halogen, acetoxy, and benzyloxy, X may be any one of H, phenyl, and $C_1$ to $C_4$ alkyl, and A may be any one of an aromatic ring or a heterocyclic ring, and may be any one of thiazolidine-2,4-dione, pyrimidine-2,4,6(1H,3H,5H)-trione, imidazolidine-2,4-dione, pyrrolidine-2,5-dione, 2-thioxodihydropyrimidine-4,6(1H,5H)-dione, 2-thioxothiazolidine-4-one, 2-imino-1-methylimidazolidine-4-one, 2-methyloxazole-5(4H)-one, 2-thioxoimidazolidine-4-one, 2-iminothiazolidine-4-one, and 2-phenyloxazole-5(4H)-one.

The compound according to the present invention may be a compound represented by Formula 2 below:

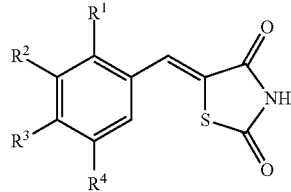

[Formula 2]

wherein $R^1$ to $R^4$ may be identical to or different from each other, and may be any one of H, OH, and a $C_1$ to $C_4$ alkoxy.

In detail, the compound of Formula 2 may be any one selected from the group consisting of (Z)-5-(4-hydroxybenzylidene)thiazolidine-2,4-dione (Compound 1); (Z)-5-(3,4-dihydroxybenzylidene)thiazolidine-2,4-dione (Compound 2); (Z)-5-(2,4-dihydroxybenzylidene)thiazolidine-2,4-dione (Compound 3); (Z)-5-(4-hydroxy-3-methoxybenzylidene)thiazolidine-2,4-dione (Compound 4); (Z)-5-(3-ethoxy-4-hydroxybenzylidene)thiazolidine-2,4-dione (Compound 5); (Z)-5-(3-hydroxy-4-methoxybenzylidene)thiazolidine-2,4-dione (Compound 6); (Z)-5-(4-methoxybenzylidene)thiazolidine-2,4-dione (Compound 7); (Z)-5-(3,4-dimethoxybenzylidene)thiazolidine-2,4-dione (Compound 8); (Z)-5-(3,5-dihydroxybenzylidene)thiazolidine-2,4-dione (Compound 9); (Z)-5-(2,4-dimethoxybenzylidene)thiazolidine-2,4-dione (Compound 10); (Z)-5-(2-hydroxybenzylidene)thiazolidine-2,4-dione (Compound 11); (Z)-5-(3,4,5-trimethoxybenzylidene)thiazolidine-2,4-dione (Compound 12); and (Z)-5-(4-hydroxy-3,5-dimethoxybenzylidene)thiazolidine-2,4-dione (Compound 13).

The compound according to the present invention may be a compound represented by Formula 3:

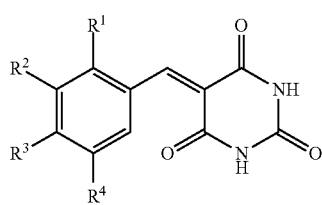

[Formula 3]

wherein $R^1$ to $R^4$ may be identical to or different from each other, and may be any one of H, OH, and a $C_1$ to $C_4$ alkoxy.

In detail, the compound of Formula 3 may be any one selected from the group consisting of 5-(4-hydroxybenzylidene)pyrimidine-2,4,6(1H,3H,5H)-trione (Compound 14); 5-(3,4-dihydroxybenzylidene)pyrimidine-2,4,6(1H,3H,5H)-trione (Compound 15); 5-(2,4-dihyroxybenzylidene)pyrimidine-2,4,6(1H,3H,5H)-trione (Compound 16); 5-(4-hydroxy-3-methoxybenzylidene)pyrimidine-2,4,6(1H,3H,5H)-trione (Compound 17); 5-(3-ethoxy-4-hydroxybenzylidene)pyrimidine-2,4,6(1H,3H,5H)-trione (Compound 18); 5-(3-hydroxy-4-methoxybenzylidene)pyrimidine-2,4,6(1H,3H,5H)-trione (Compound 19); 5-(4-methoxybenzylidene)pyrimidine-2,4,6(1H,3H,5H)-trione (Compound 20); 5-(3,4-dimethoxybenzylidene)pyrimidine-2,4,6 (1H,3H,5H)-trione (Compound 21); 5-(2,4-dimethoxybenzylidene)pyrimidine-2,4,6(1H,3H,5H)-trione (Compound 22); 5-(3,4,5-trimethoxybenzylidene)pyrimidine-2,4,6(1H,3H,5H)-trione (Compound 23); and 5-(4-hydroxy-3,5-dimethoxybenzylidene)pyrimidine-2,4,6(1H,3H, 5H)-trione (Compound 24).

The compound according to the present invention may be a compound represented by Formula 4 below:

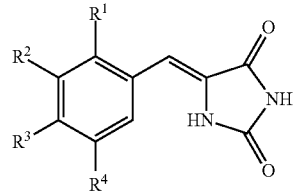

[Formula 4]

wherein $R^1$ to $R^4$ may be identical to or different from each other, and may be any one of H, OH, a $C_1$ to $C_4$ alkoxy, and bromine.

In detail, the compound of Formula 4 may be any one selected from the group consisting of (Z)-5-(4-hydroxybenzylidene)imidazolidine-2,4-dione (Compound 25); (Z)-5-(3,4-dihydroxybenzylidene)imidazolidine-2,4-dione (Compound 26); (Z)-5-(4-hydroxy-3-methoxybenzylidene) imidazolidine-2,4-dione (Compound 27); (Z)-5-(3-ethoxy-4-hydroxybenzylidene)imidazolidine-2,4-dione (Compound 28); (Z)-5-(3-hydroxy-4-methoxybenzylidene)imidazolidine-2,4-dione (Compound 29); (Z)-5-(4-methoxybenzylidene)imidazolidine-2,4-dione (Compound 30); (Z)-5-(3,4-dimethoxybenzylidene)imidazolidine-2,4-dione (Compound 31); (Z)-5-(2,4-dimethoxybenzylidene)imidazolidine-2,4-dione (Compound 32); (Z)-5-(2-hydroxybenzylidene)imidazolidine-2,4-dione (Compound 33); (Z)-5-(3,4,5-trimethoxybenzylidene)imidazolidine-2,4-dione (Compound 34); and (Z)-5-(3-bromo-4-hydroxybenzylidene)imidazolidine-2,4-dione (Compound 35).

The compound according to the present invention may be a compound represented by Formula 5 below:

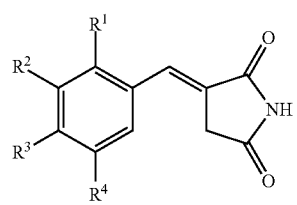

[Formula 5]

wherein $R^1$ to $R^4$ may be identical to or different from each other, and may be any one of H, OH, and a $C_1$ to $C_4$ alkoxy.

In detail, the may be any one of Formula 5 may be any one selected from the group consisting of (E)-3-(4-hydroxybenzylidene)pyrrolidine-2,5-dione (Compound 36); (E)-3-(3,4-dihydroxybenzylidene)pyrrolidine-2,5-dione (Compound 37); (E)-3-(2,4-dihydroxybenzylidene)pyrrolidine-2,5-dione (Compound 38); (E)-3-(4-hydroxy-3-methoxybenzylidene) pyrrolidine-2,5-dione (Compound 39); (E)-3-(3-ethoxy-4-hydroxybenzylidene)pyrrolidine-2,5-dione (Compound 40); (E)-3-(3-hydroxy-4-methoxybenzylidene)pyrrolidine-2,5-dione (Compound 41); (E)-3-(4-methoxybenzylidene)pyrrolidine-2,5-dione (Compound 42); (E)-3-(3,4-dimethoxybenzylidene)pyrrolidine-2,5-dione (Compound 43); (E)-3-(3,5-dihydroxybenzylidene)pyrrolidine-2,5-dione (Compound 44); (E)-3-(2,4-dimethoxybenzylidene)pyrrolidine-2,5-dione (Compound 45); (E)-3-(2-hydroxybenzylidene)pyrrolidine-2,5-dione (Compound 46); (E)-3-(3,4,5-trimethoxybenzylidene)pyrrolidine-2,5-dione (Compound 47); and (E)-3-(4-hydroxy-3,5-dimethoxybenzylidene)pyrrolidine-2,5-dione (Compound 48).

The compound according to the present invention may be a compound represented by Formula 6 below:

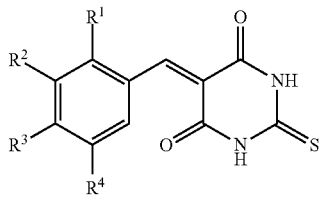

[Formula 6]

wherein $R^1$ to $R^4$ may be identical to or different from each other, and may be any one of H, OH, and a $C_1$ to $C_4$ alkoxy.

In detail, the compound of Formula 6 may be any one selected from the group consisting of 5-(4-hydroxybenzylidene)-2-thioxodihydropyrimidine-4,6(1H,5H)-dione (Compound 49); 5-(3,4-dihydroxybenzylidene)-2-thioxodihydropyrimidine-4,6(1H,5H)-dione (Compound 50); 5-(2,4-dihydroxybenzylidene)-2-thioxodihydropyrimidine-4,6(1H,5H)-dione (Compound 51); 5-(4-hydroxy-3-methoxybenzylidene)-2-thioxodihydropyrimidine-4,6(1H,5H)-dione (Compound 52); 5-(3-ethoxy-4-hydroxybenzylidene)-2-thioxodihydropyrimidine-4,6(1H,5H)-dione (Compound 53); 5-(3-hydroxy-4-methoxybenzylidene)-2-thioxodihydropyrimidine-4,6(1H,5H)-dione (Compound 54); 5-(4-methoxybenzylidene)-2-thioxodihydropyrimidine-4,6(1H,5H)-dione (Compound 55); 5-(3,4-dimethoxybenzylidene)-2-thioxodihydropyrimidine-4,6(1H,5H)-dione (Compound 56); 5-(2,4-dimethoxybenzylidene)-2-thioxodihydropyrimidine-4,6(1H,5H)-dione (Compound 57); 5-(2-hydroxybenzylidene)-2-thioxodihydropyrimidine-4,6(1H,5H)-dione (Compound 58); 2-thioxo-5-(3,4,5-trimethoxybenzylidene)dihydropyrimidine-4,6(1H,5H)-dione (Compound 59); and 5-(4-hydroxy-3,5-dimethoxybenzylidene)-2-thioxodihydropyrimidine-4,6(1H,5H)-dione (Compound 60).

The compound according to the present invention may be a compound represented by Formula 7 below:

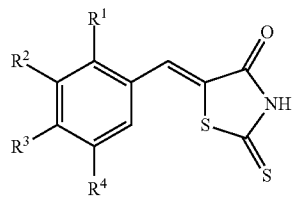

[Formula 7]

wherein $R^1$ to $R^4$ may be identical to or different from each other, and may be any one of H, OH, and a $C_1$ to $C_4$ alkoxy.

In detail, the compound of Formula 7 may be any one selected from the group consisting of (Z)-5-(4-hydroxybenzylidene)-2-thioxothiazolidin-4-one (Compound 61); (Z)-5-(3,4-dihydroxybenzylidene)-2-thioxothiazolidin-4-one (Compound 62); (Z)-5-(2,4-dihydroxybenzylidene)-2-thioxothiazolidin-4-one (Compound 63); (Z)-5-(4-hydroxy-3-methoxybenzylidene)-2-thioxothiazolidin-4-one (Compound 64); (Z)-5-(3-ethoxy-4-hydroxybenzylidene)-2-thioxothiazolidin-4-one (Compound 65); (Z)-5-(3-hydroxy-4-methoxybenzylidene)-2-thioxothiazolidin-4-one (Compound 66); (Z)-5-(4-methoxybenzylidene)-2-thioxothiazolidin-4-one (Compound 67); (Z)-5-(3,4-dimethoxybenzylidene)-2-thioxothiazolidin-4-one (Compound 68); (Z)-5-(3,5-dihydroxybenzylidene)-2-thioxothiazolidin-4-one (Compound 69); (Z)-5-(2,4-dimethoxybenzylidene)-2-thioxothiazolidin-4-one (Compound 70); (Z)-5-(2-hydroxybenzylidene)-2-thioxothiazolidin-4-one (Compound 71); (Z)-2-thioxo-5-(3,4,5-trimethoxybenzylidene)thiazolidine-4-one (Compound 72); and (Z)-5-(4-hydroxy-3,5-dimethoxybenzylidene)-2-thioxothiazolidin-4-one (Compound 73).

The compound according to the present invention may be a compound represented by Formula 8 below:

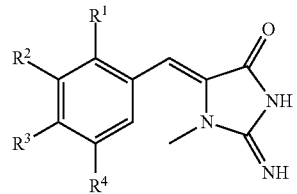

[Formula 8]

wherein $R^1$ to $R^4$ may be identical to or different from each other, and may be any one of H, OH, and a $C_1$ to $C_4$ alkoxy.

In detail, the compound of Formula 8 may be any one selected from the group consisting of (Z)-5-(4-hydroxybenzylidene)-2-imino-1-methylimidazolidin-4-one (Compound 74); (Z)-5-(3,4-dihydroxybenzylidene)-2-imino-1-methylimidazolidin-4-one (Compound 75); (Z)-5-(4-hydroxy-3-methoxybenzylidene)-2-imino-1-methylimidazolidin-4-one (Compound 76); (Z)-5-(3-ethoxy-4-hydroxybenzylidene)-2-imino-1-methylimidazolidin-4-one (Compound 77); (Z)-5-(3-hydroxy-4-methoxybenzylidene)-2-imino-1-methylimidazolidin-4-one (Compound 78); (Z)-2-Imino-5-(4-methoxybenzylidene)-1-methylimidazolidin-4-one (Compound 79); (Z)-5-(3,4-dimethoxybenzylidene)-2-imino-1-methylimidazolidin-4-one (Compound 80); (Z)-5-(2,4-dimethoxybenzylidene)-2-imino-1-methylimidazolidin-4-one (Compound 81); (Z)-2-Imino-1-methyl-5-(3,4,5-trimethoxybenzylidene)imidazolidin-4-one (Compound 82); and (Z)-5-(4-hydroxy-3,5-dimethoxybenzylidene)-2-imino-1-methylimidazolidin-4-one (Compound 82a)

The compound according to the present invention may be a compound represented by Formula 9 below:

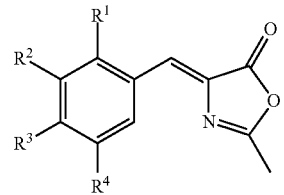

[Formula 9]

wherein $R^1$ to $R^4$ may be identical to or different from each other, and may be any one of H, OH, a $C_1$ to $C_4$ alkoxy, acethoxy, and bromine.

In detail, the compound of Formula 9 may be any one selected from the group consisting of (Z)-4-((2-methyl-5-oxooxazol-4(5H)-ylidene)methyl)phenyl acetate (Compound 83); (Z)-4-((2-methyl-5-oxooxazol-4(5H)-ylidene)methyl)-1,2-phenylene diacetate (Compound 84); (Z)-3-hydroxy-4-((2-methyl-5-oxooxazol-4(5H)-ylidene)methyl)phenyl acetate (Compound 85); (Z)-2-methoxy-4-((2-methyl-5-oxooxazol-4(5H)-ylidene)methyl)phenyl acetate (Compound 86); (Z)-2-ethoxy-4-((2-methyl-5-oxooxazol-4

(5H)-ylidene)methyl)phenyl acetate (Compound 87); (Z)-2-methoxy-5-((2-methyl-5-oxooxazol-4(5H)-ylidene)methyl) phenyl acetate (Compound 88); (Z)-4-(4-methoxybenzylidene)-2-methyloxazol-5(4H)-one[(Z)-4-(4-methoxybenzylidene)-2-methyloxazol-5(4H)-one (Compound 89); (Z)-4-(3,4-dimethoxybenzylidene)-2-methyloxazol-5(4H)-one (Compound 90); (Z)-5-(2-methyl-5-oxooxazol-4(5H)-ylidene)methyl)-1,3-phenylene diacetate (Compound 91); (Z)-4-(2,4-dimethoxybenzylidene)-2-methyloxazol-5(4H)-one (Compound 92); (Z)-4-(2-hydroxybenzylidene)-2-methyloxazol-5(4H)-one (Compound 93); (Z)-2-methyl-4-(3,4,5-trimethoxybenzylidene)oxazol-5 (4H)-one (Compound 94); (Z)-2,6-dimethoxy-4-((2-methyl-oxooxazol-4(5H)-ylidene)methyl)phenyl acetate (Compound 95); (Z)-2-bromo-4-((2-methyl-5-oxooxazol-4(5H)-ylidene)methyl)phenyl acetate (Compound 96); and (Z)-2,6-dibromo-4-((2-methyl-5-oxooxazol-4(5H)-ylidene)methyl) phenylacetate (Compound 97).

The compound according to the present invention may be a compound represented by Formula 10 below:

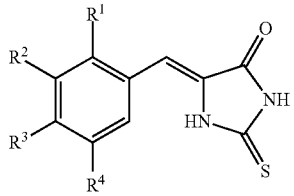

[Formula 10]

wherein R¹ to R⁴ may be identical to or different from each other, and may be any one of H, OH, and a $C_1$ to $C_4$ alkoxy.

In detail, the compound of Formula 10 may be any one selected from the group consisting of (Z)-5-(4-hydroxybenzylidene)-2-thiooxoimidazolidin-4-one (Compound 98); (Z)-(3,4-dihydroxybenzylidene)-2-thiooxoimidazolidin-4-one (Compound 99); (Z)-5-(2,4-dihydroxybenzylidene)-2-thiooxoimidazolidin-4-one (Compound 100); (Z)-5-(4-hydroxy-3-methoxybenzylidene)-2-thiooxoimidazolidin-4-one (Compound 101); (Z)-5-(3-ethoxy-4-hydroxybenzylidene)-2-thiooxoimidazolidin-4-one (Compound 102); (Z)-5-(3-hydroxy-4-methoxybenzylidene)-2-thiooxoimidazolidin-4-one (Compound 103); (Z)-5-(4-methoxybenzylidene)-2-thiooxoimidazolidin-4-one (Compound 104); (Z)-5-(3,4-dimethoxybenzylidene)-2-thiooxoimidazolidin-4-one (Compound 105); (Z)-5-(3,5-dihydroxybenzylidene)-2-thiooxoimidazolidin-4-one (Compound 106); (Z)-5-(2,4-dimethoxybenzylidene)-2-thiooxoimidazolidin-4-one (Compound 107); (Z)-5-(2-hydroxybenzylidene)-2-thiooxoimidazolidin-4-one (Compound 108); (Z)-2-thioxo-5-(3,4,5-trimethoxybenzylidene)imidazolidin-4-one (Compound 109); and (Z)-5-(4-hydroxy-3,5-dimethoxybenzylidene)-2-thiooxoimidazolidin-4-one (Compound 110).

The compound according to the present invention may be a compound represented by Formula 11 below:

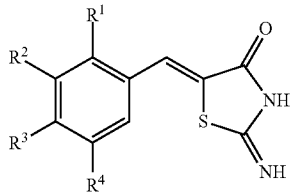

[Formula 11]

wherein R¹ to R⁴ may be identical to or different from each other, and may be any one of H, OH, and a $C_1$ to $C_4$ alkoxy.

In detail, the compound of Formula 11 may be any one selected from the group consisting of (Z)-5-(4-hydroxybenzylidene)-2-iminothiazolidin-4-one (Compound 111); (Z)-(3,4-dihydroxybenzylidene)-2-iminothiazolidin-4-one (Compound 112); (Z)-5-(4-hydroxy-3-methoxybenzylidene)-2-iminothiazolidin-4-one (Compound 113); (Z)-5-(3-ethoxy-4-hydroxybenzylidene)-2-iminothiazolidin-4-one (Compound 114); (Z)-5-(3-hydroxy-4-methoxybenzylidene)-2-iminothiazolidin-4-one (Compound 115); (Z)-2-Imino-5-(4-methoxybenzylidene)thiazolidin-4-one (Compound 116); (Z)-5-(3,4-dimethoxybenzylidene)-2-iminothiazolidin-4-one (Compound 117); (Z)-5-(3,5-dihydroxybenzylidene)-2-iminothiazolidin-4-one (Compound 118); (Z)-5-(2,4-dimethoxybenzylidene)-2-iminothiazolidin-4-one (Compound 119); (Z)-5-(2-hydroxybenzylidene)-2-iminothiazolidin-4-one (Compound 120); (Z)-2-Imino-5-(3,4,5-trimethoxybenzylidene)thiazolidin-4-one (Compound 121); and (Z)-5-(4-hydroxy-3,5-dimethoxybenzylidene)-2-iminothiazolidin-4-one (Compound 122).

The compound according to the present invention may be a compound represented by Formula 12 below:

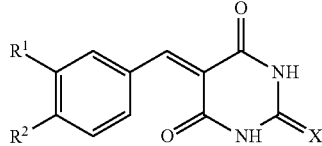

[Formula 12]

wherein R¹ and R² may be different from each other, may be any one of H and benzyloxy, and X may be any one of O and S.

In detail, the compound of Formula 12 may be any one selected from the group consisting of 5-(4-(benzyloxy)benzylidene)pyrimidine-2,4,6(1H,3H,5H)-trione (Compound 123); 5-(4-(benzyloxy)benzylidene)-2-thioxodihydropyrimidine-4,6(1H,5H)-dione (Compound 124); 5-(3-(benzyloxy)benzylidene)pyrimidine-2,4,6(1H,3H,5H)-trione (Compound 132); and 5-(3-(benzyloxy)benzylidene)-2-thioxodihydropyrimidine-4,6(1H,5H)-dione (Compound 133).

The compound according to the present invention may be a compound represented by Formula 13 below:

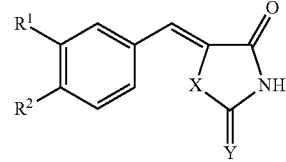

[Formula 13]

wherein R¹ and R² may be different from each other, may be any one of H and benzyloxy, X may be any one of S, $CH_2$, NH, and $NCH_3$, and Y may be any one of O, S, and NH.

In detail, the compound of Formula 13 may be any one selected from the group consisting of (Z)-5-(4-(benzyloxy) benzylidene)thiazolidin-2,4-dione (Compound 125); (Z)-5-(4-(benzyloxy)benzylidene)imidazolidin-2,4-dione (Compound 126); (E)-3-(4-(benzyloxy)benzylidene)pyrrolidin-2,5-dione (Compound 127); (Z)-5-(4-(benzyloxy) benzylidene)-2-thioxothiazolidin-4-one (Compound 128); (E/Z)-5-(4-(benzyloxy)benzylidene)-2-imino-1-methylimidazolidin-4-one (Compound 129); (Z)-5-(4-(benzyloxy)benzylidene)-2-thiooxoimidazolidin-4-one (Compound 130);

(Z)-5-(4-(benzyloxy)benzylidene)-2-iminothiazolidin-4-one (Compound 131); (Z)-5-(3-(benzyloxy)benzylidene)thiazolidin-2,4-dione (Compound 134); (Z)-5-(3-(benzyloxy)benzylidene)imidazolidin-2,4-dione (Compound 135); (E)-3-(3-(benzyloxy)benzylidene)pyrrolidin-2,5-dione (Compound 136); (Z)-5-(3-(benzyloxy)benzylidene)-2-thioxothiazolidin-4-one (Compound 137); (Z)-5-(3-(benzyloxy)benzylidene)-2-thioxoimidazolidin-4-one (Compound 138); and (Z)-5-(3-(benzyloxy)benzylidene)-2-iminothiazolidin-4-one (Compound 139).

The compound according to the present invention may be a compound represented by Formula 14 below:

[Formula 14]

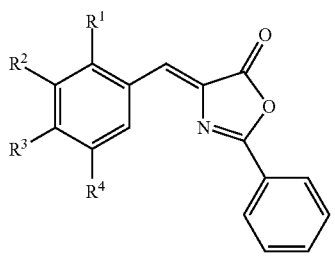

wherein $R^1$ to $R^4$ may be identical to or different from each other, and may be any one of H, OH, a $C_1$ to $C_4$ alkoxy, and acethoxy.

In detail, the compound of Formula 14 may be any one selected from the group consisting of (Z)-4-((5-oxo-2-phenyloxazol-4(5H)-ylidene)methyl)phenyl acetate (Compound 140); (Z)-4-((5-oxo-2-phenyloxazol-4(5H)-ylidene)methyl)-1,2-phenylene diacetate (Compound 141); (Z)-3-hydroxy-4-((5-oxo-2-phenyloxazol-4(5H)-ylidene)methyl) phenyl acetate (Compound 142); (Z)-2-methoxy-4-((5-oxo-2-phenyloxazol-4(5H)-ylidene)methyl)phenyl acetate (Compound 143); (Z)-2-ethoxy-4-((5-oxo-2-phenyloxazol-4 (5H)-ylidene)methyl)phenyl acetate (Compound 144); (Z)-2-methoxy-5-((5-oxo-2-phenyloxazol-4(5H)-ylidene)methyl)phenyl acetate (Compound 145); (Z)-4-(4-methoxybenzylidene)-2-phenyloxazol-5(4H)-one (Compound 146); (Z)-4-(3,4-dimethoxybenzylidene)-2-phenyloxazol-5(4H)-one (Compound 147); (Z)-2-Phenyl-4-(3,4,5-trimethoxybenzylidene)oxazol-5(4H)-one (Compound 148); (Z)-4-(2,4-dimethoxybenzylidene)-2-phenyloxazol-5 (4H)-one (Compound 149); and (Z)-2,6-dimethoxy-4-((5-oxo-2-phenyloxazol-4(5H)-ylidene)methyl)phenyl acetate (Compound 150).

The compound according to the present invention may be a compound represented by Formula 15 below:

[Formula 15]

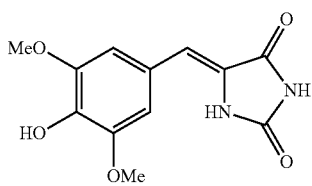 [SMILES: COc1cc(/C=C2\NC(=O)NC2=O)cc(OC)c1O]

The compound may be provided in the form of pharmaceutically acceptable salts thereof, and for example, may be provided in any salt form selected from the group consisting of hydrochloride, bromate, sulphate, phosphate, nitrate, citrate, acetate, lactate, tartarate, maleate, gluconate, succinate, formate, trifluoroacetate, oxalate, fumarate, methane sulfonate, benzene sulfonate, p-toluene sulfonate, and camphor sulfonate.

Also, the present invention provides a composition for skin-whitening including the compound as an active ingredient. The composition may be a pharmaceutical composition or a cosmetic material.

Also, the present invention provides a composition for the prevention or treatment of oxidation-related disease, the composition including the compound as an active ingredient. The composition may be a pharmaceutical composition or a health food.

The oxidation-related disease may be any one of skin aging, skin pigmentation, wrinkle, psoriasis, and eczema.

Also, the present invention provides a composition for the prevention and treatment of a disease that is regulated by a peroxisome proliferator-activated receptor (PPAR), the composition including the compounds as an active ingredient. The composition may be a pharmaceutical composition or a health food.

The PPAR may be a peroxisome proliferator-activated receptor alpha (PPARα) or a peroxisome proliferator-activated receptor gamma (PPARγ), and the disease may be any one of obesity, metabolic disease, and cardiovascular disease.

The metabolic disease may be any one selected from hyperlipidemia, diabetes, hyperinsulinemia, hyperuricemia, hypercholesterolemia, hyper-triglyceridemia, Syndrome X, and endothelial dysfunction, and the cardiovascular disease may be any one selected from hypertension, precoagulant state, dyslipidemia, and atherosclerosis disease.

The pharmaceutical composition according to the present invention may further include appropriate carriers, expedient, or diluents which are conventionally used in preparing pharmaceutical compositions.

Examples of carriers, expedient, or diluents that are available for use in the pharmaceutical composition according to the present invention are lactose, dextrose, sucrose, sorbitol, mannitol, xylitol, erythritol, maltitol, starch, Acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate, and mineral oils.

The pharmaceutical composition according to the present invention may be prepared into an oral formulation, such as a powder formulation, a granule formulation, a tablet formulation, a capsule formulation, a suspension formulation, an emulsion formulation, a syrup formulation, or an aerosol formulation, an external formulation, a suppository formulation, or a sterilized injection solution formation, according to conventional methods.

When prepared into various formulations, a conventional diluent or expedient, such as a filler, a bulking agent, a binding agent, a wetting agent, an disintegrating agent, or a surfactant, may be used. A solid formulation for oral administration may be a tablet formulation, a pill formulation, a powder formulation, a granule formulation, or a capsule formulation, and such solid formulations may be prepared by mixing the compound with one or more expedients selected from, for example, starch, calcium carbonate, sucrose, lactose, and gelatin.

Also, in addition to such expedients, a lubricating agent, such as magnesium stearate or talc, may be used. A liquid formulation for oral administration may be a suspension formulation, an internal solution formulation, an oil formulation, or a syrup formulation, and the liquid formulation may include, in addition to a conventional diluent, such as water or liquid paraffin, various other expedients, for example, a wetting agent, a sweetening agent, a perfuming agent, or a preservative.

A formulation for non-oral administration may be a sterilized aqueous solution formulation, a non-aqueous solution formulation, a suspension formulation, an oil formulation, a lyophilized formulation, or a suppository formulation. For use as the non-aqueous solution formulation and the suspension formulation, propyleneglycol, polyethylene glycol, vegetable oil, such as olive oil, an injectable ester such as ethylolate may be used. As a substrate for the suppository formulation, Witepsol, Macrogol, twin 61, cacao butter, laurin butter, or glycerogelatin may be used.

A dosage of the compound, which is an active ingredient of the pharmaceutical composition according to the present invention, may vary according to the age, gender, body weight, and disease of a patient, and the compositions may be administered in an amount of 0.001 to 100 mg/kg, or 0.01 to 10 mg/kg daily in a bolus or in multiple doses.

Also, a dosage of the compound according to the present invention may vary according to administration path, severance of disease, gender, body weight, or age. Accordingly, the dosage does not limit the scope of the present invention in any aspects.

The pharmaceutical composition may be administered via various pathways to mammal, such as rats, mice, livestock, or humans. All of the administration methods are predictable, and for example, the dosage may be may be orally administered, or the dosage may be administered by rectal or intravenous, nasal, muscular, subcutaneous, intrauterine subdural or intracerebroventricular injection.

The compound according to the present invention has a 50% lethal concentration ($LC_{50}$) of 2 g/kg or more, and thus stability thereof is guaranteed. Accordingly, the compound may be used in a pharmaceutical composition according to the present invention.

Also, the cosmetic composition may include, in addition to the compound according to the present invention, which is an active ingredient, a conventional auxiliary, such as a stabilizer, a solubilizing agent, a vitamin, a pigment, and a fragment, and a perfume.

The cosmetic composition may be prepared in any formulation that is conventionally used in the art. For example, the cosmetic composition may be prepared in the formulation of, for example, solution, suspension, emulsion, paste, gel, cream, lotion, powder, oil, powder foundation, emulsion foundation, wax foundation, and spray, but the formulation thereof is not limited thereto. That is, the cosmetic composition may be prepared in the formulation of sun cream, softening cosmetic water, convergence cosmetic water, nutrition cosmetic water, nutrition cream, massage cream, essence, eye cream, pack, spray, or powder.

When the formulation is paste, cream, or gel, an available carrier component may be, for example, animal oil, vegetable oil, wax, paraffin, starch, tracant, a cellulose derivative, polyethylene glycol, silicon, bentonite, silica, talc, or zinc oxide.

When the formulation is powder or spray, an available carrier component may be, for example, lactose, talc, silica, aluminum hydroixde, calcium silicate, or polyamide powder, and in particular, in the case of spray, additionally, a propellent agent, such as chlorofluorohydrocarbone, propane/butane, or dimethyl ether, may be included.

When the formulation is a solution or an emulsion, an available carrier component may be, for example, a solvent, a solubilizing agent, or an emulsifying agent, and a detailed example thereof is water, ethanol, isopropanol, ethyl carbonate, ethyl acetate, benzyl alcohol, benzyl benzoate, propylene glycol, 1,3-butylglycol oil, glycerol aliphatic ester, polyethyle glycol, or fatty acid ester of sorbitan.

When the formulation is a suspension, an available carrier component may be, for example, a liquid diluent, such as water, ethanol, or propylene; a suspension, such as ethoxylated isostearyl alcohol, polyoxyethylene sorbitol ester, or polyoxyethylene sorbitan ester; microcrystalline cellulose, aluminium metahydroxide, bentonite, agar, or tracant.

Also, the health food may be provided in the form of powder, granule, tablet, capsule, syrup, or beverage, and the health food may include, in addition to the compound according to the present invention, which is an active ingredient, other foods or food additives, and these foods and additives may be appropriately used according to a conventional method. An amount of the active ingredient may be appropriately determined according to purpose, for example, prevention, health, or therapeutic treatment.

An effective amount of the compound included in the health food may vary according to an effective amount of the pharmaceutical composition. However, in the case of a long-term intake for health and sanitation or health control purpose, the amount of the compound may be smaller than the lower limit of the range. Also, the active ingredient is stable and accordingly, when used outside the upper limit of the range, stability is guaranteed.

The health food is not particularly limited, and examples thereof are meat, sausage, bread, chocolate, candies, snacks, biscuits, pizza, instant noodles, other noodles, gums, dairy products including ice cream, various soups, beverages, tea, drinks, alcoholic beverage, and vitamin composites.

Mode of the Invention

Hereinafter, embodiments of the present invention are described in detail by referring to Examples below. However, the examples below do not limit the scope of the present invention.

Example 1

Synthesis of Compounds 1 to 13

Table 1 below is provided to explain substitution patterns of Compounds 1 to 13, which are (Z)-5-(substituted benzylidene)thiazolidine-2,4-diones.

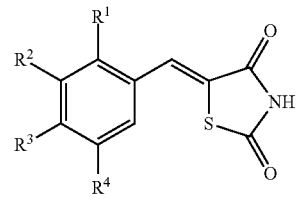

TABLE 1

| Compound | $R^1$ | $R^2$ | $R^3$ | $R^4$ |
|---|---|---|---|---|
| 1 | H | H | OH | H |
| 2 | H | OH | OH | H |
| 3 | OH | H | OH | H |
| 4 | H | OMe | OH | H |
| 5 | H | OEt | OH | H |
| 6 | H | OH | OMe | H |
| 7 | H | H | OMe | H |
| 8 | H | OMe | OMe | H |
| 9 | H | OH | H | OH |
| 10 | OMe | H | OMe | H |

TABLE 1-continued

| Compound | R$^1$ | R$^2$ | R$^3$ | R$^4$ |
|---|---|---|---|---|
| 11 | OH | H | H | H |
| 12 | H | OMe | OMe | OMe |
| 13 | H | OMe | OH | OMe |

OMe represents a methoxy group, and OEt represents an ethoxy group.

Compounds 1 to 13, which are (Z)-5-(substituted benzylidene)thiazolidine-2,4-dione derivatives, were synthesized as follows: In detail, in an ethanol (4 mL) solvent, piperidine (0.3 (eq)) was added to a suspension including substituted benzaldehyde (1.44 to 2.60 mmol) and thiazolidin-2,4-dione (0.7 to 1.2 eq.), and the reaction mixture was refluxed. Before the temperature reached a boiling point of ethanol, in most cases, the reaction mixture turned into a clean solution. During refluxing, a precipitate was formed, and after cooling, the precipitate was filtered. In consideration of the characteristics of benzaldhehyde used in the reaction, a filter cake was washed with ethanol and/or methylene chloride and/or water to obtain a target product (yield: 24 to 79.2%).

Also, in the case of (Z)-5-(2,4-dihydroxybenzylid ene)thiazolidin-2,4-dione (Compound 3), additionally, flash silica gel column chromatography was performed thereon to obtain a more pure target compound.

Example 1-1

Synthesis of (Z)-5-(4-hydroxybenzylidene)thiazolidine-2,4-dione (Compound 1)

Yellow solid; a reaction time of 24 hours; a yield of 67%; a melting point of 299.1-299.7° C.; $^1$H NMR (500 MHz, DMSO-d$_6$) δ 12.44 (s, 1H), 10.30 (s, 1H), 7.68 (s, 1H), 7.43 (d, 2H, J=8.5 Hz), 6.89 (d, 2H, J=8.5 Hz); $^{13}$C NMR (100 MHz, DMSO-d$_6$) δ 168.7, 168.2, 160.6, 133.0, 133.0, 124.6, 119.6, 117.0; LRMS (ES) m/z 220 (M-H)$^-$.

Example 1-2

Synthesis of (Z)-5-(3,4-dihydroxybenzylidene)thiazolidine-2,4-dione (Compound 2)

Greenish yellow solid; a reaction time of 24 hours; a yield of 79.2%; a melting point of >300° C.; $^1$H NMR (400 MHz, CD$_3$OD) δ 7.61 (s, 1H), 6.98 (d, 1H, J=2.0 Hz), 6.92 (dd, 1H, J=8.4, 2.0 Hz), 6.84 (d, 1H, J=8.4 Hz); $^{13}$C NMR (100 MHz, CD$_3$OD) δ 168.8, 168.3, 148.6, 145.9, 133.5, 125.3, 124.2, 119.2, 116.3, 115.7; LRMS (ES) m/z 236 (M-H)$^-$.

Example 1-3

Synthesis of (Z)-5-(2,4-dihydroxybenzylidene)thiazolidine-2,4-dione (Compound 3)

Dark yellow solid; a reaction time of 24 hours; a yield of 45.4%; a melting point of 169.4-171.6° C.; $^1$H NMR (400 MHz, DMSO-d$_6$) δ 12.36 (br s, 1H), 10.40 (s, 1H), 10.13 (br s, 1H), 7.93 (s, 1H), 7.13 (d, 1H, J=8.8 Hz), 6.38 (d, 1H, J=2.4 Hz), 6.36 (dd, 1H, J=8.8, 2.4 Hz); $^{13}$C NMR (100 MHz, DMSO-d$_6$) δ 169.1, 168.5, 162.3, 160.0, 130.6, 128.0, 117.6, 112.3, 109.0, 103.2; LRMS (ES) m/z 236 (M-H)$^-$.

Example 1-4

Synthesis of (Z)-5-(4-Hydroxy-3-methoxybenzylidene)thiazolidine-2,4-dione (Compound 4)

Yellow solid; a reaction time of 18 hours; a yield of 43%; a melting point of 226.0-226.7° C.; $^1$H NMR (500 MHz, CD$_3$OD) δ 7.72 (s, 1H), 7.09 (d, 1H, J=1.5 Hz), 7.07 (dd, 1H, J=2.0, 8.0 Hz), 6.90 (d, 1H, J=8.0 Hz), 3.91 (s, 3H); $^{13}$C NMR (100 MHz, CD$_3$OD) δ 168.5, 168.2, 149.6, 148.3, 133.3, 125.3, 124.7, 119.6, 115.7, 113.2, 55.2; LRMS (ES) m/z 250 (M-H)$^-$.

Example 1-5

Synthesis of (Z)-5-(3-ethoxy-4-hydroxybenzylidene)thiazolidine-2,4-dione (Compound 5)

Greenish yellow solid; a reaction time of 24 hours; a yield of 29%; a melting point of 207.1-208.5° C.; $^1$H NMR (400 MHz, DMSO-d$_6$) δ 12.42 (br s, 1H), 9.84 (s, 1H), 7.67 (s, 1H), 7.11 (d, 1H, J=2.0 Hz), 7.02 (dd, 1H, J=2.4, 8.4 Hz), 6.90 (d, 1H, J=8.0 Hz), 4.04 (q, 2H, J=7.2 Hz), 1.33 (t, 3H, J=7.2 Hz); $^{13}$C NMR (100 MHz, DMSO-d$_6$) δ 168.7, 168.1, 150.4, 147.8, 133.3, 125.1, 124.9, 119.9, 117.0, 116.0, 64.7, 15.3; LRMS (ES) m/z 264 (M-H)$^-$.

Example 1-6

Synthesis of (Z)-5-(3-hydroxy-4-methoxybenzylidene)thiazolidine-2,4-dione (Compound 6)

Greenish yellow solid; a reaction time of 20 hours; a yield of 53%; a melting point of 254.0-257.6° C.; $^1$H NMR (500 MHz, DMSO-d$_6$) δ 12.46 (br s, 1H), 9.48 (s, 1H), 7.63 (s, 1H), 7.06 to 7.01 (m, 3H), 3.82 (s, 3H); $^{13}$C NMR (100 MHz, DMSO-d$_6$) δ 168.7, 168.1, 150.7, 147.6, 132.9, 126.4, 124.1, 120.7, 116.6, 113.2, 56.4; LRMS (ES) m/z 250 (M-H)$^-$.

Example 1-7

Synthesis of (Z)-5-(4-methoxybenzylidene)thiazolidine-2,4-dione (Compound 7)

Yellowish green solid; a reaction time of 24 hours; a yield of 33%; a melting point of 217.6-218.3° C.; $^1$H NMR (400 MHz, CD$_3$OD) δ 7.72 (s, 1H), 7.50 (d, 2H, J=8.4 Hz), 7.04 (d, 2H, J=8.8 Hz), 3.84 (s, 3H); $^{13}$C NMR (100 MHz, DMSO-d$_6$) δ 168.7, 168.1, 161.7, 132.8, 132.5, 126.2, 121.0, 115.6, 56.2; LRMS (ES) m/z 234 (M-H)$^-$.

Example 1-8

Synthesis of (Z)-5-(3,4-dimethoxybenzylidene)thiazolidine-2,4-dione (Compound 8)

Light yellow solid; a reaction time of 23 hours; a yield of 20.4%; a melting point of 214.9-216.7° C.; $^1$H NMR (500 MHz, DMSO-d$_6$) δ 12.50 (br s, 1H), 7.74 (s, 1H), 7.18 (s, 1H), 7.17 (d, 1H, J=8.5 Hz), 7.11 (d, 1H, J=8.5 Hz), 3.81 (s, 3H), 3.80 (s, 3H); $^{13}$C NMR (100 MHz, DMSO-d$_6$) δ 168.7, 168.2, 151.5, 149.6, 132.8, 126.4, 124.4, 121.3, 114.0, 112.8, 56.4, 56.2; LRMS (ES) m/z 264 (M-H)⁻.

Example 1-9

Synthesis of (Z)-5-(3,5-dihydroxybenzylidene)thiazolidine-2,4-dione (Compound 9)

Gray solid; a reaction time of 9 hours; a yield of 24%; a melting point of 288.4-290.2° C.; $^1$H NMR (500 MHz, DMSO-d$_6$) δ 12.53 (s, 1H), 9.62 (s, 2H), 7.54 (s, 1H), 6.43 (d, 2H, J=1.5 Hz), 6.31 (t, 1H, J=1.5 Hz); $^{13}$C NMR (100 MHz, DMSO-d$_6$) δ 168.8, 168.2, 159.6, 135.2, 132.9, 123.9, 108.7, 105.6; LRMS (ES) m/z 236 (M-H)⁻.

Example 1-10

Synthesis of (Z)-5-(2,4-dimethoxybenzylidene)thiazolidine-2,4-dione (Compound 10)

Yellow solid; a reaction time of 7 hours; a yield of 39.6%; a melting point of 254.7-255.6° C.; $^1$H NMR (500 MHz, DMSO-d$_6$) δ 12.42 (br s, 1H), 7.91 (s, 1H), 7.33 (d, 1H, J=8.5 Hz), 6.69 (d, 1H, J=8.5 Hz), 6.68 (s, 1H), 3.88 (s, 3H), 3.83 (s, 3H); $^{13}$C NMR (100 MHz, DMSO-d$_6$) δ 168.9, 168.2, 163.7, 160.5, 130.7, 127.1, 120.6, 114.9, 107.2, 99.3, 56.6, 56.3; LRMS (ES) m/z 264 (M-H)⁻.

Example 1-11

Synthesis of (Z)-5-(2-hydroxybenzylidene)thiazolidine-2,4-dione (Compound 11)

Yellow solid; a reaction time of 21 hours; a yield of 37.1%; a melting point of 254.7-255.9° C.; $^1$H NMR (500 MHz, DMSO-d$_6$) δ 12.53 (s, 1H), 10.52 (s, 1H), 8.03 (s, 1H), 7.33 (d, 1H, J=7.5 Hz), 7.31 (t, 1H, J=8.0 Hz), 6.97 (d, 1H, J=8.0 Hz), 6.95 (t, 1H, J=7.5 Hz); $^{13}$C NMR (100 MHz, DMSO-d$_6$) δ 168.8, 168.2, 157.9, 132.9, 129.0, 127.7, 122.6, 120.6, 120.4, 116.8; LRMS (ES) m/z 220 (M-H)⁻.

Example 1-12

Synthesis of (Z)-5-(3,4,5-trimethoxybenzylidene)thiazolidine-2,4-dione (Compound 12)

Yellow solid; a reaction time of 42 hours; a yield of 38.1%; a melting point of 179.1-181.0° C.; $^1$H NMR (400 MHz, DMSO-d$_6$) δ 12.48 (br s, 1H), 7.71 (s, 1H), 6.88 (s, 2H), 3.79 (s, 6H), 3.68 (s, 3H); $^{13}$C NMR (100 MHz, DMSO-d$_6$) δ 168.5, 168.0, 153.9, 140.1, 132.7, 129.2, 123.2, 108.2, 60.9, 56.7; LRMS (ES) m/z 294 (M-H)⁻.

Example 1-13

Synthesis of (Z)-5-(4-Hydroxy-3,5-dimethoxybenzylidene)thiazolidine-2,4-dione (Compound 13)

Yellow solid; a reaction time of 42 hours; a yield of 47.1%; a melting point of 248.0-249.9° C.; $^1$H NMR (400 MHz, DMSO-d$_6$) δ 12.42 (br s, 1H), 9.31 (s, 1H), 7.67 (s, 1H), 6.85 (s, 2H), 3.78 (s, 6H); $^{13}$C NMR (100 MHz, DMSO-d$_6$) δ 168.7, 168.0, 148.9, 139.3, 133.6, 123.9, 120.2, 108.7, 56.7; LRMS (ES) m/z 280 (M-H)⁻.

Example 2

Synthesis of Compounds 14 to 24

Table 2 below is provided to explain substitution patterns of Compounds 14 to 24, which are 5-(substituted benzylidene)pyrimidine-2,4,6(1H,3H,5H)-trione analogs.

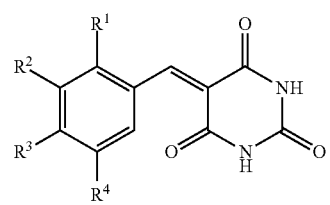

TABLE 2

| Compound | R$^1$ | R$^2$ | R$^3$ | R$^4$ |
|---|---|---|---|---|
| 14 | H | H | OH | H |
| 15 | H | OH | OH | H |
| 16 | OH | H | OH | H |
| 17 | H | OMe | OH | H |
| 18 | H | OEt | OH | H |
| 19 | H | OH | OMe | H |
| 20 | H | H | OMe | H |
| 21 | H | OMe | OMe | H |
| 22 | OMe | H | OMe | H |
| 23 | H | OMe | OMe | OMe |
| 24 | H | OMe | OH | OMe |

OMe represents a methoxy group, and OEt represents an ethoxy group.

Compounds 14 to 24, which are 5-(substituted benzylidene)pyrimidine-2,4,6(1H,3H,5H)-trione analogs, were synthesizes as follows. In detail, in an EtOH (4 mL) and H$_2$O (4 mL) solvent, a suspension including a substituted benzaldehyde (1.44 to 2.60 mmol) and a barbituric acid (0.7 to 1.2 eq.) was heated to a temperature of 80° C. Before the reaction temperature reached 80° C., in most cases, the reaction mixture turned into a clean solution. However, during heating (1 to 18 hours), a precipitate was formed, and after cooling, a precipitate was filtered. In consideration of characteristics of the residual substituted benzaldhehyde, a filter cake was washed with ethanol and/or methylene chloride and water to obtain a target product (yield: 60.3 to 99.3%).

Example 2-1

Synthesis of (5-(4-hydroxybenzylidene)pyrimidine-2,4,6(1H,3H,5H)-trione (Compound 14)

Yellow solid; a reaction time of 6 hours; a yield of 82.6%; a melting point of >300° C.; $^1$H NMR (400 MHz, DMSO-d$_6$) δ 11.23 (s, 1H), 11.10 (s, 1H), 10.79 (s, 1H), 8.29 (d, J=8.8 Hz), 8.17 (s, 1H), 6.84 (d, 2H, J=8.8 Hz); $^{13}$C NMR (100 MHz, DMSO-d$_6$) δ 164.8, 163.7, 163.0, 156.1, 150.9, 139.0, 124.4, 116.2, 114.9; LRMS (ES) m/z 231 (M-H)⁻.

Example 2-2

Synthesis of 5-(3,4-dihydroxybenzylidene)pyrimidine-2,4,6(1H,3H,5H)-trione (Compound 15)

Orange solid; a reaction time of 8 hours; a yield of 99.3%; a melting point of >300° C.; $^1$H NMR (500 MHz, DMSO-$d_6$) δ 11.14 (br s, 2H), 9.76 (br s, 1H), 8.18 (s, 1H), 8.10 (s, 1H), 7.61 (d, 1H, J=8.0 Hz), 6.83 (d, 1H, J=7.5 Hz); $^{13}$C NMR (100 MHz, DMSO-$d_6$) δ 164.9, 162.9, 156.7, 153.0, 150.9, 145.5, 132.0, 124.9, 122.0, 116.0, 114.3; LRMS (ES) m/z 247 (M-H)$^-$.

Example 2-3

Synthesis of 5-(2,4-dihyroxybenzylidene)pyrimidine-2,4,6(1H,3H,5H)-trione (Compound 16)

Yellow solid; a reaction time of 10 hours; a yield of 60.3%; a melting point of >300° C.; $^1$H NMR (500 MHz, D$_2$O+NaOH) δ 8.07 (s, 1H), 7.26 (d, 1H, J=8.5 Hz), 6.44 (dd, 1H, J=2.0, 9.0 Hz), 6.24 (s, 1H); $^{13}$C NMR (100 MHz, DMSO-$d_6$) δ 168.5, 166.7, 162.2, 157.2, 156.8, 145.7, 134.0, 116.5, 113.1, 109.8, 103.3; LRMS (ES) m/z 247 (M-H)$^-$.

Example 2-4

Synthesis of 5-(4-Hydroxy-3-methoxybenzylidene)pyrimidine-2,4,6(1H,3H,5H)-trione (Compound 17)

Dark yellow solid; a reaction time of 18 hours; a yield of 97%; a melting point of 288.6-290.7° C.; $^1$H NMR (400 MHz, DMSO-$d_6$) δ 11.23 (s, 1H), 11.11 (s, 1H), 10.54 (s, 1H), 8.44 (d, 1H, J=2.0 Hz), 8.18 (s, 1H), 7.77 (dd, 1H, J=2.0, 8.4 Hz), 6.86 (d, 1H, J=8.4 Hz), 3.79 (s, 3H); $^{13}$C NMR (100 MHz, DMSO-$d_6$) δ 164.8, 163.2, 156.6, 153.7, 150.9, 147.6, 133.2, 124.9, 118.6, 116.0, 114.6, 56.2; LRMS (ES) m/z 261 (M-H)$^-$.

Example 2-5

Synthesis of 5-(3-Ethoxy-4-hydroxybenzylidene)pyrimidine-2,4,6(1H,3H,5H)-trione (Compound 18)

Orange solid; a reaction time of 15 hours; a yield of 77%; a melting point of 244.7-246.1° C.; $^1$H NMR (500 MHz, DMSO-$d_6$) δ 11.24 (s, 1H), 11.11 (s, 1H), 10.46 (s, 1H), 8.48 (s, 1H), 8.20 (s, 1H), 7.74 (d, 1H, J=8.5 Hz), 6.90 (d, 1H, J=8.5 Hz), 4.08 (q, 2H, J=7.0 Hz), 1.36 (t, 3H, J=7.0 Hz); $^{13}$C NMR (100 MHz, DMSO-$d_6$) δ 164.8, 163.1, 156.6, 154.0, 150.8, 146.8, 133.2, 124.9, 119.7, 116.1, 114.6, 64.5, 15.2; LRMS (ES) m/z 275 (M-H)$^-$.

Example 2-6

Synthesis of 5-(3-Hydroxy-4-methoxybenzylidene)pyrimidine-2,4,6(1H,3H,5H)-trione (Compound 19)

Dark yellow solid; a reaction time of 17 hours; a yield of 93%; a melting point of 279.3-281.4° C.; $^1$H NMR (500 MHz, DMSO-$d_6$) δ 11.26 (s, 1H), 11.13 (s, 1H), 9.42 (s, 1H), 8.14 (s, 1H), 8.10 (s, 1H), 7.70 (d, 1H, J=8.5 Hz), 7.03 (d, 1H, J=9.0 Hz), 3.87 (s, 3H); $^{13}$C NMR (100 MHz, DMSO-$d_6$) δ 164.7, 162.8, 156.2, 153.6, 150.9, 146.4, 131.0, 126.1, 121.1, 115.7, 112.0, 56.4; LRMS (ES) m/z 261 (M-H)$^-$.

Example 2-7

Synthesis of 4-methoxybenzylidene)pyrimidine-2,4,6(1H,3H,5H)-trione (Compound 20)

Yellow solid; a reaction time of 13 hours; a yield of 93%; a melting point of 292.4-294.3° C.; $^1$H NMR (400 MHz, DMSO-$d_6$) δ 11.27 (s, 1H), 11.14 (s, 1H), 8.33 (d, 2H, J=9.2 Hz), 8.21 (s, 1H), 7.02 (d, 2H, J=8.8 Hz), 3.83 (s, 3H); $^{13}$C NMR (100 MHz, DMSO-$d_6$) δ 164.6, 164.1, 162.8, 155.6, 150.9, 138.1, 125.8, 116.2, 114.6, 56.4; LRMS (ES) m/z 245 (M-H)$^-$.

Example 2-8

Synthesis of 5-(3,4-dimethoxybenzylidene)pyrimidine-2,4,6(1H,3H,5H)-trione (Compound 21)

Yellow solid; a reaction time of 9 hours; a yield of 96.6%; a melting point of >300° C.; $^1$H NMR (400 MHz, DMSO-$d_6$) δ 11.27 (s, 1H), 11.15 (s, 1H), 8.37 (d, 1H, J=2.0 Hz), 8.21 (s, 1H), 7.86 (dd, 1H, J=2.0, 8.4 Hz), 7.07 (d, 1H, J=8.4 Hz), 3.84 (s, 3H), 3.77 (s, 3H); $^{13}$C NMR (100 MHz, DMSO-$d_6$) δ 164.7, 163.0, 156.1, 154.3, 150.9, 148.5, 132.4, 125.9, 117.4, 115.9, 111.8, 56.5, 56.1; LRMS (ES) m/z 275 (M-H)$^-$.

Example 2-9

Synthesis of 2,4-dimethoxybenzylidene)pyrimidine-2,4,6(1H,3H,5H)-trione (Compound 22)

Orange solid; a reaction time of 8 hours; a yield of 97%; a melting point of 291.1-291.7° C.; $^1$H NMR (500 MHz, DMSO-$d_6$) δ 11.21 (s, 1H), 11.06 (s, 1H), 8.61 (s, 1H), 8.53 (d, 1H, J=8.5 Hz), 6.63 (d, 1H, J=2.0 Hz), 6.61 (dd, 1H, J=2.0, 9.0 Hz), 3.90 (s, 3H), 3.87 (s, 3H); $^{13}$C NMR (100 MHz, DMSO-$d_6$) δ 166.5, 164.8, 163.1, 162.8, 150.9, 149.7, 136.1, 115.3, 114.9, 106.5, 98.1, 56.9, 56.5; LRMS (ES) m/z 275 (M-H)$^-$.

Example 2-10

Synthesis of 5-(3,4,5-trimethoxybenzylidene)pyrimidine-2,4,6(1H,3H,5H)-trione (Compound 23)

Yellow solid; a reaction time of 1 hours; a yield of 84.0%; a melting point of 274.8-275.4° C.; $^1$H NMR (400 MHz, DMSO-$d_6$) δ 11.33 (s, 1H), 11.20 (s, 1H), 8.22 (s, 1H), 7.80 (s, 2H), 3.78 (s, 6H), 3.75 (s, 3H); $^{13}$C NMR (100 MHz, DMSO-$d_6$) δ 164.4, 162.8, 155.9, 152.6, 150.8, 142.6, 128.2, 117.9, 113.3, 61.0, 56.7; LRMS (ES) m/z 305 (M-H)$^-$.

Example 2-11

Synthesis of 5-(4-hydroxy-3,5-dimethoxybenzylidene)pyrimidine-2,4,6(1H,3H,5H)-trione (Compound 24)

Orange solid; a reaction time of 2 hours; a yield of 99.4%; a melting point of >300° C.; $^1$H NMR (500 MHz, DMSO-$d_6$) δ 11.25 (s, 1H), 11.12 (s, 1H), 9.97 (br s, 1H), 8.24 (s, 1H), 8.00 (s, 2H), 3.82 (s, 6H); $^{13}$C NMR (100 MHz, DMSO-$d_6$) δ

164.8, 163.2, 157.0, 150.9, 147.8, 143.1, 123.5, 114.9, 114.6, 56.7; LRMS (ES) m/z 291 (M-H)⁻.

Example 3

Synthesis of Compounds 25 to 35

Table 3 below is provided to explain substitution patterns of Compounds 25 to 35, which are (Z)-5-(substitutedbenzylidene)imidazolidine-2,4-dione derivatives.

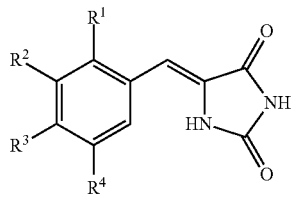

TABLE 3

| Compound | $R^1$ | $R^2$ | $R^3$ | $R^4$ |
|---|---|---|---|---|
| 25 | H | H | OH | H |
| 26 | H | OH | OH | H |
| 27 | H | OMe | OH | H |
| 28 | H | OEt | OH | H |
| 29 | H | OH | OMe | H |
| 30 | H | H | OMe | H |
| 31 | H | OMe | OMe | H |
| 32 | OMe | H | OMe | H |
| 33 | OH | H | H | H |
| 34 | H | OMe | OMe | OMe |
| 35 | H | Br | OH | H |

OMe represents a methoxy group, and OEt represents an ethoxy group.

Synthesis of Compounds 25 to 28, 30, 31, 33, and 35, which are (Z)-5-(substitutedbenzylidene)imidazolidine-2,4-dione derivatives), was performed as follows. In detail, in a piperidine (1 mL/4 mmol of benzaldehyde) solution, a suspension including a substituted benzaldehyde (2.42 to 7.70 mmol) and hydantoin (1.1 eq.) was refluxed for 30 minutes to 8 hours. The reaction mixture was cooled, and at a temperature of 60° C., water (in a volume 20 times greater than that of piperidine used) was added thereto. Filtering was performed to remove a small amount of soft tarry material. A filtrate was acidified at room temperature by using 12N HCl. The mixture was maintained for several hours at room temperature, and then, the produced precipitate was filtered, and the resultant product was washed with cold water and/or methylene chloride. The result was dried under reduced pressure to obtain a target compound (yield: 9.7 to 79%).

Compounds 29, 32, and 34 were synthesized as follows. In detail, in a solvent including ethanol (2 to 4 mL) and H₂O (2 to 4 mL), a suspension including a substituted benzaldehyde (1.08 to 1.28 mmol) and a hydantoin (1.1 eq.) was heated to a temperature of 80° C. The reaction mixture was heated at the same temperature as described above for 30 to 50 hours, and then, the produced precipitate was filtered, and the filtered product was washed with water to remove the remaining unreacted hydantoin. In consideration of the residual substituted benzaldehyde, the resultant product was washed with water and/or methylene chloride and/or ethyl acetate to obtain a target product (yield: 11.4 to 71.4%).

Example 3-1

Synthesis of (Z)-5-(4-hydroxybenzylidene)imidazolidine-2,4-dione (Compound 25)

Light yellow solid; a reaction time of 30 minutes; a yield of 78.5%; a melting point of >300° C.; ¹H NMR (500 MHz, DMSO-d₆) δ 11.10 (s, 1H), 10.30 (s, 1H), 9.84 (s, 1H), 7.46 (d, 2H, J=8.0 Hz), 6.77 (d, 2H, J=8.0 Hz), 6.34 (s, 1H); ¹³C NMR (100 MHz, DMSO-d₆) δ 166.3, 158.7, 156.3, 131.9, 126.0, 124.5, 116.4, 110.0; LRMS (ES) m/z 203 (M-H)⁻.

Example 3-2

Synthesis of (Z)-5-(3,4-dihydroxybenzylidene)imidazolidine-2,4-dione (Compound 26)

Brown solid; a reaction time of 30 minutes; a yield of 68.7%; a melting point of >300° C.; ¹H NMR (400 MHz, CD₃OD) δ 6.92-6.89 (m, 2H), 6.80 (d, 1H, J=8.8 Hz), 6.43 (s, 1H); ¹³C NMR (100 MHz, CD₃OD) δ 166.6, 156.4, 146.8, 145.6, 125.7, 125.1, 121.7, 116.4, 115.6, 111.7; LRMS (ES) m/z 219 (M-H)⁻.

Example 3-3

Synthesis of (Z)-5-(4-hydroxy-3-methoxybenzylidene)imidazolidine-2,4-dione (Compound 27)

Greenish yellow solid; a reaction time of 30 minutes; a yield of 74%; a melting point of 249.2-251.6° C.; ¹H NMR (500 MHz, DMSO-d₆) δ 11.11 (s, 1H), 10.40 (s, 1H), 9.42 (s, 1H), 7.09 (d, 1H, J=1.5 Hz), 7.06 (dd, 1H, J=1.5, 8.5 Hz), 6.78 (d, 1H, J=8.5 Hz), 6.35 (s, 1H), 3.82 (s, 3H); ¹³C NMR (100 MHz, DMSO-d₆) δ 166.3, 156.4, 148.4, 148.2, 126.1, 125.0, 124.1, 116.4, 113.8, 110.5, 56.4; LRMS (ES) m/z 233 (M-H)⁻.

Example 3-4

Synthesis of (Z)-5-(3-ethoxy-4-hydroxybenzylidene)imidazolidine-2,4-dione (Compound 28)

Ochroid solid; a reaction time of 30 minutes; a yield of 79%; a melting point of 253.0-255.4° C.; ¹H NMR (400 MHz, DMSO-d₆) δ 11.08 (s, 1H), 10.36 (s, 1H), 9.32 (s, 1H), 7.06 (d, 1H, J=2.4 Hz), 7.03 (dd, 1H, J=2.0, 8.4 Hz), 6.76 (d, 1H, J=8.0 Hz), 6.30 (s, 1H), 4.06 (q, 2H, J=6.8 Hz), 1.30 (t, 3H, J=6.8 Hz); ¹³C NMR (100 MHz, DMSO-d₆) δ 166.3, 156.4, 148.6, 147.6, 126.1, 125.0, 124.2, 116.5, 115.3, 110.4, 64.7, 15.4; LRMS (ES) m/z 247 (M-H)⁻.

Example 3-5

Synthesis of (Z)-5-(3-hydroxy-4-methoxybenzylidene)imidazolidine-2,4-dione (Compound 29)

Light greenish yellow solid; a reaction time of 40 hours; a yield of 36%; a melting point of 250.7-253.4° C.; ¹H NMR (400 MHz, DMSO-d₆) δ 11.10 (br s, 1H), 10.33 (br s, 1H), 9.01 (s, 1H), 7.05 (dd, 1H, J=2.0, 8.4 Hz), 6.97 (d, 1H, J=2.0 Hz), 6.89 (d, 1H, J=8.4 Hz), 6.25 (s, 1H), 3.77 (s, 3H); ¹³C NMR (100 MHz, DMSO-d₆) δ 166.3, 156.3, 149.0, 147.1, 126.9, 126.4, 121.9, 117.4, 112.7, 109.9, 56.3; LRMS (ES) m/z 233 (M-H)⁻.

Example 3-6

Synthesis of (Z)-5-(4-methoxybenzylidene)imidazolidine-2,4-dione] (Compound 30)

Yellow solid; a reaction time of 4 hours; a yield of 17.4%; a melting point of 241.8-242.9° C.; $^1$H NMR (400 MHz, DMSO-$d_6$) δ 11.13 (s, 1H), 10.40 (s, 1H), 7.55 (d, 2H, J=8.8 Hz), 6.92 (d, 2H, J=8.8 Hz), 6.35 (s, 1H), 3.75 (s, 3H); $^{13}$C NMR (100 MHz, DMSO-$d_6$) δ 166.3, 160.1, 156.3, 131.8, 126.7, 126.1, 115.0, 109.3, 55.9; LRMS (ES) m/z 217 (M-H)$^-$.

Example 3-7

Synthesis of (Z)-5-(3,4-dimethoxybenzylidene)imidazolidine-2,4-dione (Compound 31)

Light yellow solid; a reaction time of 6 hours; a yield of 9.7%; a melting point of 271.3-273.9° C.; $^1$H NMR (500 MHz, DMSO-$d_6$) δ 11.15 (s, 1H), 10.48 (s, 1H), 7.18 (dd, 1H, J=1.5, 8.0 Hz), 7.11 (d, 1H, J=2.0 Hz), 6.95 (d, 1H, J=8.5 Hz), 6.37 (s, 1H), 3.81 (s, 3H), 3.77 (s, 3H); $^{13}$C NMR (100 MHz, DMSO-$d_6$) δ 166.3, 156.4, 150.0, 149.4, 126.8, 126.3, 123.7, 113.2, 112.4, 109.9, 56.3, 56.2; LRMS (ES) m/z 247 (M-H)$^-$.

Example 3-8

Synthesis of (Z)-5-(2,4-dimethoxybenzylidene)imidazolidine-2,4-dione (Compound 32)

White solid; a reaction time of 30 hours; a yield of 71.4%; a melting point of 234.1-237.2° C.; $^1$H NMR (500 MHz, DMSO-$d_6$) δ 11.09 (s, 1H), 10.28 (s, 1H), 7.55 (d, 1H, J=8.5 Hz), 6.60 (s, 1H), 6.59 (d, 1H, J=2.5 Hz), 6.54 (dd, 1H, J=2.0, 8.5 Hz), 3.83 (s, 3H), 3.79 (s, 3H); $^{13}$C NMR (100 MHz, DMSO-$d_6$) δ 166.3, 161.8, 159.3, 156.2, 130.8, 126.7, 114.9, 106.2, 103.7, 98.9, 56.4, 56.1; LRMS (ES) m/z 247 (M-H)$^-$.

Example 3-9

Synthesis of (Z)-5-(2-Hydroxybenzylidene)imidazolidine-2,4-dione (Compound 33)

Yellow solid; a reaction time of 2 hours; a yield of 50.3%; a melting point of 265.5-268.4° C.; $^1$H NMR (500 MHz, DMSO-$d_6$) δ 11.17 (s, 1H), 10.29 (s, 1H), 10.08 (s, 1H), 7.54 (d, 1H, J=8.0 Hz), 7.16 (td, 1H, J=1.0, 8.0 Hz), 6.88 (d, 1H, J=8.0 Hz), 6.82 (t, 1H, J=8.0 Hz), 6.67 (s, 1H); $^{13}$C NMR (100 MHz, DMSO-$d_6$) δ 166.3, 156.5, 156.1, 130.6, 130.0, 127.7, 120.7, 120.0, 116.1, 104.4; LRMS (ES) m/z 203 (M-H)$^-$.

Example 3-10

Synthesis of (Z)-5-(3,4,5-trimethoxybenzylidene)imidazolidine-2,4-dione (Compound 34)

Yellow solid; a reaction time of 50 hours; a yield of 11.4%; a melting point of 266.3-267.2° C.; $^1$H NMR (400 MHz, DMSO-$d_6$) δ 11.19 (br s, 1H), 10.58 (br s, 1H), 6.80 (s, 2H), 6.33 (s, 1H), 3.80 (s, 6H), 3.64 (s, 3H); $^{13}$C NMR (100 MHz, DMSO-$d_6$) δ 166.2, 156.5, 153.7, 138.6, 129.2, 127.9, 109.7, 107.6, 60.7, 56.7; LRMS (ES) m/z 277 (M-H)$^-$.

Example 3-11

Synthesis of (Z)-5-(3-bromo-4-hydroxybenzylidene)imidazolidine-2,4-dione (Compound 35)

A reaction time of 8 hours; a yield of 68.9%; $^1$H NMR (400 MHz, DMSO-$d_6$) δ 11.14 (s, 1H), 10.62 (s, 1H), 10.49 (s, 1H), 7.76 (s, 1H), 7.41 (d, 1H, J=8.8 Hz), 6.92 (d, 1H, J=8.8 Hz), 6.28 (s, 1H); $^{13}$C NMR (100 MHz, DMSO-$d_6$) δ 166.2, 156.3, 155.1, 134.2, 131.0, 127.1, 126.3, 117.0, 110.6, 108.2.

Example 4

Synthesis of Compounds 36 to 48

Table 4 below is provided to explain substitution patterns of Compounds 36 to 48, which are (E)-3-(substituted benzylidene)pyrrolidine-2,5-dione analogs.

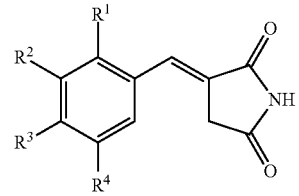

TABLE 4

| Compound | R$^1$ | R$^2$ | R$^3$ | R$^4$ |
|---|---|---|---|---|
| 36 | H | H | OH | H |
| 37 | H | OH | OH | H |
| 38 | OH | H | OH | H |
| 39 | H | OMe | OH | H |
| 40 | H | OEt | OH | H |
| 41 | H | OH | OMe | H |
| 42 | H | H | OMe | H |
| 43 | H | OMe | OMe | H |
| 44 | H | OH | H | OH |
| 45 | OMe | H | OMe | H |
| 46 | OH | H | H | H |
| 47 | H | OMe | OMe | OMe |
| 48 | H | OMe | OH | OMe |

OMe represents a methoxy group, and OEt represents an ethoxy group.

Compounds 36 to 48, which are (E)-3-(substituted benzylidene)pyrrolidine-2,5-diones, were synthesized as follows.

1) Synthesis of triphenylphosphoranylidene succinimide (Compound 36a)

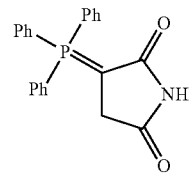

In an anhydrous acetone (60 mL), a solution including maleimide (6 g, 61.81 mmol) and triphenylphosphine (16.2 g, 61.76 mmol) was refluxed for 1 hour. After cooling, a precipitate was filtered, and a filter cake was washed with cold acetone (20 mL). Under reduced pressure, the washed filter cake was dried to obtain a white solid Compound 36a (20.428 g, 92%). The solid was used in following steps without further purification.

melting point, 257.5-260.3° C.; $^1$H NMR (400 MHz, DMSO-$d_6$) δ 9.69 (s, 1H, NH), 7.67 to 7.49 (m, 15H), 2.85 (s, 2H); $^{13}$C NMR (100 MHz, DMSO-$d_6$) δ 178.4, 172.4, 133.8 (d, J=10.7 Hz), 133.3, 129.9 (d, J=12.1 Hz), 126.5 (d, J=133.7 Hz), 38.5, 35.6 (d, J=130.5 Hz).

Example 2

Synthesis of Compounds 36 to 48

In a methanol solvent (5 to 10 mL), a suspension including a substituted benzaldhehyde (0.72 to 2.48 mmol) and triphenylphosphoranylidene succinimide (Compound 36a) (0.72 to 2.48 mmol, 1.0 eq.) was refluxed. Before the temperature reached a boiling point of methanol, in most cases, the reaction mixture turned into a clean solution. During refluxing, a precipitate was formed, and after cooling, the precipitate was filtered. In consideration of characteristics of the substituted benzaldehyde used in the reaction, a filter cake was washed with methanol and an appropriate solvent to obtain Compounds 36 to 48 (yield: 54 to 97.7%).

Example 4-1

Synthesis of (E)-3-(4-hydroxybenzylidene)pyrrolidine-2,5-dione (Compound 36)

White solid; a reaction time of 3 hours; a yield of 54%; a melting point of >300° C.; $^1$H NMR (500 MHz, DMSO-$d_6$) δ 11.29 (s, 1H), 10.04 (s, 1H), 7.45 (d, 2H, J=9.0 Hz), 7.28 (t, 1H, J=2.5 Hz), 6.84 (d, 2H, J=8.5 Hz), 3.56 (d, 2H, J=2.5 Hz); $^{13}$C NMR (100 MHz, DMSO-$d_6$) δ 176.6, 172.9, 159.8, 132.9, 132.5, 125.9, 123.5, 116.6, 35.4; LRMS (ES) m/z 202 (M-H)$^-$.

Example 4-2

Synthesis of (E)-3-(3,4-dihydroxybenzylidene)pyrrolidine-2,5-dione (Compound 37)

Light brown solid; a reaction time of 42 hours; a yield of 58.6%; a melting point of 290.8-291.9° C.; $^1$H NMR (500 MHz, DMSO-$d_6$) δ 11.30 (br s, 1H), 9.47 (br s, 2H), 7.18 (t, 1H, J=2.0 Hz), 6.99 (s, 1H), 6.92 (d, 1H, J=7.5 Hz), 6.80 (d, 1H, J=7.5 Hz), 3.59 (d, 2H, J=2.0 Hz); $^{13}$C NMR (100 MHz, DMSO-$d_6$) δ 176.6, 172.9, 148.4, 146.2, 132.9, 126.3, 124.0, 123.2, 117.6, 116.6, 35.5; LRMS (ES) m/z 218 (M-H)$^-$.

Example 4-3

Synthesis of (E)-3-(2,4-dihydroxybenzylidene)pyrrolidine-2,5-dione (Compound 38)

Very light brown solid; a reaction time of 24 hours; a yield of 82%; a melting point of >300° C.; $^1$H NMR (500 MHz, DMSO-$d_6$) δ 11.18 (s, 1H), 10.04 (s, 1H), 9.92 (s, 1H), 7.65 (s, 1H), 7.28 (d, 1H, J=8.5 Hz), 6.37 (d, 1H, J=2.0 Hz), 6.31 (dd, 1H, J=2.0, 8.5 Hz), 3.50 (s, 2H); $^{13}$C NMR (100 MHz, DMSO-$d_6$) δ 176.8, 173.2, 161.3, 159.5, 131.0, 127.2, 121.2, 113.5, 108.4, 103.0, 35.5; LRMS (ES) m/z 218 (M-H)$^-$.

Example 4-4

Synthesis of (E)-3-(4-hydroxy-3-methoxybenzylidene)pyrrolidine-2,5-dione (Compound 39)

White solid; a reaction time of 14 hours; a yield of 68.5%; a melting point of 243.5-245.7° C.; $^1$H NMR (400 MHz, DMSO-$d_6$) δ 11.28 (s, 1H), 9.65 (s, 1H), 7.25 (t, 1H, J=2.0 Hz), 7.10 (d, 1H, J=2.0 Hz), 7.03 (dd, 1H, J=2.0, 8.4 Hz), 6.81 (d, 1H, J=8.4 Hz), 3.79 (s, 3H), 3.59 (d, 2H, J=2.0 Hz); $^{13}$C NMR (100 MHz, DMSO-$d_6$) δ 176.6, 172.9, 149.3, 148.4, 132.9, 126.3, 125.1, 123.6, 116.5, 114.4, 56.2, 35.3; LRMS (ES) m/z 232 (M-H)$^-$.

Example 4-5

Synthesis of (E)-3-(3-ethoxy-4-hydroxybenzylidene)pyrrolidine-2,5-dione (Compound 40)

White solid; a reaction time of 4 hours; a yield of 58%; a melting point of 222.3-224.1° C.; $^1$H NMR (500 MHz, DMSO-$d_6$) δ 11.29 (s, 1H), 9.57 (s, 1H), 7.27 (s, 1H), 7.11 (s, 1H), 7.05 (d, 1H, J=8.0 Hz), 6.85 (d, 1H, J=8.5 Hz), 4.07 (q, 2H, J=7.0 Hz), 3.60 (s, 2H), 1.34 (t, 3H, J=7.0 Hz); $^{13}$C NMR (100 MHz, DMSO-$d_6$) δ 176.5, 172.8, 149.6, 147.6, 132.9, 126.4, 125.1, 123.6, 116.6, 115.9, 64.6, 35.3, 15.3; LRMS (ES) m/z 246 (M-H)$^-$.

Example 4-6

Synthesis of (E)-3-(3-hydroxy-4-methoxybenzylidene)pyrrolidine-2,5-dione (Compound 41)

White solid; a reaction time of 10 hours; a yield of 85.3%; a melting point of 268.7-270.3° C.; $^1$H NMR (500 MHz, DMSO-$d_6$) δ 11.31 (s, 1H), 9.24 (s, 1H), 7.22 (s, 1H), 7.04 (d, H, J=9.0 Hz), 7.03 (s, 1H), 6.98 (d, 1H, J=8.5 Hz), 3.80 (s, 3H), 3.53 (s, 2H); $^{13}$C NMR (100 MHz, DMSO-$d_6$) δ 176.4, 172.8, 150.0, 147.3, 132.5, 127.7, 124.5, 123.7, 117.1, 112.9, 56.3, 35.5; LRMS (ES) m/z 232 (M-H)$^-$.

Example 4-7

Synthesis of (E)-3-(4-Methoxybenzylidene)pyrrolidine-2,5-dione (Compound 42)

White solid; a reaction time of 5 hours; a yield of 85%; a melting point of 243.4-245.7° C.; $^1$H NMR (500 MHz, DMSO-$d_6$) δ 11.33 (s, 1H), 7.56 (d, 2H, J=7.0 Hz), 7.32 (s, 1H), 7.01 (d, 2H, J=6.5 Hz), 3.79 (s, 3H), 3.58 (s, 2H); $^{13}$C NMR (100 MHz, DMSO-$d_6$) δ 176.4, 172.7, 161.1, 132.7, 132.1, 127.5, 124.7, 115.2, 56.0, 35.4; LRMS (ES) m/z 216 (M-H)$^-$.

Example 4-8

Synthesis of (E)-3-(3,4-dimethoxybenzylidene)pyrrolidine-2,5-dione (Compound 43)

White solid; a reaction time of 5 hours; a yield of 79.6%; a melting point of 237.1-238.4° C.; $^1$H NMR (400 MHz, DMSO-$d_6$) δ 11.31 (s, 1H), 7.29 (s, 1H), 7.14 (d, 1H, J=8.4 Hz), 7.12 (s, 1H), 6.99 (d, 1H, J=8.4 Hz), 3.78 (s, 3H), 3.76 (s, 3H), 3.61 (s, 2H); $^{13}$C NMR (100 MHz, DMSO-$d_6$) δ 176.5, 172.7, 151.0, 149.5, 132.5, 127.6, 124.7, 124.7, 113.8, 112.5, 56.3, 56.2, 35.3; LRMS (ES) m/z 246 (M-H)⁻.

Example 4-9

Synthesis of (E)-3-(3,5-dihydroxybenzylidene)pyrrolidine-2,5-dione (Compound 44)

White solid; a reaction time of 1.5 hours; a yield of 79.3%; a melting point of 275.2-277.8° C.; $^1$H NMR (500 MHz, DMSO-d$_6$) δ 11.37 (s, 1H), 9.44 (s, 2H), 7.13 (t, 1H, J=2.0 Hz), 6.43 (d, 2H, J=2.0 Hz), 6.27 (t, 1H, J=2.0 Hz), 3.52 (d, 2H, J=2.0 Hz); $^{13}$C NMR (100 MHz, DMSO-d$_6$) δ 176.3, 172.7, 159.3, 136.3, 132.6, 127.1, 108.9, 104.9, 35.6; LRMS (ES) m/z 218 (M-H)⁻.

Example 4-10

Synthesis of (E)-3-(2,4-dimethoxybenzylidene)pyrrolidine-2,5-dione (Compound 45)

Light yellow solid; a reaction time of 8 hours; a yield of 62%; a melting point of 245.7-246.6° C.; $^1$H NMR (500 MHz, DMSO-d$_6$) δ 11.29 (s, 1H), 7.62 (t, 1H, J=2.0 Hz), 7.46 (d, 1H, J=8.5 Hz), 6.63 (d, 1H, J=2.0 Hz), 6.60 (dd, 1H, J=2.5, 8.5 Hz), 3.85 (s, 3H), 3.81 (s, 3H), 3.54 (d, 2H, J=2.0 Hz); $^{13}$C NMR (100 MHz, DMSO-d$_6$) δ 176.6, 173.0, 162.9, 160.3, 131.0, 126.2, 124.0, 116.1, 106.7, 99.0, 56.5, 56.2), 35.4; LRMS (ES) m/z 246 (M-H)⁻.

Example 4-11

Synthesis of (E)-3-(2-hydroxybenzylidene)pyrrolidine-2,5-dione (Compound 46)

Light yellow solid; a reaction time of 5 hours; a yield of 69.6%; a melting point of 271.3-272.1° C.; $^1$H NMR (500 MHz, DMSO-d$_6$) δ 11.36 (s, 1H), 10.18 (s, 1H), 7.72 (t, 1H, J=2.0 Hz), 7.46 (d, 1H, J=7.5 Hz), 7.24 (t, 1H, J=7.5 Hz), 6.92 (d, 1H, J=8.0 Hz), 6.87 (t, 1H, J=7.5 Hz), 3.59 (d, 2H, J=2.0 Hz); $^{13}$C NMR (100 MHz, DMSO-d$_6$) δ 176.6, 172.9, 157.7, 131.9, 129.7, 126.9, 125.8, 121.7, 120.0, 116.5, 35.4; LRMS (ES) m/z 202 (M-H)⁻.

Example 4-12

Synthesis of (E)-3-(3,4,5-Trimethoxybenzylidene)pyrrolidine-2,5-dione (Compound 47)

White solid; a reaction time of 3 hours; a yield of 66%; a melting point of 191.2-193.6° C.; $^1$H NMR (500 MHz, DMSO-d$_6$) δ 11.39 (s, 1H), 7.33 (s, 1H), 6.90 (s, 2H), 3.82 (s, 6H), 3.71 (s, 2H), 3.69 (s, 3H); $^{13}$C NMR (100 MHz, DMSO-d$_6$) δ 176.5, 172.6, 153.6, 139.5, 132.5, 130.3, 126.5, 108.3, 60.8, 56.6, 35.1; LRMS (ES) m/z 276 (M-H)⁻.

Example 4-13

Synthesis of (E)-3-(4-hydroxy-3,5-dimethoxybenzylidene)pyrrolidine-2,5-dione (Compound 48)

Light yellow solid; a reaction time of 2.5 hours; a yield of 97.7%; a melting point of 236.7-237.7° C.; $^1$H NMR (400 MHz, DMSO-d$_6$) δ 11.29 (s, 1H), 9.01 (s, 1H), 7.27 (s, 1H), 6.83 (s, 2H), 3.78 (s, 6H), 3.64 (s, 2H); $^{13}$C NMR (100 MHz, DMSO-d$_6$) δ 176.6, 172.8, 148.7, 138.5, 133.2, 125.1, 123.9, 108.7, 56.7, 35.2; LRMS (ES) m/z 262 (M-H)⁻.

Example 5

Synthesis of Compounds 49 to 60

Table 5 below is provided to explain substitution patterns of Compounds 49-60, which are 5-(substituted benzylidene)-2-thioxodihydropyrimidine-4,6(1H,5H)-dione analogs.

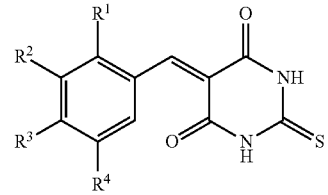

TABLE 5

| Compound | R$^1$ | R$^2$ | R$^3$ | R$^4$ |
|---|---|---|---|---|
| 49 | H | H | OH | H |
| 50 | H | OH | OH | H |
| 51 | OH | H | OH | H |
| 52 | H | OMe | OH | H |
| 53 | H | OEt | OH | H |
| 54 | H | OH | OMe | H |
| 55 | H | H | OMe | H |
| 56 | H | OMe | OMe | H |
| 57 | OMe | H | OMe | H |
| 58 | OH | H | H | H |
| 59 | H | OMe | OMe | OMe |
| 60 | H | OMe | OH | OMe |

OMe represents a methoxy group, and OEt represents an ethoxy group.

Table 5 below is provided to explain substitution patterns of Compounds 49-60, which are 5-(substituted benzylidene)-2-thioxodihydropyrimidine-4,6(1H,5H)-dione analogs. In detail, in a solvent including ethanol (4 to 8 mL) and H2O (4 to 8 mL), a suspension including a substituted benzaldhehyde (1.52 to 1.97 mmol) and a thiobarbituric acid (0.9 to 1.1 eq.) was heated at a temperature of 80° C. Before the reaction temperature reached 80° C., in most cases, the reaction mixture turned into a clean solution. However, during heating (5 minutes to 9 hours), a precipitate was formed, and after cooling, the precipitate was filtered. In consideration of characteristics of the residual substituted benzaldhehyde, a filter cake was washed with ethanol and/or methylene chloride and water to obtain Compounds 49 to 60 (yield: 24 to 99.5%)

Example 5-1

Synthesis of 5-(4-hydroxybenzylidene)-2-thioxodihydropyrimidine-4,6(1H,5H)-dione (Compound 49)

Orange solid; a reaction time of 3 hours; a yield of 96%; a melting point of 291.7-293.5° C.; $^1$H NMR (400 MHz, DMSO-d$_6$) δ 12.30 (s, 1H), 12.20 (s, 1H), 10.93 (s, 1H), 8.34 (d, 2H, J=8.8 Hz), 8.19 (s, 1H), 6.86 (d, 2H, J=8.8 Hz); $^{13}$C NMR (100 MHz, DMSO-d$_6$) δ 178.8, 164.4, 163.1, 160.7, 157.2, 139.5, 124.6, 116.4, 114.9; LRMS (ES) m/z 247 (M-H)⁻.

Example 5-2

Synthesis of 5-(3,4-dihydroxybenzylidene)-2-thioxodihydropyrimidine-4,6(1H,5H)-dione (Compound 50)

Orange solid; a reaction time of 3 hours; a yield of 99.5%; a melting point of >300° C.; $^1$H NMR (400 MHz, DMSO-$d_6$) δ 12.28 (s, 1H), 12.19 (s, 1H), 10.55 (br s, 1H), 9.56 (br s, 1H), 8.25 (s, 1H), 8.10 (s, 1H), 7.63 (d, 1H, J=8.4 Hz), 6.83 (d, 1H, J=8.4 Hz); $^{13}$C NMR (100 MHz, DMSO-$d_6$) δ 178.8, 163.2, 160.7, 157.7, 153.9, 145.7, 132.9, 125.2, 122.1, 116.2, 114.3; LRMS (ES) m/z 263 (M-H)$^-$.

Example 5-3

Synthesis of 5-(2,4-dihydroxybenzylidene)-2-thioxodihydropyrimidine-4,6(1H,5H)-dione (Compound 51)

Dark yellow solid; a reaction time of 5 minutes; a yield of 82.5%; a melting point of >300° C.; $^1$H NMR (400 MHz, DMSO-$d_6$) δ 12.16 (s, 1H), 12.06 (s, 1H), 11.00 (s, 1H), 10.89 (br s, 1H), 8.77 (d, 1H, J=8.8 Hz), 8.76 (s, 1H), 6.37 (d, 1H, J=1.6 Hz), 6.31 (dd, 1H, J=2.0, 9.2 Hz); $^{13}$C NMR (100 MHz, DMSO-$d_6$) δ 178.6, 167.3, 164.8, 163.6, 161.0, 151.2, 137.3, 113.5, 111.9, 109.1, 102.1; LRMS (ES) m/z 263 (M-H)$^-$.

Example 5-4

Synthesis of 5-(4-hydroxy-3-methoxybenzylidene)-2-thioxodihydropyrimidine-4,6(1H,5H)-dione (Compound 52)

Red solid; a reaction time of 3 hours; a yield of 98.8%; a melting point of 260.9-263.6° C.; $^1$H NMR (400 MHz, DMSO-$d_6$) δ 12.31 (s, 1H), 12.20 (s, 1H), 10.70 (s, 1H), 8.46 (s, 1H), 8.20 (s, 1H), 7.83 (d, 1H, J=8.8 Hz), 6.88 (d, 1H, J=8.4 Hz), 3.80 (s, 3H); $^{13}$C NMR (100 MHz, DMSO-$d_6$) δ 178.7, 163.1, 160.9, 157.6, 154.5, 147.7, 133.9, 125.1, 118.9, 116.2, 114.7, 56.2; LRMS (ES) m/z 277 (M-H)$^-$.

Example 5-5

Synthesis of 5-(3-ethoxy-4-hydroxybenzylidene)-2-thioxodihydropyrimidine-4,6(1H,5H)-dione (Compound 53)

Light orange solid; a reaction time of 3 hours; a yield of 88.5%; a melting point of 285.0-287.3° C.; $^1$H NMR (400 MHz, DMSO-$d_6$) δ 12.30 (s, 1H), 12.19 (s, 1H), 10.65 (br s, 1H), 8.47 (d, 1H, J=2.0 Hz), 8.19 (s, 1H), 7.78 (dd, 1H, J=2.0, 8.4 Hz), 6.89 (d, 1H, J=8.4 Hz), 4.05 (q, 2H, J=7.2 Hz), 1.33 (t, 3H, J=7.2 Hz); $^{13}$C NMR (100 MHz, DMSO-$d_6$) δ 178.7, 163.1, 160.9, 157.7, 154.8, 146.9, 134.0, 125.1, 119.8, 116.2, 114.6, 64.5, 15.2; LRMS (ES) m/z 291 (M-H)$^-$.

Example 5-6

Synthesis of 5-(3-hydroxy-4-methoxybenzylidene)-2-thioxodihydropyrimidine-4,6(1H,5H)-dione (Compound 54)

Orange solid; a reaction time of 8 hours; a yield of 97%; a melting point of 278.9-280.5° C.; $^1$H NMR (400 MHz, DMSO-$d_6$) δ 12.32 (s, 1H), 12.23 (s, 1H), 9.58 (br s, 1H), 8.16 (d, 1H, J=2.0 Hz), 8.13 (s, 1H), 7.73 (dd, 1H, J=2.0 Hz, 8.4 Hz), 7.04 (d, 1H, J=8.8 Hz), 3.86 (s, 3H); $^{13}$C NMR (100 MHz, DMSO-$d_6$) δ 178.9, 163.0, 160.6, 157.3, 154.2, 146.6, 131.8, 126.2, 121.2, 115.7, 112.1, 56.6; LRMS (ES) m/z 277 (M-H)$^-$.

Example 5-7

Synthesis of 5-(4-methoxybenzylidene)-2-thioxodihydropyrimidine-4,6(1H,5H)-dione (Compound 55)

Yellow solid; a reaction time of 4 hours; a yield of 77.9%; a melting point of >300° C.; $^1$H NMR (400 MHz, DMSO-$d_6$) δ 12.34 (s, 1H), 12.25 (s, 1H), 8.38 (d, 2H, J=8.8 Hz), 8.23 (s, 1H), 7.04 (d, 2H, J=9.2 Hz), 3.85 (s, 3H); $^{13}$C NMR (100 MHz, DMSO-$d_6$) δ 179.0, 164.7, 162.9, 160.6, 156.6, 138.6, 126.0, 116.3, 114.8, 56.5; LRMS (ES) m/z 261 (M-H)$^-$.

Example 5-8

Synthesis of 5-(3,4-dimethoxybenzylidene)-2-thioxodihydropyrimidine-4,6(1H,5H)-dione (Compound 56)

Dark yellow solid; a reaction time of 4 hours; a yield of 91.9%; a melting point of 269.9-271.7° C.; $^1$H NMR (500 MHz, DMSO-$d_6$) δ 12.37 (s, 1H), 12.26 (s, 1H), 8.41 (s, 1H), 8.26 (s, 1H), 7.95 (d, 1H, J=8.5 Hz), 7.12 (d, 1H, J=8.5 Hz), 3.88 (s, 3H), 3.80 (s, 3H); $^{13}$C NMR (100 MHz, DMSO-$d_6$) δ 178.8, 163.0, 160.8, 157.2, 154.9, 148.5, 133.0, 126.1, 117.6, 116.0, 111.9, 56.6, 56.1; LRMS (ES) m/z 291 (M-H)$^-$.

Example 5-9

Synthesis of 5-(2,4-dimethoxybenzylidene)-2-thioxodihydropyrimidine-4,6(1H,5H)-dione (Compound 57)

Orange solid; a reaction time of 4 hours; a yield of 98.4%; a melting point of 294.1-295.4° C.; $^1$H NMR (400 MHz, DMSO-$d_6$) δ 12.27 (s, 1H), 12.16 (s, 1H), 8.62 (s, 1H), 8.61 (d, 1H, J=8.4 Hz), 6.61 (s, 1H), 6.60 (d, 1H, J=8.0 Hz), 3.89 (s, 3H), 3.86 (s, 3H); $^{13}$C NMR (100 MHz, DMSO-$d_6$) δ 178.9, 167.3, 163.6, 163.1, 160.6, 150.5, 136.5, 115.1, 115.1, 106.9, 98.1, 57.1, 56.7; LRMS (ES) m/z 291 (M-H)$^-$.

Example 5-10

Synthesis of 5-(2-hydroxybenzylidene)-2-thioxodihydropyrimidine-4,6(1H,5H)-dione (Compound 58)

Light yellow solid; a reaction time of hours; a yield of %; a melting point of 250.6-251.4° C.; $^1$H NMR (400 MHz, DMSO-$d_6$) δ 11.40 (s, 1H), 9.75 (s, 1H), 9.60 (s, 1H), 9.00 (s, 1H), 8.01 (dd, 1H, J=2.0, 8.0 Hz), 7.79 (td, 1H, J=2.0, 8.0 Hz), 7.52 (d, 1H, J=8.4 Hz), 7.44 (td, 1H, J=0.8, 7.6 Hz); $^{13}$C NMR (100 MHz, DMSO-$d_6$) δ 181.2, 161.7, 161.1, 154.9, 150.7, 136.1, 131.5, 126.2, 119.0, 118.1, 117.1; LRMS (ES) m/z 247 (M-H)$^-$.

Example 5-11

Synthesis of 2-thioxo-5-(3,4,5-trimethoxybenzylidene)dihydropyrimidine-4,6(1H,5H)-dione (Compound 59)

Orange solid; a reaction time of 1 hours; a yield of 65.5%; a melting point of 258.9-260.7° C.; $^1$H NMR (400 MHz, DMSO-$d_6$) δ 12.41 (s, 1H), 12.30 (s, 1H), 8.24 (s, 1H), 7.85 (s, 2H), 3.79 (s, 6H), 3.77 (s, 3H); $^{13}$C NMR (100 MHz, DMSO-$d_6$) δ 179.0, 162.7, 160.6, 156.8, 152.6, 143.2, 128.3, 118.0, 113.6, 61.0, 56.7; LRMS (ES) m/z 321 (M-H)$^-$.

Example 5-12

Synthesis of 5-(4-hydroxy-3,5-dimethoxybenzylidene)-2-thioxodihydropyrimidine-4,6(1H,5H)-dione (Compound 60)

Orange solid; a reaction time of 2 hours; a yield of 97.5%; a melting point of >300° C.; $^1$H NMR (500 MHz, DMSO-$d_6$) δ 12.33 (s, 1H), 12.23 (s, 1H), 10.17 (br s, 1H), 8.27 (s, 1H), 8.05 (s, 2H), 3.83 (s, 6H); $^{13}$C NMR (100 MHz, DMSO-$d_6$) δ 178.7, 163.2, 160.9, 158.0, 147.9, 144.0, 123.7, 115.0, 114.9, 56.7; LRMS (ES) m/z 307 (M-H)$^-$.

Example 6

Synthesis of Compounds 61 to 73

Table 6 below is provided to explain substitution patterns of Compounds 61 to 73, which are (Z)-5-(substituted benzylidene)-2-thioxothiazolidin-4-one analogs.

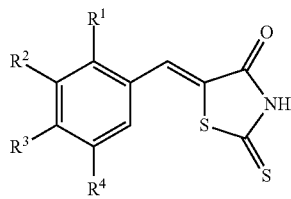

TABLE 6

| Compound | $R^1$ | $R^2$ | $R^3$ | $R^4$ |
|---|---|---|---|---|
| 61 | H | H | OH | H |
| 62 | H | OH | OH | H |
| 63 | OH | H | OH | H |
| 64 | H | OMe | OH | H |
| 65 | H | OEt | OH | H |
| 66 | H | OH | OMe | H |
| 67 | H | H | OMe | H |
| 68 | H | OMe | OMe | H |
| 69 | H | OH | H | OH |
| 70 | OMe | H | OMe | H |
| 71 | OH | H | H | H |
| 72 | H | OMe | OMe | OMe |
| 73 | H | OMe | OH | OMe |

OMe represents a methoxy group, and OEt represents an ethoxy group.

Synthesis of Compounds 61 to 73, which are (Z)-5-(substituted benzylidene)-2-thioxothiazolidin-4-one analogs, was performed as follows. In detail, in an ethanol (4 mL) solvent, piperidine (0.3 eq.) was added to a suspension including a substituted benzaldhehyde (1.44 to 2.60 mmol) and rhodanine (0.7 to 1.2 eq.), and the reaction mixture was refluxed. Before the temperature reached a boiling point of ethanol, in most cases, the reaction mixture turned into a clean solution. During refluxing, a precipitate was formed, and after cooling, the precipitate was filtered. In consideration of characteristics of the residual substituted benzaldhehyde used in the reaction, a filter cake was washed with ethanol and/or methylene chloride and/or water to obtain a target product (yield: 24 to 79.2%). Also, in the case of the purification of (Z)-5-(2,4-dihydroxybenzylidene)-2-thioxothiazolidin-4-one (Compound 63), flash silica gel column chromatography was additionally performed to obtain a more pure target compound.

Example 6-1

Synthesis of (Z)-5-(4-Hydroxybenzylidene)-2-thioxothiazolidin-4-one (Compound 61)

Light brownish yellow solid; a reaction time of 6 hours; a yield of 77.1%; a melting point of 275.5-277.2° C.; $^1$H NMR (400 MHz, DMSO-$d_6$) δ 13.72 (br s, 1H), 10.40 (s, 1H), 7.53 (s, 1H), 7.44 (d, 2H, J=8.8 Hz), 6.89 (d, 2H, J=8.4 Hz); $^{13}$C NMR (100 MHz, DMSO-$d_6$) δ 196.2, 170.2, 161.0, 133.8, 133.1, 124.6, 121.6, 117.2; LRMS (ES) m/z 235 (M-H)$^-$.

Example 6-2

Synthesis of (Z)-5-(3,4-dihydroxybenzylidene)-2-thioxothiazolidin-4-one (Compound 62)

Light orange solid; a reaction time of 5 hours; a yield of 60.4%; a melting point of >300° C.; $^1$H NMR (500 MHz, DMSO-$d_6$) δ 13.63 (br s, 1H), 9.90 (s, 1H), 9.48 (s, 1H), 7.45 (s, 1H), 6.99-6.97 (m, 2H), 6.86 (d, 1H, J=9.0 Hz); $^{13}$C NMR (100 MHz, DMSO-$d_6$) δ 196.2, 170.1, 149.9, 146.7, 133.5, 125.6, 125.0, 121.3, 117.3, 117.1; LRMS (ES) m/z 251 (M-H)$^-$.

Example 6-3

Synthesis of (Z)-5-(2,4-dihydroxybenzylidene)-2-thioxothiazolidin-4-one (Compound 63)

Brown solid; a reaction time of 9 hours; a yield of 84.3%; a melting point of 245.5-247.3° C.; $^1$H NMR (400 MHz, DMSO-$d_6$) δ 13.65 (br s, 1H), 10.60 (s, 1H), 10.28 (s, 1H), 7.76 (s, 1H), 7.10 (d, 1H, J=9.2 Hz), 6.38 (dd, 1H, J=2.4, 9.2 Hz), 6.37 (d, 1H, J=2.4 Hz); $^{13}$C NMR (100 MHz, DMSO-$d_6$) δ 196.4, 170.3, 163.0, 160.5, 131.8, 128.7, 119.4, 112.5, 109.5, 103.2; LRMS (ES) m/z 251 (M-H)$^-$.

Example 6-4

Synthesis of (Z)-5-(4-hydroxy-3-methoxybenzylidene)-2-thioxothiazolidin-4-one (Compound 64)

Yellow solid; a reaction time of 1 hours; a yield of 54.3%; a melting point of 227.7-230.6° C.; $^1$H NMR (500 MHz, DMSO-$d_6$) δ 13.70 (br s, 1H), 10.09 (s, 1H), 7.57 (s, 1H), 7.15 (s, 1H), 7.07 (d, 1H, J=8.5 Hz), 6.93 (d, 1H, J=8.0 Hz), 3.82 (s, 3H); $^{13}$C NMR (100 MHz, DMSO-$d_6$) δ 196.1, 170.1, 150.7, 148.8, 133.4, 125.7, 125.1, 121.8, 117.0, 115.1, 56.3; LRMS (ES) m/z 266 (M-H)$^-$.

Example 6-5

Synthesis of (Z)-5-(3-ethoxy-4-hydroxybenzylidene)-2-thioxothiazolidin-4-one (Compound 65)

Orange solid; a reaction time of 5 hours; a yield of 24.4%; a melting point of 207.8-210.1° C.; $^1$H NMR (500 MHz, DMSO-$d_6$) δ 13.70 (br s, 1H), 10.02 (s, 1H), 7.55 (s, 1H), 7.12 (d, 1H, J=2.0 Hz), 7.06 (dd, 1H, J=2.0, 8.5 Hz), 6.93 (d, 1H, J=8.5 Hz), 4.07 (q, 2H, J=7.0 Hz), 1.35 (t, 3H, J=7.5 Hz); $^{13}$C NMR (100 MHz, DMSO-d$_6$) δ 196.1, 170.1, 150.9, 147.9, 133.5, 125.8, 125.0, 121.7, 117.1, 116.1, 64.6, 15.3; LRMS (ES) m/z 280 (M-H)$^-$.

Example 6-6

Synthesis of (Z)-5-(3-hydroxy-4-methoxybenzylidene)-2-thioxothiazolidin-4-one (Compound 66)

Yellow solid; a reaction time of 4 hours; a yield of 23.0%; a melting point of 210.2-212.5° C.; $^1$H NMR (500 MHz, DMSO-d$_6$) δ 13.72 (br s, 1H), 9.56 (s, 1H), 7.50 (s, 1H), 7.10 (dd, 1H, J=2.0, 8.5 Hz), 7.07 (d, 1H, J=8.5 Hz), 7.00 (d, 1H, J=2.0 Hz), 3.83 (s, 3H); $^{13}$C NMR (100 MHz, DMSO-d$_6$) δ 196.3, 170.1, 151.2, 147.8, 133.0, 126.3, 125.1, 122.7, 116.7, 113.2, 56.4; LRMS (ES) m/z 266 (M-H)$^-$.

Example 6-7

Synthesis of (Z)-5-(4-Methoxybenzylidene)-2-thioxothiazolidin-4-one (Compound 67)

Yellow solid; a reaction time of 5 hours; a yield of 57.8%; a melting point of 250.3-251.7° C.; $^1$H NMR (400 MHz, DMSO-d$_6$) δ 13.70 (br s, 1H), 7.58 (s, 1H), 7.53 (d, 2H, J=8.0 Hz), 7.07 (d, 2H, J=7.6 Hz), 3.80 (s, 3H); $^{13}$C NMR (100 MHz, DMSO-d$_6$) δ 196.2, 170.1, 162.0, 133.4, 132.6, 126.2, 122.9, 115.8, 56.2; LRMS (ES) m/z 250 (M-H)$^-$.

Example 6-8

Synthesis of (Z)-5-(3,4-Dimethoxybenzylidene)-2-thioxothiazolidin-4-one (Compound 68)

Yellow solid; a reaction time of 4 hours; a yield of 54.3%; a melting point of 233.0-234.7° C.; $^1$H NMR (500 MHz, DMSO-d$_6$) δ 13.70 (br s, 1H), 7.60 (s, 1H), 7.19 (dd, 1H, J=2.0, 8.5 Hz), 7.16 (d, 1H, J=2.0 Hz), 7.13 (d, 1H, J=8.0 Hz), 3.82 (s, 3H), 3.81 (s, 3H); $^{13}$C NMR (100 MHz, DMSO-d$_6$) δ 196.2, 170.1, 151.9, 149.8, 133.0, 126.3, 125.3, 123.1, 114.1, 113.0, 56.5, 56.3; LRMS (ES) m/z 280 (M-H)$^-$.

Example 6-9

Synthesis of (Z)-5-(3,5-dihydroxybenzylidene)-2-thioxothiazolidin-4-one (Compound 69)

Dark brown solid; a reaction time of 8 hours; a yield of 22.3%; a melting point of 281.2-284.1° C.; $^1$H NMR (500 MHz, DMSO-d$_6$) δ 13.78 (br s, 1H), 9.68 (s, 2H), 7.41 (s, 1H), 6.44 (s, 2H), 6.32 (s, 1H); $^{13}$C NMR (100 MHz, DMSO-d$_6$) δ 196.5, 170.0, 159.7, 135.1, 132.9, 125.7, 109.1, 105.9; LRMS (ES) m/z 251 (M-H)$^-$.

Example 6-10

Synthesis of (Z)-5-(2,4-dimethoxybenzylidene)-2-thioxothiazolidin-4-one (Compound 70)

Orange solid; a reaction time of 2 hours; a yield of 57.9%; a melting point of 272.7-275.2° C.; $^1$H NMR (500 MHz, DMSO-d$_6$) δ 13.69 (br s, 1H), 7.74 (s, 1H), 7.33 (d, 1H, J=8.5 Hz), 6.70 (d, 1H, J=1.5, 9.0 Hz), 6.68 (d, 1H, J=1.5 Hz), 3.90 (s, 3H), 3.84 (s, 3H); $^{13}$C NMR (100 MHz, DMSO-d$_6$) δ 196.5, 170.2, 164.3, 160.7, 132.1, 127.7, 122.4, 115.0, 107.6, 99.3, 56.6, 56.4; LRMS (ES) m/z 280 (M-H)$^-$.

Example 6-11

Synthesis of (Z)-5-(2-hydroxybenzylidene)-2-thioxothiazolidin-4-one (Compound 71)

Brown solid; a reaction time of 8 hours; a yield of 13.7%; a melting point of 201.3-201.5° C.; $^1$H NMR (500 MHz, DMSO-d$_6$) δ 13.73 (br s, 1H), 10.68 (s, 1H), 7.84 (s, 1H), 7.33 (t, 1H, J=7.5 Hz), 7.30 (d, 1H, J=7.5 Hz), 6.96 (d, 1H, J=7.5 Hz), 6.95 (t, 1H, J=7.5 Hz); $^{13}$C NMR (100 MHz, DMSO-d$_6$) δ 196.7, 170.3, 158.2, 133.5, 129.9, 127.9, 124.5, 120.6, 120.6, 116.9; LRMS (ES) m/z 235 (M-H)$^-$.

Example 6-12

Synthesis of (Z)-2-thioxo-5-(3,4,5-trimethoxybenzylidene)thiazolidine-4-one (Compound 72)

Orange solid; a reaction time of 1 hours; a yield of 32.0%; a melting point of 198.0-200.8° C.; $^1$H NMR (400 MHz, DMSO-d$_6$) δ 12.70 (br s, 1H), 7.57 (s, 1H), 6.87 (s, 2H), 3.81 (s, 6H), 3.70 (s, 3H); $^{13}$C NMR (100 MHz, DMSO-d$_6$) δ 196.2, 170.0, 154.0, 140.4, 132.7, 129.1, 125.0, 108.6, 60.9, 56.7; LRMS (ES) m/z 310 (M-H)$^-$.

Example 6-13

Synthesis of (Z)-5-(4-hydroxy-3,5-dimethoxybenzylidene)-2-thioxothiazolidin-4-one (Compound 73)

Yellow solid; a reaction time of 3 hours; a yield of 61.6%; a melting point of 248.7-250.1° C.; $^1$H NMR (400 MHz, DMSO-d$_6$) δ 12.71 (br s, 1H), 9.45 (s, 1H), 7.54 (s, 1H), 6.84 (s, 2H), 3.79 (s, 6H); $^{13}$C NMR (100 MHz, DMSO-d$_6$) δ 196.0, 170.0, 149.0, 139.9, 133.7, 123.9, 122.1, 109.2, 56.7; LRMS (ES) m/z 296 (M-H)$^-$.

Example 7

Synthesis of Compounds 74 to 82

Table 7 below is provided to explain substitution patterns of Compounds 74 to 82, which are (Z)-5-(substituted benzylidene)-2-imino-1-methylimidazolidin-4-one derivatives.

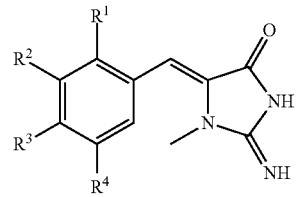

TABLE 7

| Compound | R$^1$ | R$^2$ | R$^3$ | R$^4$ |
|---|---|---|---|---|
| 74 | H | H | OH | H |
| 75 | H | OH | OH | H |
| 76 | H | OMe | OH | H |
| 77 | H | OEt | OH | H |
| 78 | H | OH | OMe | H |
| 79 | H | H | OMe | H |
| 80 | H | OMe | OMe | H |

TABLE 7-continued

| Compound | R$^1$ | R$^2$ | R$^3$ | R$^4$ |
|---|---|---|---|---|
| 81 | OMe | H | OMe | H |
| 82a | H | OMe | OH | OMe |
| 82 | H | OMe | OMe | OMe |

OMe represents a methoxy group, and OEt represents an ethoxy group.

1) Synthesis of (Z)-5-(4-hydroxybenzylidene)-2-imino-1-methylimidazolidin-4-one (Compound 74)

In a piperidine (1 mL) solvent, a mixture including 4-hydroxybenzaldehyde (300 mg, 2.46 mmol) and creatinine (305.7 mg, 2.70 mmol) was refluxed for 2 hours. The reaction product was cooled at a temperature of 60° C., and then, water was added thereto, and the resultant solid was removed therefrom by filtration. 12 N HCl was added to a filtrate, and the produced precipitate was filtered, and the resultant product was washed with water and ethyl acetate to obtain a solid Compound 74.

2) Synthesis of Compounds 75 to 78, and 82 and 82a, which are (Z)-5-(substituted benzylidene)-2-imino-1-methylimidazolidin-4-one derivatives In an acetic acid (4 mL/sodium acetate 1 g) solvent, a mixture including a substituted benzaldhehyde (300 mg, mmol), creatinine (1.1 eq.), and sodium acetate (NaOAc)(3.0 eq.) was refluxed for 2 to 4 hours. After cooling, water was added thereto, and the reaction flask was maintained at a temperature of 0° C. The produced precipitate was filtered, and in consideration of physical characteristics of the residual starting material, the resultant product was washed with iced water and/or methylene chloride to obtain a solid target compound.

3) Synthesis of Compounds 79, 80, and 81, which are (Z)-5-(substituted benzylidene)-2-imino-1-methylimidazolidin-4-one derivatives In a solvent including ethanol (4 mL) and water (2 mL), piperidine (0.3 eq.) was added to an integer of a suspension including a substituted benzaldhehyde (300 mg) and creatinine (1.1 eq.), and then, the reaction mixture was refluxed for 29 to 40 hours. After cooling, the produced precipitate was filtered, and in consideration of the residual starting material, the resultant product was washed with water and methylene chloride and/or ethyl acetate to obtain solid Compounds 79, 80, and 81.

Example 7-1

Synthesis of (Z)-5-(4-hydroxybenzylidene)-2-imino-1-methylimidazolidin-4-one (Compound 74)

Orange solid; a reaction time of 2 hours; a yield of 27.5%; a melting point of 285.9-288.0° C.; $^1$H NMR (400 MHz, DMSO-d$_6$) δ 10.32 (br s, 1H), 9.45 (br s, 2H), 7.98 (d, 2H, J=8.8 Hz), 6.81 (d, 2H, J=8.8 Hz), 6.80 (s, 1H), 3.34 (s, 3H); $^{13}$C NMR (100 MHz, DMSO-d$_6$) δ 162.2, 160.4, 153.5, 134.0, 126.4, 124.5, 123.6, 116.0, 29.5.

Example 7-2

Synthesis of (Z)-5-(3,4-dihydroxybenzylidene)-2-imino-1-methylimidazolidin-4-one (Compound 75)

Light brown solid; a reaction time of 2 hours; a yield of 39.7%; a melting point of 293.0-295.3° C.; $^1$H NMR (400 MHz, DMSO-d$_6$) δ 9.13 (br s, 1H), 8.85 (br s, 1H), 7.83 (d, 1H, J=2.0 Hz), 7.74 (brs, 2H), 7.36 (dd, 1H, J=2.0, 8.0 Hz), 6.64 (d, 1H, J=8.4 Hz), 6.02 (s, 1H), 3.10 (s, 3H); $^{13}$C NMR (100 MHz, DMSO-d$_6$) δ 175.2, 166.1, 146.7, 145.0, 133.2, 126.2, 123.8, 118.4, 115.8, 115.5, 28.5.

Example 7-3

Synthesis of (Z)-5-(4-Hydroxy-3-methoxybenzylidene)-2-imino-1-methylimidazolidin-4-one (Compound 76)

Orange solid; a reaction time of 4 hours; a yield of 15.2%; a melting point of 254.2-255.6° C.; $^1$H NMR (500 MHz, DMSO-d$_6$) δ 8.45 (d, 1H, J=1.0 Hz), 7.85 (brs, 2H), 7.37 (dd, 1H, J=1.0, 8.0 Hz), 6.71 (d, 1H, J=8.0 Hz), 6.17 (s, 1H), 3.78 (s, 3H), 3.15 (s, 3H); $^{13}$C NMR (100 MHz, DMSO-d$_6$) δ 175.1, 165.9, 147.7, 147.4, 133.3, 126.2, 125.3, 116.1, 115.5, 114.8, 56.1, 28.5.

Example 7-4

Synthesis of (Z)-5-(3-ethoxy-4-hydroxybenzylidene)-2-imino-1-methylimidazolidin-4-one (Compound 77)

Orange solid; a reaction time of 3 hours; a yield of 62.4%; a melting point of 254.2-255.6° C.; $^1$H NMR (400 MHz, DMSO-d$_6$) δ 9.14 (br s, 1H), 8.41 (s, 1H), 7.75 (br s, 2H), 7.30 (d, 1H, J=8.0 Hz), 6.69 (d, 1H, J=8.4 Hz), 6.10 (s, 1H), 4.01 (q, 2H, J=6.8 Hz), 3.11 (s, 3H), 1.32 (t, 3H, J=7.2 Hz); $^{13}$C NMR (100 MHz, DMSO-d$_6$) δ 175.3, 166.3, 147.8, 146.5, 133.4, 126.3, 125.3, 115.9, 115.8, 115.6, 64.3, 28.5, 15.4.

Example 7-5

Synthesis of (Z)-5-(3-hydroxy-4-methoxybenzylidene)-2-imino-1-methylimidazolidin-4-one (Compound 78)

Dark yellow solid; a reaction time of 2 hours; a yield of 31.4%; a melting point of 276.1-277.3° C.; $^1$H NMR (500 MHz, DMSO-d$_6$) δ 9.16 (br s, 1H), 8.84 (br s, 1H), 7.84 (d, 1H, J=1.5 Hz), 7.76 (brs, 2H), 7.52 (dd, 1H, J=1.5, 8.5 Hz), 6.86 (d, 1H, J=8.5 Hz), 6.07 (s, 1H), 3.77 (s, 3H), 3.14 (s, 3H); $^{13}$C NMR (100 MHz, DMSO-d$_6$) δ 175.4, 166.6, 148.5, 146.1, 134.1, 127.6, 123.3, 118.1, 114.9, 111.9, 56.2, 28.5.

Example 7-6

Synthesis of (Z)-2-imino-5-(4-methoxybenzylidene)-1-methylimidazolidin-4-one (Compound 79)

Light yellow solid; a reaction time of 30 hours; a yield of 17.9%; a melting point of 252.1-255.0° C.; $^1$H NMR (400 MHz, DMSO-d$_6$) δ 8.13 (d, 2H, J=7.2 Hz), 7.80 (brs, 2H), 6.86 (d, 2H, J=7.2 Hz), 6.14 (s, 1H), 3.73 (s, 3H), 3.12 (s, 3H); $^{13}$C NMR (100 MHz, DMSO-d$_6$) δ 175.5, 166.7, 159.7, 134.2, 132.6, 127.3, 114.4, 114.0, 55.8, 28.5.

Example 7-7

Synthesis of (Z)-5-(3,4-dimethoxybenzylidene)-2-imino-1-methylimidazolidin-4-one (Compound 80)

Light yellow solid; a reaction time of 48 hours; a yield of 13.8%; a melting point of 257.1-259.0° C.; $^1$H NMR (500 MHz, DMSO-$d_6$) δ 8.47 (d, 1H, J=1.5 Hz), 7.84 (brs, 2H), 7.49 (dd, 1H, J=1.5, 8.5 Hz), 6.91 (d, 1H, J=9.0 Hz), 6.18 (s, 1H), 3.77 (s, 3H), 3.76 (s, 3H), 3.16 (s, 3H); $^{13}$C NMR (100 MHz, DMSO-$d_6$) δ 175.6, 166.7, 149.4, 148.5, 134.2, 127.7, 124.8, 115.1, 114.2, 111.7, 56.1, 56.0, 28.5.

Example 7-8

Synthesis of (Z)-5-(2,4-dimethoxybenzylidene)-2-imino-1-methylimidazolidin-4-one (Compound 81)

Light yellow solid; a reaction time of 29 hours; a yield of 38.0%; a melting point of 244.6-245.6° C.; $^1$H NMR (500 MHz, DMSO-$d_6$) δ 8.53 (d, 1H, J=8.5 Hz), 7.80 (brs, 2H), 6.53 (d, 1H, J=2.0 Hz), 6.48 (dd, 1H, J=2.0, 8.5 Hz), 6.30 (s, 1H), 3.81 (s, 3H), 3.78 (s, 3H), 3.13 (s, 3H); $^{13}$C NMR (100 MHz, DMSO-$d_6$) δ 175.5, 166.6, 161.4, 158.7, 133.9, 132.5, 115.3, 107.9, 105.1, 98.2, 56.3, 55.9, 28.4.

Example 7-9

Synthesis of (Z)-2-imino-1-methyl-5-(3,4,5-trimethoxybenzylidene)imidazolidin-4-one (Compound 82)

Light orange solid; a reaction time of 3 hours; a yield of 61.8%; a melting point of 246.5-247.7° C.; $^1$H NMR (400 MHz, DMSO-$d_6$) δ 7.92 (br s, 2H), 7.72 (s, 2H), 6.16 (s, 1H), 3.75 (s, 6H), 3.64 (s, 3H), 3.13 (s, 3H); $^{13}$C NMR (100 MHz, DMSO-$d_6$) δ 175.5, 166.8, 152.8, 135.3, 130.2, 129.1, 115.0, 108.7, 60.7, 56.4, 28.5.

Example 7-10

Synthesis of Z)-5-(4-hydroxy-3,5-dimethoxybenzylidene)-2-imino-1-methylimidazolidin-4-one (Compound 76)

A reaction time of 2 hours; a yield of 65.2%; a melting point of 247.9-249.6° C.; $^1$H NMR (400 MHz, DMSO-$d_6$) δ 7.75 (s, 2H), 6.17 (s, 1H), 3.74 (s, 6H), 3.14 (s, 3H); $^{13}$C NMR (100 MHz, DMSO-$d_6$) δ 175.2, 166.0, 147.9, 136.9, 133.6, 125.1, 116.5, 109.1, 56.5, 28.5.

Example 8

Synthesis of Compounds 83 to 97

Table 8 below is provided to explain substitution patterns of Compounds 83 to 97, which are (Z)-4-(substituted benzylidene)-2-methyloxazol-5(4H)-one analogs.

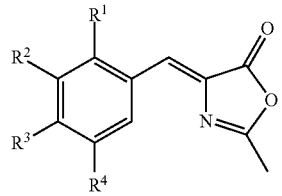

TABLE 8

| Compound | $R^1$ | $R^2$ | $R^3$ | $R^4$ |
|---|---|---|---|---|
| 83 | H | H | OAc | H |
| 84 | H | OAc | OAc | H |
| 85 | OH | H | OAc | H |
| 86 | H | OMe | OAc | H |
| 87 | H | OEt | OAc | H |
| 88 | H | OAc | OMe | H |
| 89 | H | H | OMe | H |
| 90 | H | OMe | OMe | H |
| 91 | H | OAc | H | OAc |
| 92 | OMe | H | OMe | H |
| 93 | OH | H | H | H |
| 94 | H | OMe | OMe | OMe |
| 95 | H | OMe | OAc | OMe |
| 96 | H | Br | OAc | H |
| 97 | H | Br | OAc | Br |

OMe represents a methoxy group, OEt represents an ethoxy group, and AcO represents an acethoxy group.

Synthesis of Compounds 83 to 97, which are (Z)-4-(substituted benzylidene)-2-methyloxazol-5(4H)-one analogs, was performed as follows. In detail, in an acetic anhydride (1.5 eq.+additional 1.0 eq.×the number of phenolic hydroxy groups) solvent, a mixture including a substituted benzaldehyde (300 mg), N-acetylglycine (1.1 eq.), and sodium acetate (0.5 eq.+additional 0.5 eq.×the number of phenolic hydroxy groups) was refluxed for 1 to 7 hours. After cooling, the flask was maintained at a temperature of 0° C., and then, water in which a small amount of methanol (MeOH) was included or was not included was added thereto. The reaction mixture was maintained at a temperature of 0° C., and the produced precipitate was filtered and washed with water to obtain a solid target product. In the case of Compounds 84, 87, 92 and 95, although the reaction mixture was maintained at the temperature of 0° C., a precipitate was not produced. To purify the obtained compound, the resultant product was distributed between ethyl acetate or methylene chloride and water, and then, the resultant organic layer was dried and evaporated, and then, the residual was purified by silica gel column chromatography using hexane and ethyl acetate (2:1) (Compound 84), methylene chloride (Compounds 87 and 95) and hexane and methylene chloride (4:1) (Compound 92) to obtain solid Compounds 84, 87, 92 and 95.

Example 8-1

Synthesis of (Z)-4-((2-methyl-5-oxooxazol-4(5H)-ylidene)methyl)phenyl acetate (Compound 83)

A reaction time of 1 hours; a yield of 43%; $^1$H NMR (400 MHz, CD$_3$OD) δ 8.15 (d, 2H, J=8.8 Hz), 7.17 (d, 2H, J=9.2 Hz), 7.10 (s, 1H), 2.36 (s, 3H), 2.27 (s, 3H); $^{13}$C NMR (100 MHz, CD$_3$OD) δ 169.6, 167.8, 167.2, 152.9, 133.3, 131.2, 130.9, 129.3, 122.0, 19.7, 14.2.

Example 8-2

Synthesis of (Z)-4-(2-Methyl-5-oxooxazol-4(5H)-ylidene)methyl)-1,2-phenylene diacetate (Compound 84)

A reaction time of 3 hours; a yield of 49.7%; $^1$H NMR (400 MHz, CDCl$_3$) δ 7.99 (d, 1H, J=2.0 Hz), 7.77 (dd, 1H, J=2.0, 8.4 Hz), 7.18 (d, 1H, J=8.8 Hz), 6.95 (s, 1H), 2.29 (s, 3H), 2.24 (s, 3H), 2.22 (s, 3H); $^{13}$C NMR (100 MHz, CDCl$_3$) δ 168.2, 168.0, 167.6, 167.0, 144.4, 142.5, 133.4, 132.0, 130.9, 129.2, 126.8, 124.0, 20.8, 20.7, 15.8.

Example 8-3

Synthesis of (Z)-3-hydroxy-4-((2-methyl-5-oxooxazol-4(5H)-ylidene)methyl)phenyl acetate (Compound 85)

A reaction time of 3 hours; a yield of 33.9%; $^1$H NMR (500 MHz, DMSO-d$_6$) δ 9.74 (s, 1H), 8.60 (s, 1H), 7.30 (d, 1H, J=8.5 Hz), 7.25 (d, 1H, J=2.0 Hz), 7.12 (dd, 1H, J=2.0, 8.5 Hz), 2.29 (s, 3H), 2.15 (s, 3H); $^{13}$C NMR (100 MHz, DMSO-d$_6$) δ 170.9, 169.6, 158.0, 151.6, 150.6, 129.2, 124.8, 123.8, 119.7, 118.1, 110.4, 24.6, 21.5.

Example 8-4

Synthesis of (Z)-2-methoxy-4-((2-methyl-5-oxooxazol-4(5H)-ylidene)methyl)phenyl acetate (Compound 86)

A reaction time of 3 hours; a yield of 48.9%; $^1$H NMR (400 MHz, CDCl$_3$) δ 7.90 (d, 1H, J=1.6 Hz), 7.52 (dd, 1H, J=1.6, 8.0 Hz), 7.07 (d, 1H, J=8.0 Hz), 7.06 (s, 1H), 3.87 (s, 3H), 2.37 (s, 3H), 2.30 (s, 3H); $^{13}$C NMR (100 MHz, CDCl$_3$) δ 168.9, 167.2, 166.4, 151.5, 142.3, 132.7, 132.2, 130.8, 126.0, 123.3, 115.5, 56.2, 20.9, 15.9.

Example 8-5

Synthesis of (Z)-2-Ethoxy-4-((2-methyl-5-oxooxazol-4(5H)-ylidene)methyl)phenyl acetate (Compound 87)

A reaction time of 3 hours; a yield of 28%; $^1$H NMR (500 MHz, CDCl$_3$) δ 7.90 (d, 1H, J=1.5 Hz), 7.55 (dd, 1H, J=1.5, 8.5 Hz), 7.09 (d, 1H, J=8.5 Hz), 7.08 (s, 1H), 4.13 (q, 2H, J=7.0 Hz), 2.40 (s, 3H), 2.33 (s, 3H), 1.43 (t, 3H, J=7.0 Hz); $^{13}$C NMR (100 MHz, CDCl$_3$) δ 168.8, 168.0, 166.3, 150.9, 142.7, 132.6, 132.1, 130.9, 125.9, 123.3, 116.5, 64.7, 20.8, 15.9, 14.8.

Example 8-6

Synthesis of (Z)-2-methoxy-5-((2-methyl-5-oxooxazol-4(5H)-ylidene)methyl)phenyl acetate (Compound 88)

A reaction time of 3 hours; a yield of 32.7%; $^1$H NMR (400 MHz, CDCl$_3$) δ 7.96 (d, 1H, J=2.0 Hz), 7.76 (dd, 1H, J=2.0, 8.8 Hz), 7.00 (s, 1H), 6.95 (d, 1H, J=8.4 Hz), 3.84 (s, 3H), 2.34 (s, 3H), 2.30 (s, 3H); $^{13}$C NMR (100 MHz, CDCl$_3$) δ 169.0, 168.1, 165.6, 153.9, 140.1, 132.4, 131.4, 130.5, 126.6, 126.3, 112.3, 56.2, 20.8, 15.8.

Example 8-7

Synthesis of (Z)-4-(4-methoxybenzylidene)-2-methyloxazol-5(4H)-one (Compound 89)

A reaction time of 3 hours; a yield of 22.2%; $^1$H NMR (400 MHz, CDCl$_3$) δ 8.03 (d, 2H, J=8.8 Hz), 7.08 (s, 1H), 6.93 (d, 2H, J=8.8 Hz), 3.84 (s, 3H), 2.36 (s, 3H); $^{13}$C NMR (100 MHz, CDCl$_3$) δ 168.4, 165.1, 162.3, 134.5, 131.7, 130.6, 126.4, 114.7, 55.6, 15.8;

Example 8-8

Synthesis of (Z)-4-(3,4-dimethoxybenzylidene)-2-methyloxazol-5(4H)-one (Compound 90)

A reaction time of 3 hours; a yield of 21.8%; $^1$H NMR (400 MHz, CDCl$_3$) δ 7.89 (d, 1H, J=2.0 Hz), 7.46 (dd, 1H, J=2.0, 8.4 Hz), 7.03 (s, 1H), 6.86 (d, 1H, J=8.4 Hz), 3.91 (s, 3H), 3.90 (s, 3H), 2.35 (s, 3H); $^{13}$C NMR (100 MHz, CDCl$_3$) δ 168.3, 165.1, 152.1, 149.3, 131.8, 130.7, 127.5, 126.6, 114.1, 111.1, 56.2, 56.1, 15.9.

Example 8-9

Synthesis of (Z)-5-(2-methyl-5-oxooxazol-4(5H)-ylidene)methyl)-1,3-phenylene diacetate (Compound 91)

A reaction time of 7 hours; a yield of 31.4%; $^1$H NMR (400 MHz, CDCl$_3$) δ 7.69 (d, 2H, J=2.0 Hz), 7.01 (s, 1H), 6.99 (t, 1H, J=2.0 Hz), 2.39 (s, 3H), 2.29 (s, 6H); $^{13}$C NMR (100 MHz, CDCl$_3$) δ 169.0, 167.5, 167.3, 151.3, 135.1, 134.2, 129.1, 122.5, 118.3, 21.3, 15.9.

Example 8-10

Synthesis of (Z)-4-(2,4-dimethoxybenzylidene)-2-methyloxazol-5(4H)-one (Compound 92)

A reaction time of 3 hours; a yield of 25.2%; $^1$H NMR (500 MHz, CDCl$_3$) δ 8.66 (d, 1H, J=8.5 Hz), 7.68 (s, 1H), 6.59 (dd, 1H, J=2.0, 9.0 Hz), 6.43 (d, 1H, J=2.5 Hz), 3.88 (s, 3H), 3.87 (s, 3H), 2.37 (s, 3H); $^{13}$C NMR (100 MHz, CDCl$_3$) δ 168.6, 164.4, 164.1, 161.1, 134.4, 129.7, 126.0, 115.9, 106.3, 97.9, 55.9, 55.7, 15.8.

Example 8-11

Synthesis of (Z)-4-(2-hydroxybenzylidene)-2-methyloxazol-5(4H)-one (Compound 93)

A reaction time of 3 hours; a yield of 36.3%; $^1$H NMR (500 MHz, CDCl$_3$) δ 8.67 (s, 1H), 8.12 (s, 1H), 7.50 (d, 1H, J=7.5 Hz), 7.43 (t, 1H, J=8.0 Hz), 7.31 (d, 1H, J=8.0 Hz), 7.28 (t, 1H, J=8.0 Hz), 2.25 (s, 3H); $^{13}$C NMR (100 MHz, CDCl$_3$) δ 169.7, 159.0, 150.1, 129.8, 128.0, 125.4, 124.2, 123.5, 120.0, 116.5, 24.9.

Example 8-12

Synthesis of (Z)-2-methyl-4-(3,4,5-trimethoxybenzylidene)oxazol-5(4H)-one (Compound 94)

A reaction time of 3 hours; a yield of 63.8%; $^1$H NMR (400 MHz, CDCl$_3$) δ 7.40 (s, 2H), 7.04 (s, 1H), 3.92 (s, 9H), 2.40

(s, 3H); $^{13}$C NMR (100 MHz, CDCl$_3$) δ 168.1, 165.9, 153.4, 142.0 (C4'), 131.9, 131.6, 128.7, 109.8, 61.2, 56.4, 16.0.

Example 8-13

Synthesis of (Z)-2,6-dimethoxy-4-((2-methyl-5-oxooxazol-4(5H)-ylidene)methyl)phenyl acetate (Compound 95)

A reaction time of 4 hours; a yield of 44.4%; $^1$H NMR (400 MHz, CDCl$_3$) δ 7.38 (s, 2H), 6.99 (s, 1H), 3.84 (s, 6H), 2.36 (s, 3H), 2.32 (s, 3H); $^{13}$C NMR (100 MHz, CDCl$_3$) δ 168.5, 167.9, 166.4, 152.5, 134.5, 132.8, 131.5, 131.1, 109.2, 56.4, 20.6, 15.9.

Example 8-14

Synthesis of (Z)-2-Bromo-4-((2-methyl-5-oxooxazol-4(5H)-ylidene)methyl)phenyl acetate (Compound 96)

A reaction time of 4 hours; a yield of 66.6%; $^1$H NMR (400 MHz, CDCl$_3$) δ 8.39 (d, 1H, J=1.6 Hz), 7.96 (dd, 1H, J=1.6, 8.4 Hz), 7.17 (d, 1H, J=8.8 Hz), 6.99 (s, 1H), 2.39 (s, 3H), 2.35 (s, 3H); $^{13}$C NMR (100 MHz, CDCl$_3$) δ 168.4, 167.5, 167.3, 150.1, 136.7, 133.7, 132.8, 132.5, 128.5, 124.3, 117.1, 21.0, 16.0.

Example 8-15

Synthesis of (Z)-2,6-dibromo-4-((2-methyl-5-oxooxazol-4(5H)-ylidene)methyl)phenylacetate (Compound 97)

A reaction time of 4 hours; a yield of 57.8%; $^1$H NMR (400 MHz, CDCl$_3$) δ 8.27 (s, 2H), 6.90 (s, 1H), 2.41 (s, 3H), 2.39 (s, 3H); $^{13}$C NMR (100 MHz, CDCl$_3$) δ 168.0, 167.2, 167.1, 147.9, 135.5, 134.7, 133.7, 126.9, 118.4, 20.7, 16.0;

Example 9

Synthesis of Compounds 98 to 110

Table 9 below is provided to explain substitution patterns of Compounds 98 to 110, which are (Z)-5-(substituted benzylidene)-2-thioxoimidazolidin-4-one analogs.

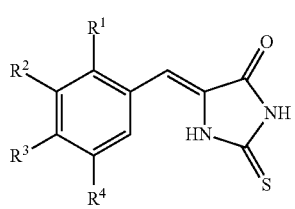

TABLE 9

| Compound | R$^1$ | R$^2$ | R$^3$ | R$^4$ |
|---|---|---|---|---|
| 98 | H | H | OH | H |
| 99 | H | OH | OH | H |
| 100 | OH | H | OH | H |
| 101 | H | OMe | OH | H |
| 102 | H | OEt | OH | H |
| 103 | H | OH | OMe | H |

TABLE 9-continued

| Compound | R$^1$ | R$^2$ | R$^3$ | R$^4$ |
|---|---|---|---|---|
| 104 | H | H | OMe | H |
| 105 | H | OMe | OMe | H |
| 106 | H | OH | H | OH |
| 107 | OMe | H | OMe | H |
| 108 | OH | H | H | H |
| 109 | H | OMe | OMe | OMe |
| 110 | H | OMe | OH | OMe |

OMe represents a methoxy group, and OEt represents an ethoxy group.

Synthesis of Compounds 98 to 110, which are (Z)-5-(substituted benzylidene)-2-thioxoimidazolidin-4-one analogs, was performed as follows. In detail, in an acetic acid (4 mL/sodium acetate 1 g) solvent, a mixture including a substituted benzaldehyde (1.53 to 2.46 mmol), 2-thiohydantoin (1.1 eq.), and sodium acetate (3 eq.) was refluxed for 4 to 24 hours. After cooling, water was added thereto, and the produced precipitate was filtered and in consideration of characteristics of the residual starting materials, the resultant precipitate was washed with water and ethyl acetate and/or methylene chloride to obtain solid Compounds 98 to 110 (yield: 15.1 to 85.2%).

Example 9-1

Synthesis of (Z)-5-(4-hydroxybenzylidene)-2-thioxoimidazolidin-4-one (Compound 98)

Green solid; a reaction time of 4 hours; a yield of 45.0%; a melting point of >300° C.; $^1$H NMR (500 MHz, DMSO-d$_6$) δ 12.23 (s, 1H), 11.96 (s, 1H), 10.02 (s, 1H), 7.61 (d, 2H, J=8.0 Hz), 6.79 (d, 2H, J=8.5 Hz), 6.41 (s, 1H); $^{13}$C NMR (100 MHz, DMSO-d$_6$) δ 178.9, 166.5, 159.7, 133.1, 125.8, 124.0, 116.5, 113.5.

Example 9-2

Synthesis of (Z)-5-(3,4-dihydroxybenzylidene)-2-thioxoimidazolidin-4-one (Compound 99)

Greenish yellow solid; a reaction time of 5 hours; a yield of 76.6%; a melting point of >300° C.; $^1$H NMR (500 MHz, DMSO-d$_6$) δ 12.20 (s, 1H), 11.93 (s, 1H), 9.63 (s, 1H), 9.04 (s, 1H), 7.09 (dd, 1H, J=2.0, 8.0 Hz), 7.07 (d, 1H, J=1.5 Hz), 6.75 (d, 1H, J=8.0 Hz), 6.32 (s, 1H); $^{13}$C NMR (100 MHz, DMSO-d$_6$) δ 178.9, 166.5, 148.3, 146.1, 126.0, 124.4, 123.6, 118.5, 116.5, 114.1.

Example 9-3

Synthesis of (Z)-5-(2,4-Dihydroxybenzylidene)-2-thioxoimidazolidin-4-one (Compound 100)

Yellowish green solid; a reaction time of 5 hours; a yield of 58.1%; a melting point of >300° C.; $^1$H NMR (500 MHz, DMSO-d$_6$) δ 12.13 (s, 1H), 11.65 (s, 1H), 10.30 (s, 1H), 9.92 (s, 1H), 7.56 (d, 1H, J=8.5 Hz), 6.68 (s, 1H), 6.34 (d, 1H, J=2.0 Hz), 6.27 (dd, 1H, J=2.0, 8.5 Hz); $^{13}$C NMR (100 MHz, DMSO-d$_6$) δ 177.7, 166.5, 161.4, 158.9, 132.6, 124.7, 111.8, 109.3, 108.5, 102.9.

Example 9-4

Synthesis of (Z)-5-(4-hydroxy-3-methoxybenzylidene)-2-thioxoimidazolidin-4-one (Compound 101)

Dark yellow solid; a reaction time of 4 hours; a yield of 59.4%; $^1$H NMR (500 MHz, DMSO-$d_6$) δ 12.13 (br s, 2H), 9.15 (br s, 1H), 7.27 (s, 1H), 7.25 (d, 1H, J=8.5 Hz), 6.79 (d, 1H, J=8.0 Hz), 6.37 (s, 1H), 3.83 (s, 3H); $^{13}$C NMR (100 MHz, DMSO-$d_6$) δ 179.1, 167.2, 149.1, 148.4, 127.3, 125.4, 124.8, 116.4, 114.7, 113.6, 56.6.

Example 9-5

Synthesis of (Z)-5-(3-ethoxy-4-hydroxybenzylidene)-2-thioxoimidazolidin-4-one (Compound 102)

Yellow solid; a reaction time of 24 hours; a yield of 15.1%; a melting point of 175.4-177.2° C.; $^1$H NMR (400 MHz, DMSO-$d_6$) δ 12.22 (br s, 1H), 12.01 (br s, 1H), 9.54 (s, 1H), 7.20 (d, 1H, J=8.8 Hz), 7.20 (s, 1H), 6.79 (d, 1H, J=8.8 Hz), 6.39 (s, 1H), 4.08 (q, 2H, J=6.8 Hz), 1.31 (t, 3H, J=6.8 Hz); $^{13}$C NMR (100 MHz, DMSO-$d_6$) δ 179.0, 166.5, 149.6, 147.6, 125.8, 125.5, 124.4, 116.5, 116.0, 114.1, 64.8, 15.3.

Example 9-6

Synthesis of (Z)-5-(3-hydroxy-4-methoxybenzylidene)-2-thioxoimidazolidin-4-one (Compound 103)

Yellowish green solid; a reaction time of 4 hours; a yield of 85.2%; a melting point of 279.6-282.2° C.; $^1$H NMR (500 MHz, DMSO-$d_6$) δ 12.25 (s, 1H), 12.02 (s, 1H), 9.09 (s, 1H), 7.22 (d, 1H, J=8.5 Hz), 7.13 (s, 1H), 6.94 (d, 1H, J=8.0 Hz), 6.35 (s, 1H), 3.81 (s, 3H); $^{13}$C NMR (100 MHz, DMSO-$d_6$) δ 179.2, 166.5, 149.9, 147.1, 126.7, 125.8, 123.3, 117.9, 113.4, 112.7, 56.3.

Example 9-7

Synthesis of (Z)-5-(4-methoxybenzylidene)-2-thioxoimidazolidin-4-one (Compound 104)

Green solid; a reaction time of 4 hours; a yield of 64.0%; a melting point of 266.9-267.5° C.; $^1$H NMR (400 MHz, DMSO-$d_6$) δ 12.26 (s, 1H), 12.03 (s, 1H), 7.70 (d, 2H, J=8.8 Hz), 6.94 (d, 2H, J=8.8 Hz), 6.43 (s, 1H), 3.77 (s, 3H); $^{13}$C NMR (100 MHz, DMSO-$d_6$) δ 179.2, 166.5, 160.9, 132.8, 126.5, 125.5, 115.1, 112.8, 56.0.

Example 9-8

Synthesis of (Z)-5-(3,4-dimethoxybenzylidene)-2-thioxoimidazolidin-4-one (Compound 105)

Greenish yellow solid; a reaction time of 4 hours; a yield of 71.7%; a melting point of 236.2-238.0° C.; $^1$H NMR (500 MHz, DMSO-$d_6$) δ 12.30 (br s, 1H), 12.14 (br s, 1H), 7.35 (dd, 1H, J=2.0, 9.0 Hz), 7.23 (d, 1H, J=2.0 Hz), 6.98 (d, 1H, J=8.5 Hz), 6.45 (s, 1H), 3.83 (s, 3H), 3.80 (s, 3H); $^{13}$C NMR (100 MHz, DMSO-$d_6$) δ 179.3, 166.5, 150.9, 149.5, 126.5, 125.7, 125.0, 114.0, 113.4, 112.4, 56.5, 56.2.

Example 9-9

Synthesis of (Z)-5-(3,5-dihydroxybenzylidene)-2-thioxoimidazolidin-4-one (Compound 106)

Dark brown solid; a reaction time of 6 hours; a yield of 52.6%; a melting point of >300° C.; $^1$H NMR (500 MHz, DMSO-$d_6$) δ 12.29 (s, 1H), 12.03 (s, 1H), 9.38 (s, 2H), 6.52 (s, 2H), 6.27 (s, 2H); $^{13}$C NMR (100 MHz, DMSO-$d_6$) δ 179.8, 166.4, 159.1, 134.5, 128.5, 113.1, 108.9, 104.7.

Example 9-10

Synthesis of (Z)-5-(2,4-dimethoxybenzylidene)-2-thioxoimidazolidin-4-one (Compound 107)

Green solid; a reaction time of 4 hours; a yield of 80.3%; a melting point of 237.1-238.6° C.; $^1$H NMR (500 MHz, DMSO-$d_6$) δ 12.23 (br s, 1H), 11.93 (br s, 1H), 7.73 (d, 1H, J=8.5 Hz), 6.68 (d, 1H, J=1.5 Hz), 6.60 (s, 1H), 6.57 (dd, 1H, J=2.0, 8.5 Hz), 3.85 (s, 3H), 3.82 (s, 3H); $^{13}$C NMR (100 MHz, DMSO-$d_6$) δ 178.8, 166.5, 162.8, 159.9, 132.0, 126.4), 114.3, 107.2, 106.6 (C5'), 98.8, 56.5, 56.2.

Example 9-11

Synthesis of (Z)-5-(2-hydroxybenzylidene)-2-thioxoimidazolidin-4-one (Compound 108)

Dark greenish yellow solid; a reaction time of 4 hours; a yield of 61.4%; a melting point of 283.2-285.1° C.; $^1$H NMR (500 MHz, DMSO-$d_6$) δ 12.28 (s, 1H), 11.84 (s, 1H), 10.30 (s, 1H), 7.66 (d, 1H, J=7.5 Hz), 7.19 (t, 1H, J=8.0 Hz), 6.87 (d, 1H, J=8.0 Hz), 6.82 (t, 1H, J=7.5 Hz), 6.70 (s, 1H); $^{13}$C NMR (100 MHz, DMSO-$d_6$) δ 179.0, 166.4, 157.0, 131.7, 131.1, 127.6, 120.1, 120.1, 116.2, 107.9.

Example 9-12

Synthesis of (Z)-2-thioxo-5-(3,4,5-trimethoxybenzylidene)imidazolidin-4-one (Compound 109)

Light brown solid; a reaction time of 4 hours; a yield of 52.8%; a melting point of 264.0-266.6° C.; $^1$H NMR (500 MHz, DMSO-$d_6$) δ 12.25 (br s, 1H), 12.08 (br s, 1H), 7.54 (s, 2H), 6.52 (s, 1H), 3.79 (s, 6H), 3.69 (s, 3H); $^{13}$C NMR (100 MHz, DMSO-$d_6$) δ 175.9, 164.2, 153.1, 139.6, 130.1, 128.7, 120.3, 109.0, 60.8, 56.5;

Example 9-13

Synthesis of (Z)-5-(4-hydroxy-3,5-dimethoxybenzylidene)-2-thioxoimidazolidin-4-one (Compound 110)

Yellowish green solid; a reaction time of 4 hours; a yield of 84.6%; a melting point of 240.1-242.6° C.; $^1$H NMR (500 MHz, DMSO-$d_6$) δ 12.15 (br s, 1H), 11.98 (br s, 1H), 9.10 (br s, 1H), 7.57 (s, 2H), 6.50 (s, 1H), 3.76 (s, 6H); $^{13}$C NMR (100 MHz, DMSO-$d_6$) δ 174.9, 164.2, 148.1, 138.8, 128.5, 123.7, 121.9, 109.5, 56.6.

Example 10

Synthesis of Compounds 111 to 122

Table 10 below is provided to explain substitution patterns of Compounds 111 to 122, which are (Z)-5-(substituted benzylidene)-2-iminothiazolidin-4-one analogs.

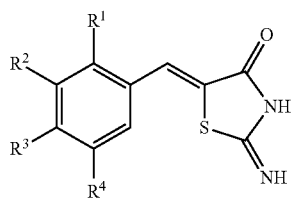

TABLE 10

| Compound | R¹ | R² | R³ | R⁴ |
|---|---|---|---|---|
| 111 | H | H | OH | H |
| 112 | H | OH | OH | H |
| 113 | H | OMe | OH | H |
| 114 | H | OEt | OH | H |
| 115 | H | OH | OMe | H |
| 116 | H | H | OMe | H |
| 117 | H | OMe | OMe | H |
| 118 | H | OH | H | OH |
| 119 | OMe | H | OMe | H |
| 120 | OH | H | H | H |
| 121 | H | OMe | OMe | OMe |
| 122 | H | OMe | OH | OMe |

OMe represents a methoxy group, and OEt represents an ethoxy group.

1) Synthesis of Compounds 111 to 117 and 120 to 122

Synthesis of Compounds 120 to 122, which are (Z)-5-(substituted benzylidene)-2-iminothiazolidin-4-one analogs, was performed as follows. In detail, in an acetic acid (4 mL/1 g sodium acetate) solvent, a mixture including a substituted benzaldhehyde (300 mg), pseudothiohydantin (1.1 eq.), and sodium acetate (3.0 eq.) was refluxed for 3 to 7 hours. After cooling, water was added thereto, and the produced precipitate was filtered, and in consideration of physical characteristics of the used starting materials, the resultant precipitate was washed with water and methylene chloride and/or ethyl acetate to obtain a solid target product.

2) Synthesis of (Z)-5-(3,5-dihydroxybenzylidene)-2-iminothiazolidin-4-one (Compound 118)

In an acetic acid (1.17 mL) solvent, a mixture including 3,5-dihydroxybenzaldehyde (200 mg, 1.20 mmol), pseudothiohydantin (154 mg, 1.32 mmol), and sodium acetate (296 mg, 3.61 mmol) was refluxed for 4 hours. After cooling, water was added thereto, and the produced precipitate was filtered and washed with water to obtain a solid Compound 118.

3) Synthesis of (Z)-5-(2,4-dimethoxybenzylidene)-2-iminothiazolidin-4-one (Compound 119)

In an ethyl alcohol (2 mL) and water (2 mL) solvent, a mixture including 2,4-dimethoxybenzaldehyde (300 mg, 1.81 mmol), pseudothiohydantin (231 mg, 1.99 mmol), and piperidine (0.18 mL, 1.80 mmol) was heated to a temperature of 80° C. for 7 hours. After cooling, water was added thereto, and the produced precipitate was filtered and washed with water, ethyl acetate, and methylene chloride to obtain a solid Compound 119.

Example 10-1

Synthesis of (Z)-5-(4-hydroxybenzylidene)-2-iminothiazolidin-4-one (Compound 111)

Orange solid; a reaction time of 3 hours; a yield of 61.8%; a melting point of >300° C.; $^1$H NMR (500 MHz, DMSO-$d_6$) δ 10.10 (s, 1H), 9.29 (br s, 1H), 9.04 (s, 1H), 7.49 (s, 1H), 7.40 (d, 2H, J=9.0 Hz), 6.88 (d, 2H, J=8.5 Hz); $^{13}$C NMR (100 MHz, DMSO-$d_6$) δ 181.4, 176.1, 159.6, 132.1, 130.2, 126.0, 125.5, 116.8; LRMS (ES) m/z 219 (M-H)⁻.

Example 10-2

Synthesis of (Z)-5-(3,4-dihydroxybenzylidene)-2-iminothiazolidin-4-one (Compound 112)

Brown solid; a reaction time of 6 hours; a yield of 62.0%; a melting point of >300° C.; $^1$H NMR (500 MHz, DMSO-$d_6$) δ 9.60 (br s, 1H), 9.33 (br s, 2H), 9.02 (s, 1H), 7.40 (s, 1H), 6.96 (s, 1H), 6.89 (d, 1H, J=8.5 Hz), 6.83 (d, 1H, J=8.5 Hz); $^{13}$C NMR (100 MHz, DMSO-$d_6$) δ 181.4, 176.2, 148.3, 146.4, 130.6, 126.0, 125.8, 123.5, 116.8, 116.6; LRMS (ES) m/z 235 (M-H)⁻.

Example 10-3

Synthesis of (Z)-5-(4-hydroxy-3-methoxybenzylidene)-2-iminothiazolidin-4-one (Compound 113)

Orange solid; a reaction time of 7 hours; a yield of 92.4%; a melting point of 263.9-265.6° C.; $^1$H NMR (400 MHz, DMSO-$d_6$) δ 9.69 (s, 1H), 9.27 (br s, 1H), 9.00 (s, 1H), 7.48 (s, 1H), 7.11 (d, 1H, J=2.0 Hz), 6.99 (dd, 1H, J=2.0, 8.4 Hz), 6.86 (d, 1H, J=8.4 Hz), 3.78 (s, 3H); $^{13}$C NMR (100 MHz, DMSO-$d_6$) δ 181.3, 176.0, 149.1, 148.6, 130.5, 126.2, 126.0, 123.9, 116.7, 114.1, 56.2; LRMS (ES) m/z 249 (M-H)⁻.

Example 10-4

Synthesis of (Z)-5-(3-ethoxy-4-hydroxybenzylidene)-2-iminothiazolidin-4-one (Compound 114)

Orange solid; a reaction time of 7 hours; a yield of 84.9%; a melting point of 248.8-251.2° C.; $^1$H NMR (500 MHz, DMSO-$d_6$) δ 9.63 (s, 1H), 9.28 (br s, 1H), 9.01 (s, 1H), 7.49 (s, 1H), 7.11 (s, 1H), 7.02 (d, 1H, J=8.5 Hz), 6.89 (s, 1H, J=8.0 Hz), 4.06 (q, 2H, J=7.0 Hz), 1.35 (t, 3H, J=7.0 Hz); $^{13}$C NMR (100 MHz, DMSO-$d_6$) δ 181.3, 176.0, 149.4, 147.7, 130.5, 126.1, 126.0, 124.1, 116.8, 115.1, 64.5, 15.3; LRMS (ES) m/z 263 (M-H)⁻.

Example 10-5

Synthesis of (Z)-5-(3-hydroxy-4-methoxybenzylidene)-2-iminothiazolidin-4-one (Compound 115)

Brown solid; a reaction time of 7 hours; a yield of 78.9%; a melting point of 282.8-285.7° C.; $^1$H NMR (500 MHz, DMSO-$d_6$) δ 9.38 (s, 1H), 9.30 (br s, 1H), 9.06 (s, 1H), 7.44 (s, 1H), 7.04 (dd, 1H, J=1.0, 8.5 Hz), 7.01 (d, 1H, J=8.5 Hz), 6.99 (d, 1H, J=1.0 Hz), 3.81 (s, 3H); $^{13}$C NMR (100 MHz, DMSO-$d_6$) δ 181.3, 176.2, 149.9, 147.5, 130.1, 127.4, 126.9, 123.1, 116.1, 113.0, 56.3; LRMS (ES) m/z 249 (M-H)⁻.

Example 10-6

Synthesis of (Z)-2-imino-5-(4-methoxybenzylidene)thiazolidin-4-one (Compound 116)

Yellow solid; a reaction time of 3 hours; a yield of 50.7%; a melting point of 285.9-288.5° C.; ¹H NMR (500 MHz, DMSO-$d_6$) δ 9.34 (br s, 1H), 9.09 (s, 1H), 7.53 (d, 2H, J=8.5 Hz), 7.51 (s, 1H), 7.07 (d, 2H, J=9.0 Hz), 3.80 (s, 3H); ¹³C NMR (100 MHz, DMSO-$d_6$) δ 181.3, 176.1, 160.9, 131.9, 129.7, 127.1, 127.1, 115.4, 56.1; LRMS (ES) m/z 233 (M-H)⁻.

Example 10-7

Synthesis of (Z)-5-(3,4-dimethoxybenzylidene)-2-iminothiazolidin-4-one (Compound 117)

Dark yellow solid; a reaction time of 6 hours; a yield of 82.4%; a melting point of 274.2-276.3° C.; ¹H NMR (400 MHz, DMSO-$d_6$) δ 9.32 (br s, 1H), 9.05 (s, 1H), 7.52 (s, 1H), 7.14 (d, 1H, J=2.0 Hz), 7.12 (dd, 1H, J=2.0, 8.4 Hz), 7.06 (d, 1H, J=8.4 Hz), 3.77 (s, 3H), 3.77 (s, 3H); ¹³C NMR (100 MHz, DMSO-$d_6$) δ 181.2, 176.0, 150.7, 149.5, 130.1, 127.4, 127.3, 123.5, 113.4, 112.7, 56.3, 56.1; LRMS (ES) m/z 263 (M-H)⁻.

Example 10-8

Synthesis of (Z)-5-(3,5-dihydroxybenzylidene)-2-iminothiazolidin-4-one (Compound 118)

Dark brown solid; a reaction time of 4 hours; a yield of 41.4%; a melting point of >300° C.; ¹H NMR (500 MHz, DMSO-$d_6$) δ 9.58 (s, 2H), 9.37 (br s, 1H), 9.13 (s, 1H), 7.35 (s, 1H), 6.42 (s, 2H), 6.27 (s, 1H); ¹³C NMR (100 MHz, DMSO-$d_6$) δ 181.1, 176.4, 159.5, 136.3, 130.3, 129.6, 108.2, 104.8; LRMS (ES) m/z 235 (M-H)⁻.

Example 10-9

Synthesis of (Z)-5-(2,4-dimethoxybenzylidene)-2-iminothiazolidin-4-one (Compound 119)

Yellow solid; a reaction time of 7 hours; a yield of 21.0%; a melting point of 249.1-250.7° C.; ¹H NMR (400 MHz, DMSO-$d_6$) δ 9.13 (br s, 2H), 7.75 (s, 1H), 7.32 (d, 1H, J=8.4 Hz), 6.66 (dd, 1H, J=2.0, 8.0 Hz), 6.62 (d, 1H, J=2.0 Hz), 3.84 (s, 3H), 3.79 (s, 3H); ¹³C NMR (100 MHz, DMSO-$d_6$) δ 181.0, 176.2, 162.8, 160.0, 129.8, 127.0, 124.2, 116.0, 106.8, 99.3, 56.5, 56.2; LRMS (ES) m/z 263 (M-H)⁻.

Example 10-10

Synthesis of (Z)-5-(2-hydroxybenzylidene)-2-iminothiazolidin-4-one (Compound 120)

Brown solid; a reaction time of 7 hours; a yield of 69.3%; a melting point of 210.1-211.5° C.; ¹H NMR (500 MHz, DMSO-$d_6$) δ 8.13 (s, 1H), 8.02-7.09 (br s, 3H), 7.72 (d, 1H, J=6.5 Hz), 7.57 (t, 1H, J=7.5 Hz), 7.43 (d, 1H, J=8.0 Hz), 7.32 (t, 1H, J=7.0 Hz); ¹³C NMR (100 MHz, DMSO-$d_6$) δ 180.3, 176.2, 159.2, 152.5, 137.8, 132.2, 128.5, 125.6, 119.9, 116.8; LRMS (ES) m/z 219 (M-H)⁻.

Examples 10-11

Synthesis of (Z)-2-imino-5-(3,4,5-trimethoxybenzylidene)thiazolidin-4-one (Compound 121)

Orange solid; a reaction time of 3 hours; a yield of 94.1%; a melting point of 253.3-254.8° C.; ¹H NMR (500 MHz, DMSO-$d_6$) δ 9.40 (br s, 1H), 9.11 (s, 1H), 7.55 (s, 1H), 6.91 (s, 2H), 3.82 (s, 6H), 3.70 (s, 3H); ¹³C NMR (100 MHz, DMSO-$d_6$) δ 181.0, 176.1, 153.8, 139.3, 130.3, 130.0, 129.1, 107.6, 60.8, 56.6; LRMS (ES) m/z 293 (M-H)⁻.

Example 10-12

Synthesis of (Z)-5-(4-hydroxy-3,5-dimethoxybenzylidene)-2-iminothiazolidin-4-one (Compound 122)

Dark orange solid; a reaction time of 6 hours; a yield of 87.7%; a melting point of 254.3-256.6° C.; ¹H NMR (400 MHz, DMSO-$d_6$) δ 9.30 (br s, 1H), 9.08 (s, 1H), 9.01 (s, 1H), 7.49 (s, 1H), 6.85 (s, 2H), 3.78 (s, 6H); ¹³C NMR (100 MHz, DMSO-$d_6$) δ 181.2, 176.0, 148.8, 138.3, 130.8, 126.5, 124.9, 108.0, 56.6; LRMS (ES) m/z 279 (M-H)⁻.

Example 11

Synthesis of Compounds 123 to 139

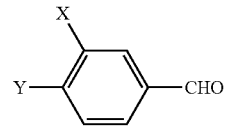

123a: X = OBn, Y = H
123b: X = H, Y = OBn

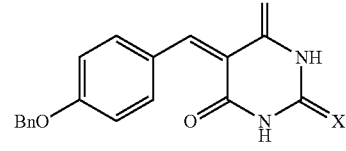

123: X = O; 124: X = S

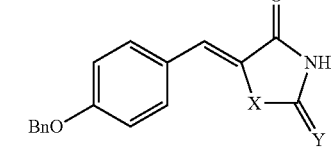

125: X = S, Y = O
126: X = NH, Y = O
127: X = CH₂, Y = O
128: X = S, Y = S
129: X = NCH₃, Y = NH
130: X = NH, Y = S
131: X = S, Y = NH

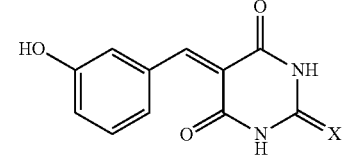

132: X = O; 133: X = S

-continued

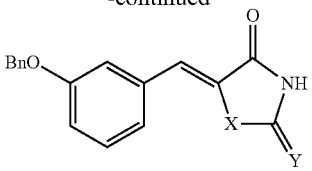

134: X = S, Y = O
135: X = NH, Y = O
136: X = CH₂, Y = O
137: X = S, Y = S
138: X = NH, Y = S
139: X = S, Y = NH

1) Synthesis of 3-(benzyloxy)benzaldehyde (Compound 123a)

In acetonitrile (50 mL) solvent, benzyl bromide (4.6 mL, 38.68 mmol) was added to a solution including 3-hydroxybenzaldehyde (5.0 g, 40.94 mmol) and potassium carbonate (8.49 g, 61.43 mmol), and the reaction mixture was refluxed for 3 hours. After cooling, the reaction mixture was distributed between methylene chloride and water. An organic layer was dried by using MgSO₄ and filtered. The filtrate was evaporated, and water was added to the resultant solid. The solid was filtered and washed with water to obtain Compound 123a (8.53 g, 98%).
$^1$H NMR (500 MHz, DMSO-$d_6$) δ 9.97 (s, 1H), 7.54-7.51 (m, 3H), 7.47 (d, 2H, J=7.5 Hz), 7.40 (t, 2H, J=7.0 Hz), 7.37-7.32 (m, 2H), 5.19 (s, 2H); $^{13}$C NMR (100 MHz, DMSO-$d_6$) δ 193.6, 159.5, 138.3, 137.3, 131.1, 129.1, 128.6, 128.4, 123.4, 122.4, 114.6, 70.1.

2) Synthesis of 4-(benzyloxy)benzaldehyde (Compound 123b)

In an acetonitrile (30 mL) solvent, benzyl bromide (1.95 mL, 16.40 mmol) was added to a solution including 4-hydroxybenzaldehyde (2.0 g, 16.38 mmol) and potassium carbonate (3.40 g, 24.60 mmol), and the reaction mixture was refluxed for 1.5 hours. After cooling, the reaction mixture was distributed between methylene chloride and water. An organic layer was dried by using MgSO₄ and filtered. The filtrate was evaporated, and the resultant solid was added to water. The solid was filtered and washed with water to obtain Compound 123b (3.082 g, 88.7%).
$^1$H NMR (400 MHz, CDCl₃) δ 9.87 (s, 1H), 7.82 (d, 2H, J=9.2 Hz), 7.43-7.34 (m, 5H), 7.06 (d, 2H, J=8.8 Hz), 5.14 (s, 2H); $^{13}$C NMR (100 MHz, CDCl₃) δ 191.0, 164.0, 136.1, 132.2, 130.3, 129.0, 128.6, 127.7, 115.4, 70.5.

3) Synthesis of Compounds 123, 124, 132, and 133, which are Barbituric Acid and Thiobarbituric Acid Analogs In a solution including ethanol and water (1:1), 4-(benzyloxy)benzaldehyde (123b, 1.0 eq.) and a barbituric acid (1.1 eq.) or a thiobarbituric acid (1.1 eq.) was heated to a temperature of 80° C. After cooling, water was added to the reaction mixture. The produced precipitate was filtered, and then washed with water and ethyl acetate to obtain solid Compounds 123 and 124.
In a solution including ethanol and water (1:1), a solution including 3-(benzyloxy)benzaldhehyde (123a, 1.0 eq.) and a barbituric acid (1.1 eq.) or a thiobarbituric acid (1.1 eq.) was heated to a temperature of 80° C. The produced precipitate was filtered, and then washed with water and ethyl acetate to obtain solid Compounds 132 and 133.

4) Synthesis of Compounds 127 and 136, which are (E)-((benzyloxy)benzylidene)pyrrolidin-2,5-dione analogs In a methanol solvent, a solution including 3-(benzyloxy)benzaldhehyde (Compound 123a, 1.0 eq.) or 4-(benzyloxy)benzaldehyde (Compound 123b, 1.0 eq.) and triphenylphosphoranylidene succinimide (Compound 36a, 1.0 eq.) was refluxed. After cooling, the produced precipitate was filtered, and then washed with water and methanol to obtain solid Compounds 127 and 136.

5) Synthesis of Compounds 125, 128, 130, 131, 134, 137, 138 and 139

In an acetic acid (AcOH) (1.53 mL/10 eq. of sodium acetate) solvent, a solution including sodium acetate (3.0 to 10.0 eq.), 3-(benzyloxy)benzaldhehyde Compound 123a, 1.0 eq., used for the synthesis of 3-(benzyloxy)benzylidene analogue) or 4-(benzyloxy)benzaldehyde (Compound 123b, 1.0 eq., used for the synthesis of 4-(benzyloxy)benzylidene analogue) and rhodanine (1.1 eq., used for the synthesis of Compounds 128 and 137), 2,4-thiazolidinedione (1.1 eq., used for the synthesis of Compounds 125 and 134), 2-thiohydantoin (1.1 eq., used for the synthesis of Compounds 130 and 138), or pseudothiohydantoin (1.1 eq., used for the synthesis of Compounds 131 and 139) was refluxed. After cooling, water was added thereto. The produced precipitate was filtered and washed with water and a co-solvent of hexane and ethyl acetate (1:1) to obtain a solid target compound.

6) Synthesis of Compounds 126, 129, and 135

In a co-solvent of ethyl alcohol and water (4:1), a solution including 3-(benzyloxy)benzaldhehyde (Compound 123a, 1.0 eq., used for the synthesis of Compound 135) or 4-(benzyloxy)benzaldehyde (Compound 123b, 1.0 eq., used for the synthesis of Compounds 126 and 129), hydantoin (1.1-1.2 eq.) or creatinine (1.1 eq.) and piperidine (1.0 eq.) was refluxed. After cooling, water was added thereto. The produced precipitate was filtered and washed with water and a co-solvent of hexane and ethyl acetate (1:1) to obtain a solid target compound.

Example 11-1

Synthesis of 5-(4-(benzyloxy)benzylidene)pyrimidine-2,4,6(1H,3H,5H)-trione (Compound 123)

A reaction time of 6 hours; a yield of 95%; $^1$H NMR (500 MHz, DMSO-$d_6$) δ 11.29 (s, 1H), 11.16 (s, 1H), 8.35 (d, 2H, J=9.0 Hz), 8.24 (s, 1H), 7.46 (d, 2H, J=7.5 Hz), 7.40 (t, 2H, J=7.5 Hz), 7.34 (t, 1H, J=7.5 Hz), 7.13 (d, 2H, J=9.0 Hz), 5.23 (s, 2H); $^{13}$C NMR (100 MHz, DMSO-$d_6$) δ 164.5, 163.2, 162.8, 155.5, 150.9, 138.1, 137.0, 129.2, 128.8, 128.5, 126.0, 116.3, 115.3, 70.3.

Example 11-2

Synthesis of 5-(4-(benzyloxy)benzylidene)-2-thioxodihydropyrimidine-4,6(1H,5H)-dione (Compound 124)

A reaction time of 2 hours; a yield of 98.1%; $^1$H NMR (500 MHz, DMSO-$d_6$) δ 12.37 (s, 1H), 12.27 (s, 1H), 8.40 (d, 2H, J=9.0 Hz), 8.25 (s, 1H), 7.47 (d, 2H, J=7.5 Hz), 7.40 (t, 2H, J=8.0 Hz), 7.34 (t, 1H, J=7.5 Hz), 7.15 (d, 2H, J=9.0 Hz), 5.25 (s, 2H); $^{13}$C NMR (100 MHz, DMSO-$d_6$) δ 179.0, 163.7, 162.9, 160.6, 156.6, 138.5, 136.9, 129.2, 128.8, 128.6, 126.1, 116.4, 115.5, 70.4.

Example 11-3

Synthesis of (Z)-5-(4-(benzyloxy)benzylidene)thiazolidine-2,4-dione (Compound 125)

A reaction time of 36 hours; a yield of 82.7%; $^1$H NMR (500 MHz, DMSO-$d_6$) δ 12.51 (br s, 1H), 7.74 (s, 1H), 7.55 (d, 2H, J=8.5 Hz), 7.45 (d, 2H, J=7.0 Hz), 7.39 (t, 2H, J=7.0 Hz), 7.34 (t, 1H, J=7.0 Hz), 7.17 (d, 2H, J=8.5 Hz), 5.18 (s, 2H); $^{13}$C NMR (100 MHz, DMSO-$d_6$) δ 168.6, 168.1, 160.7, 137.2, 132.7, 132.4, 129.2, 128.7, 128.5, 126.4, 121.1, 116.4, 70.2.

Example 11-4

Synthesis of (Z)-5-(4-(benzyloxy)benzylidene)imidazolidine-2,4-dione (Compound 126)

A reaction time of 14 hours; a yield of 42.9%; $^1$H NMR (500 MHz, DMSO-$d_6$) δ 11.14 (br s, 1H), 10.41 (br s, 1H), 7.57 (d, 2H, J=8.5 Hz), 7.44 (d, 2H, J=7.5 Hz), 7.38 (t, 2H, J=8.0 Hz), 7.32 (t, 1H, J=7.5 Hz), 7.02 (d, 2H, J=9.0 Hz), 6.37 (s, 1H), 5.14 (s, 2H); $^{13}$C NMR (100 MHz, DMSO-$d_6$) δ 166.3, 159.2, 156.3, 137.5, 131.7, 129.1, 128.6, 128.4, 126.8, 126.3, 115.8, 109.2, 69.9.

Example 11-5

Synthesis of (E)-3-(4-(benzyloxy)benzylidene)pyrrolidine-2,5-dione (Compound 127)

A reaction time of 3 hours; a yield of 85.7%; $^1$H NMR (400 MHz, DMSO-$d_6$) δ 11.31 (s, 1H), 7.53 (d, 2H, J=9.2 Hz), 7.42 (d, 2H, J=7.2 Hz), 7.36 (t, 2H, J=7.2 Hz), 7.30 (t, 1H, J=7.2 Hz), 7.29 (t, 1H, J=2.0 Hz), 7.06 (d, 2H, J=8.8 Hz), 5.14 (s, 2H), 3.56 (d, 2H, J=2.0 Hz); $^{13}$C NMR (100 MHz, DMSO-$d_6$) δ 176.5, 172.8, 160.2, 137.4, 132.7, 132.0, 129.1, 128.6, 128.4, 127.7, 124.9, 116.0, 70.0, 35.4.

Example 11-6

Synthesis of (Z)-5-(4-(benzyloxy)benzylidene)-2-thioxothiazolidin-4-one (Compound 128)

A reaction time of 10 hours; a yield of 75.9%; $^1$H NMR (400 MHz, DMSO-$d_6$) δ 7.57 (s, 1H), 7.53 (d, 2H, J=8.8 Hz), 7.42 (d, 2H, J=7.6 Hz), 7.36 (t, 2H, J=7.2 Hz), 7.30 (t, 1H, J=7.2 Hz), 7.15 (d, 2H, J=8.8 Hz), 5.16 (s, 2H); $^{13}$C NMR (100 MHz, DMSO-$d_6$) δ 196.2, 170.2, 161.1, 137.1, 133.4, 132.5, 129.2, 128.7, 128.5, 126.3, 123.1, 116.6, 70.2.

Example 11-7

Synthesis of (E/Z)-5-(4-(benzyloxy)benzylidene)-2-imino-1-methylimidazolidin-4-one (Compound 129)

A reaction time of 48 hours; a yield of 26.9%; $^1$H NMR (400 MHz, DMSO-$d_6$) δ 9.83 (s, 1H), 8.13 (d, 2H, J=8.8 Hz), 7.83 (d, 2H, J=8.8 Hz), 7.44-7.27 (m, 10H), 7.17 (d, 2H, J=8.8 Hz), 6.94 (d, 2H, J=9.2 Hz), 6.40 (s, 1H), 6.14 (s, 1H), 5.19 (s, 2H), 5.09 (s, 2H), 3.12 (s, 3H), 2.91 (s, 3H).

Example 11-8

Synthesis of (Z)-5-(4-(benzyloxy)benzylidene)-2-thioxoimidazolidin-4-one (Compound 130)

A reaction time of 9 hours; a yield of 85.6%; $^1$H NMR (500 MHz, DMSO-$d_6$) δ 12.28 (s, 1H), 12.04 (s, 1H), 7.72 (d, 2H, J=9.0 Hz), 7.45 (d, 2H, J=8.0 Hz), 7.39 (t, 2H, J=7.5 Hz), 7.33 (t, 1H, J=7.0 Hz), 7.05 (d, 2H, J=8.5 Hz), 6.45 (s, 1H), 5.17 (s, 2H); $^{13}$C NMR (100 MHz, DMSO-$d_6$) δ 179.3, 166.5, 160.0, 137.4, 132.8, 129.1, 128.6, 128.4, 126.6, 125.7, 115.9, 112.7, 70.0.

Example 11-9

Synthesis of (Z)-5-(4-(benzyloxy)benzylidene)-2-iminothiazolidin-4-one (Compound 131)

A reaction time of 9 hours; a yield of 80.1%; $^1$H NMR (500 MHz, DMSO-$d_6$) δ 9.33 (br s, 1H), 9.08 (s, 1H), 7.54 (s, 1H), 7.51 (d, 2H, J=9.0 Hz), 7.45 (d, 2H, J=7.5 Hz), 7.39 (t, 2H, J=7.5 Hz), 7.33 (t, 1H, J=7.0 Hz), 7.15 (d, 2H, J=8.5 Hz), 5.16 (s, 2H); $^{13}$C NMR (100 MHz, DMSO-$d_6$) δ 181.2, 176.1, 160.0, 137.3, 131.9, 129.6, 129.2, 128.6, 128.5, 127.3, 127.3, 116.2, 70.1.

Example 11-10

Synthesis of 5-(3-(benzyloxy)benzylidene)pyrimidine-2,4,6(1H,3H,5H)-trione (Compound 132)

A reaction time of 5 minutes; a yield of 54.3%; $^1$H NMR (500 MHz, DMSO-$d_6$) δ 11.38 (s, 1H), 11.23 (s, 1H), 8.24 (s, 1H), 7.90 (s, 1H), 7.62 (d, 1H, J=7.5 Hz), 7.45 (d, 2H, J=7.5 Hz), 7.40-7.36 (m, 3H), 7.33 (t, 1H, J=7.0 Hz), 7.19 (brd, 1H, J=7.5 Hz), 5.13 (s, 2H); $^{13}$C NMR (100 MHz, DMSO-$d_6$) δ 164.1, 162.3, 158.4, 155.0, 150.9, 137.4, 134.5, 129.8, 129.2, 128.6, 128.5, 126.9, 120.0, 119.8, 119.3, 70.0.

Example 11-11

Synthesis of 5-(3-(benzyloxy)benzylidene)-2-thioxodihydropyrimidine-4,6(1H,5H)-dione (Compound 133)

A reaction time of 4 hours; a yield of 51.9%; $^1$H NMR (400 MHz, DMSO-$d_6$) δ 12.44 (s, 1H), 12.33 (s, 1H), 8.22 (s, 1H), 7.93 (s, 1H), 7.65 (d, 1H, J=7.2 Hz), 7.43 (d, 2H, J=7.6 Hz), 7.39-7.30 (m, 3H), 7.26 (t, 1H, J=7.6 Hz), 7.19 (dd, 1H, J=2.0, 8.0 Hz), 5.11 (s, 2H).

Example 11-12

Synthesis of (Z)-5-(3-(benzyloxy)benzylidene)thiazolidine-2,4-dione (Compound 134)

A reaction time of 10 hours; a yield of 50.9%; $^1$H NMR (400 MHz, DMSO-$d_6$) δ 7.71 (s, 1H), 7.43-7.39 (m, 3H), 7.36 (t, 2H, J=7.2 Hz), 7.30 (t, 1H, J=6.8 Hz), 7.18 (brs, 1H), 7.14-7.09 (m, 2H), 5.13 (s, 2H); $^{13}$C NMR (100 MHz, DMSO-$d_6$) δ 168.5, 168.0, 159.4, 137.4, 135.1, 132.3, 131.1, 129.1, 128.6, 128.4, 124.7, 122.9, 117.9, 116.7, 70.0.

Examples 11 to 13

Synthesis of (Z)-5-(3-(benzyloxy)benzylidene)imidazolidine-2,4-dione (Compound 135)

A reaction time of 48 hours; a yield of 32%; $^1$H NMR (400 MHz, DMSO-$d_6$) δ 11.21 (br s, 1H), 10.68 (br s, 1H), 7.43 (d, 2H, J=7.6 Hz), 7.36 (t, 2H, J=7.6 Hz), 7.30 (t, 1H, J=7.6 Hz), 7.27 (t, 1H, J=8.0 Hz), 7.20 (d, 1H, J=1.6 Hz), 7.16 (d, 1H, J=8.0 Hz), 6.94 (dd, 1H, J=1.6, 8.0 Hz), 6.34 (s, 1H), 5.13 (s, 2H); $^{13}$C NMR (100 MHz, DMSO-$d_6$) δ 166.2, 159.3, 156.4, 137.7, 135.0, 130.5, 129.1, 128.8, 128.5, 128.4, 122.9, 115.9, 115.8, 108.9, 69.9.

Examples 11 to 14

Synthesis of (E)-3-(3-(Benzyloxy)benzylidene)pyrrolidine-2,5-dione (Compound 136)

A reaction time of 3 hours; a yield of 55%; $^1$H NMR (400 MHz, DMSO-$d_6$) δ 11.41 (s, 1H), 7.43 (d, 2H, J=7.6 Hz), 7.38-7.34 (m, 3H), 7.33-7.28 (m, 2H), 7.18 (s, 1H), 7.16 (d, 1H, J=7.6 Hz), 7.04 (d, 1H, J=8.0 Hz), 5.13 (s, 2H), 3.59 (s, 2H); $^{13}$C NMR (100 MHz, DMSO-$d_6$) δ 176.4, 172.6, 159.2, 137.6, 136.2, 132.1, 130.7, 129.1, 128.6, 128.4, 128.0, 123.4, 117.2, 116.6, 69.9, 35.4.

Examples 11 to 15

Synthesis of (Z)-5-(3-(benzyloxy)benzylidene)-2-thioxothiazolidin-4-one (Compound 137)

A reaction time of 2 hours; a yield of 56.3%; $^1$H NMR (400 MHz, DMSO-$d_6$) δ 7.57 (s, 1H), 7.44 (m, 3H), 7.36 (t, 2H, J=7.2 Hz), 7.30 (t, 1H, J=7.2 Hz), 7.18 (d, 1H, J=1.6 Hz), 7.13-7.11 (m, 2H), 5.13 (s, 2H); $^{13}$C NMR (100 MHz, DMSO-$d_6$) δ 196.4, 170.0, 159.4, 137.3, 135.0, 132.2, 131.3, 129.2, 128.6, 128.4, 126.6, 123.4, 118.3, 117.1, 70.1.

Example 11-16

Synthesis of (Z)-5-(3-(benzyloxy)benzylidene)-2-thioximidazolidin-4-one (Compound 138)

A reaction time of 4 hours; a yield of 57.4%; $^1$H NMR (500 MHz, DMSO-$d_6$) δ 12.37 (s, 1H), 12.18 (s, 1H), 7.46 (d, 2H, J=7.5 Hz), 7.39 (t, 2H, J=7.5 Hz), 7.35-7.31 (m, 4H), 7.02 (brd, 1H, J=8.0 Hz), 6.44 (s, 1H), 5.16 (s, 2H); $^{13}$C NMR (100 MHz, DMSO-$d_6$) δ 180.0, 166.5, 159.2, 137.6, 134.3, 130.6, 129.1, 128.6, 128.5, 128.5, 123.7, 116.7, 116.6, 112.2, 70.0;

Examples 11 to 17

Synthesis of (Z)-5-(3-(Benzyloxy)benzylidene)-2-iminothiazolidin-4-one (Compound 139)

A reaction time of 3 hours; a yield of 43.2%; $^1$H NMR (400 MHz, DMSO-$d_6$) δ 9.42 (s, 1H), 9.13 (s, 1H), 7.53 (s, 1H), 7.43 (d, 2H, J=7.6 Hz), 7.41-7.35 (m, 3H), 7.30 (t, 1H, J=7.6 Hz), 7.19 (d, 1H, J=1.6 Hz), 7.12 (d, 1H, J=8.0 Hz), 7.05 (dd, 1H, J=1.6, 8.4 Hz), 5.12 (s, 2H); $^{13}$C NMR (100 MHz, DMSO-$d_6$) δ 180.9, 176.2, 159.4, 137.4, 136.2, 131.0, 130.4, 129.6, 129.2, 128.6, 128.5, 122.4, 116.9, 116.3, 70.0.

Example 12

Synthesis of Compounds 140 to 150

Table 11 below is provided to explain substitution patterns of Compounds 140 to 150, which are (Z)-4-(substituted benzylidene)-2-phenyloxazol-5(4H)-one analogs.

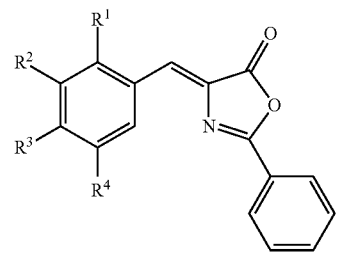

TABLE 11

| Compound | R$^1$ | R$^2$ | R$^3$ | R$^4$ |
| --- | --- | --- | --- | --- |
| 140 | H | H | AcO | H |
| 141 | H | AcO | AcO | H |
| 142 | OH | H | AcO | H |
| 143 | H | OMe | AcO | H |
| 144 | H | OEt | AcO | H |
| 145 | H | AcO | OMe | H |
| 146 | H | H | OMe | H |
| 147 | H | OMe | OMe | H |
| 148 | H | OMe | OMe | OMe |
| 149 | OMe | H | OMe | H |
| 150 | H | OMe | AcO | OMe |

OMe represents a methoxy group, OEt represents an ethoxy group, and AcO represents an acetate group.

Synthesis of Compounds 140 to 150, which are (Z)-4-(substituted benzylidene)-2-phenyloxazol-5(4H)-one analogs, was performed as follows. In detail, acetic anhydride (1.5 eq.+additional 1.0 eq.×the number of hydroxyl groups of benzaldhehyde) solvent, a solution including substituted benzaldhehyde (1.0 eq.), a hippuric acid (1.1 eq.), and a sodium acetate (1.0 eq.) was heated to a temperature of 60° C. (in the case of Compounds 140, 141, 143, 144, 146 and 150) or was refluxed (in the case of Compounds 142, 145, 147, 148, and 149). After cooling, methanol and water were added thereto. The produced precipitate was filtered, and then washed with water and methanol to obtain a target compound.

Example 12-1

Synthesis of (Z)-4-((5-oxo-2-phenyloxazol-4(5H)-ylidene)methyl)phenyl acetate (Compound 140)

A reaction time of 10 minutes; a yield of 63.9%; $^1$H NMR (500 MHz, CDCl$_3$) δ 8.24 (d, 2H, J=8.5 Hz), 8.18 (d, 2H, J=8.0 Hz), 7.63 (t, 1H, J=7.5 Hz), 7.54 (t, 2H, J=7.5 Hz), 7.23 (d, 2H, J=8.0 Hz), 7.22 (s, 1H), 2.34 (s, 3H); $^{13}$C NMR (100 MHz, CDCl$_3$) δ 169.2, 167.8, 163.9, 152.9, 134.0, 133.7, 133.4, 131.4, 130.7, 129.2, 128.6, 125.7, 122.4, 21.5.

Example 12-2

Synthesis of (Z)-4-((5-oxo-2-phenyloxazol-4(5H)-ylidene)methyl)-1,2-phenylene diacetate (Compound 141)

A reaction time of 10 minutes; a yield of 37.5%; $^1$H NMR (400 MHz, CDCl$_3$) δ 8.13 (d, 2H, J=7.2 Hz), 8.11 (d, 1H, J=1.6 Hz), 8.00 (d, 1H, J=1.6, 8.4 Hz), 7.59 (t, 1H, J=7.6 Hz), 7.50 (t, 2H, J=7.6 Hz), 7.29 (d, 1H, J=8.4 Hz), 7.13 (s, 1H), 2.33 (s, 3H), 2.30 (s, 3H); $^{13}$C NMR (100 MHz, CDCl$_3$) δ 168.3, 168.1, 167.5, 164.3, 144.4, 142.5, 134.1, 133.8, 132.4, 131.1, 129.7, 129.2, 128.7, 127.1, 125.6, 124.1, 21.0, 20.9.

Example 12-3

Synthesis of (Z)-3-hydroxy-4-((5-oxo-2-phenyloxazol-4(5H)-ylidene)methyl)phenyl acetate (Compound 142)

A reaction time of 6 hours; a yield of 15.0%; $^1$H NMR (500 MHz, CDCl$_3$) δ 8.87 (s, 1H), 8.81 (s, 1H), 7.93 (d, 2H, J=8.0 Hz), 7.60 (t, 1H, J=7.5 Hz), 7.56 (d, 1H, J=8.5 Hz), 7.53 (t, 2H, J=7.5 Hz), 7.16 (d, 1H, J=2.0 Hz), 7.10 (dd, 1H, J=2.5, 8.5 Hz), 2.35 (s, 3H); $^{13}$C NMR (100 MHz, CDCl$_3$) δ 169.1, 166.4, 159.0, 151.7, 150.4, 133.6, 132.9, 129.2, 128.7, 127.4, 124.0, 123.2, 119.4, 117.9, 110.3, 21.4.

Example 12-4

Synthesis of (Z)-2-methoxy-4-((5-oxo-2-phenyloxazol-4(5H)-ylidene)methyl)phenyl acetate (Compound 143)

A reaction time of 10 minutes; a yield of 46.4%; $^1$H NMR (400 MHz, CDCl$_3$) δ 8.10 (s, 1H), 8.09 (d, 2H, J=8.4 Hz), 7.59-7.56 (m, 2H), 7.50 (t, 2H, J=7.2 Hz), 7.15 (s, 1H), 7.10 (d, 1H, J=8.0 Hz), 3.93 (s, 3H), 2.33 (s, 3H); $^{13}$C NMR (100 MHz, CDCl$_3$) δ 168.9, 167.7, 163.8, 151.5, 142.4, 133.7, 133.3, 132.6, 131.1, 129.2, 128.5, 126.3, 125.7, 123.4, 115.6, 56.1, 20.9.

Example 12-5

Synthesis of (Z)-2-ethoxy-4-((5-oxo-2-phenyloxazol-4(5H)-ylidene)methyl)phenyl acetate (Compound 144)

A reaction time of 10 minutes; a yield of 24.8%; $^1$H NMR (400 MHz, CDCl$_3$) δ 8.11 (d, 2H, J=7.6 Hz), 8.05 (s, 1H), 7.60 (d, 1H, J=7.2 Hz), 7.59 (t, 1H, J=7.2 Hz), 7.51 (t, 2H, J=7.2 Hz), 7.16 (s, 1H), 7.10 (d, 1H, J=8.0 Hz), 4.17 (q, 2H, J=6.8 Hz), 2.32 (s, 3H), 1.46 (t, 3H, J=6.8 Hz); $^{13}$C NMR (100 MHz, CDCl$_3$) δ 168.9, 167.7, 163.7, 150.9, 142.7, 133.6, 133.3, 132.5, 131.3, 129.2, 128.5, 126.2, 125.7, 123.3, 116.6, 64.6, 20.9, 14.9.

Example 12-6

Synthesis of (Z)-2-Methoxy-5-((5-oxo-2-phenyloxazol-4(5H)-ylidene)methyl)phenyl acetate (Compound 145)

A reaction time of 3 hours; a yield of 55.2%; $^1$H NMR (400 MHz, CDCl$_3$) δ 8.13 (d, 2H, J=7.2 Hz), 8.06 (s, 1H), 7.93 (d, 1H, J=8.4 Hz), 7.57 (t, 1H, J=7.6 Hz), 7.50 (t, 2H, J=7.6 Hz), 7.13 (s, 1H), 7.01 (d, 1H, J=8.8 Hz), 3.88 (s, 3H), 2.35 (s, 3H); $^{13}$C NMR (100 MHz, CDCl$_3$) δ 169.0, 167.9, 163.1, 153.9, 140.2, 133.4, 132.7, 132.1, 131.0, 129.1, 128.5, 127.0, 126.6, 125.9, 112.4, 56.3, 20.9.

Example 12-7

Synthesis of (Z)-4-(4-methoxybenzylidene)-2-phenyloxazol-5(4H)-one (Compound 146)

A reaction time of 10 minutes; a yield of 27.7%; $^1$H NMR (500 MHz, CDCl$_3$) δ 8.19 (d, 2H, J=8.5 Hz), 8.17 (d, 2H, J=8.5 Hz), 7.60 (t, 1H, J=7.5 Hz), 7.52 (t, 2H, J=7.5 Hz), 7.22 (s, 1H), 7.00 (d, 2H, J=8.0 Hz), 3.89 (s, 3H); $^{13}$C NMR (100 MHz, CDCl$_3$) δ 168.2, 162.7, 162.4, 134.8, 133.2, 132.1, 131.3, 129.1, 128.4, 126.8, 126.0, 114.7, 55.7.

Example 12-8

Synthesis of (Z)-4-(3,4-dimethoxybenzylidene)-2-phenyloxazol-5(4H)-one (Compound 147)

A reaction time of 3 hours; a yield of 55.3%; $^1$H NMR (400 MHz, CDCl$_3$) δ 8.15 (d, 1H, J=2.0 Hz), 8.10 (d, 2H, J=8.8 Hz), 7.58 (t, 1H, J=7.2 Hz), 7.54 (dd, 1H, J=2.0, 8.4 Hz), 7.50 (t, 2H, J=7.2 Hz), 7.18 (s, 1H), 6.92 (d, 1H, J=8.4 Hz), 4.01 (s, 3H), 3.94 (s, 3H); $^{13}$C NMR (100 MHz, CDCl$_3$) δ 168.1, 162.6, 152.3, 149.4, 133.3, 132.3, 131.4, 129.2, 128.2, 128.0, 127.1, 126.0, 114.1, 111.1, 56.2, 56.1.

Example 12-9

Synthesis of (Z)-2-phenyl-4-(3,4,5-trimethoxybenzylidene)oxazol-5(4H)-one (Compound 148)

A reaction time of 3 hours; a yield of 65.4%; $^1$H NMR (400 MHz, CDCl$_3$) δ 8.08 (d, 2H), J=8.4 Hz), 7.59 (t, 1H, J=7.6 Hz), 7.51 (s, 2H), 7.50 (t, 2H, J=7.6 Hz), 7.13 (s, 1H), 3.94 (s, 6H), 3.93 (s, 3H); $^{13}$C NMR (100 MHz, CDCl$_3$) δ 167.8, 163.3, 153.4, 141.3, 133.5, 132.5, 131.9, 129.2, 129.1, 128.3, 125.8, 109.9, 61.3, 56.4.

Example 12-10

Synthesis of (Z)-4-(2,4-dimethoxybenzylidene)-2-phenyloxazol-5(4H)-one (Compound 149)

A reaction time of 3 hours; a yield of 65.6%; $^1$H NMR (400 MHz, CDCl$_3$) δ 8.87 (d, 1H, J=8.8 Hz), 8.13 (d, 2H, J=8.4 Hz), 7.78 (s, 1H), 7.55 (t, 1H, J=7.6 Hz), 7.49 (t, 2H, J=7.6 Hz), 6.63 (dd, 1H, J=2.4, 9.2 Hz), 6.42 (d, 1H, J=2.4 Hz), 3.87 (s, 6H); $^{13}$C NMR (100 MHz, CDCl$_3$) δ 168.5, 164.3, 162.1, 161.3, 134.8, 132.9, 130.3, 129.0, 128.2, 126.4, 126.3, 116.3, 106.5, 97.9, 55.9, 55.8.

Example 12-11

Synthesis of (Z)-2,6-dimethoxy-4-((5-oxo-2-phenyloxazol-4(5H)-ylidene)methyl)phenyl acetate (Compound 150)

A reaction time of 10 minutes; a yield of 21.9%; $^1$H NMR (400 MHz, CDCl$_3$) δ 8.04 (d, 2H, J=7.6 Hz), 7.58 (t, 1H, J=7.2 Hz), 7.50 (s, 2H), 7.48 (t, 2H, J=8.0 Hz), 7.08 (s, 1H), 3.89 (s, 6H), 2.35 (s, 3H); $^{13}$C NMR (100 MHz, CDCl$_3$) δ

168.6, 167.6, 163.7, 152.5, 133.7, 133.4, 131.8, 131.4, 129.2, 128.4, 125.7, 109.3, 56.4, 20.7.

Example 13

Synthesis of (Z)-5-(4-hydroxy-3,5-dimethoxybenzylidene)imidazolidine-2,4-dione (Compound 151)

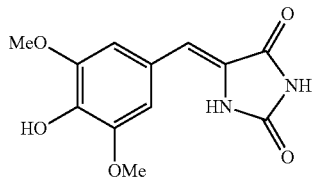

In an acetic acid (1.6 mL) solvent, a suspension including syringaldehyde (300 mg, 1.65 mmol), hydantoin (198 mg, 1.98 mmol), and sodium acetate (405 mg, 4.94 mmol) was refluxed for 24 hours, and after cooling, the produced precipitate was filtered. The filtered solid was washed with methylene chloride and a small amount of water. After drying under reduced pressure, a target compound was obtained (192.9 mg, 44.3%).

Yellow solid; a reaction time of 24 hours; a yield of 44.3%; a melting point of 266.0-268.5° C.; $^1$H NMR (500 MHz, DMSO-$d_6$) δ 11.13 (s, 1H), 10.50 (s, 1H), 8.81 (s, 1H), 6.82 (s, 2H), 6.35 (s, 1H), 3.81 (s, 6H); $^{13}$C NMR (100 MHz, DMSO-$d_6$) δ 166.3, 156.5, 148.7, 137.4, 126.2, 123.8, 110.8, 108.0, 56.8; LRMS (ES) m/z 263 (M-H)$^-$.

Experimental Example 1

In Vitro ROS Scavenging Activity Assay

1. Preparation of Vascular Endothelial Cells (YPEN-1)

YPEN-1 cells (rat prostatic endothelial cell line) was obtained from American type culture collection (ATCC, Manassas, Va., USA), and the cells were cultured by using a dulbecco's modified eagle medium (DMEM, Nissui, Tokyo, Japan) containing 2 mM L-glutamine, 100 mg/ml streptomycin, 2.5 mg/L amphotericin B, and 5% inactivated fetal bovine serum (FBS). Also, the cells were maintained at a temperature of 37° C. in a humid atmosphere-like condition containing 5% $CO_2$ and 95% air. Also, a medium that did not contain 5% FBS was used as a serum-free medium (SFM). The cells were sub-cultured in 100 mm plastic flask (Corning Co., New York, USA) every two days to maintain the cell line.

2. 2. ROS Measurement

2',7'-dichlorodihydrofluorescein diacetate (DCFDA) assay method according to a conventionally known method (Chem Res Toxicol. 5: 227-231, 1992) was used. In detail, 12.5 mM DCFDA dissolved in 99.9% ethanol and 600 U/ml esterase dissolved in tertiary distilled water were stored as a stock solution at a temperature of −20° C., and a 2',7'-dichlorodihydrofluorescein (DCFH) solution prepared by mixing 10 mM DCFDA and 6 U/ml esterase was cultured at a temperature of 22° C. for 20 minutes, and then, refrigerated in a dark place before use. Since the oil-soluble DCFDA was deacetylated into non-fluorescent DCFH due to esterase or oxidative hydrolysis and the DCFH was oxidized due to activityoxygen to produce highly-fluorescent 2',7'-dichlorofluorescein (DCF), the present measurement was performed at an excitation wavelength of 485 nm and an emission wavelength of 530 nm by using a fluorophotometer (GENios, TECAN). Vascular endothelial cells that were pre-treated with 50 μM 3-morpholinosydnonimine hydrochloride (SIN-1) for 1 hour were used as a reactive oxygen generation source.

Figure 2:
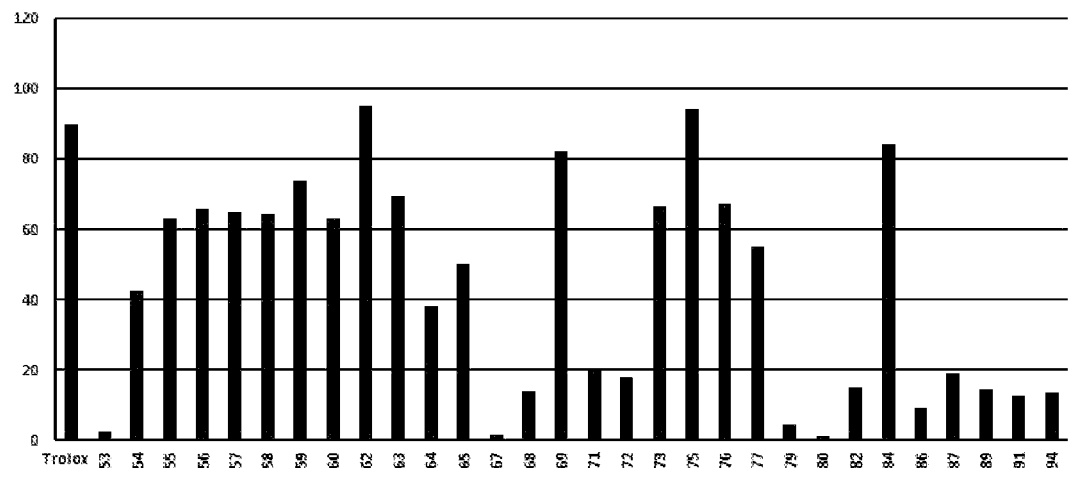
Figure 3:
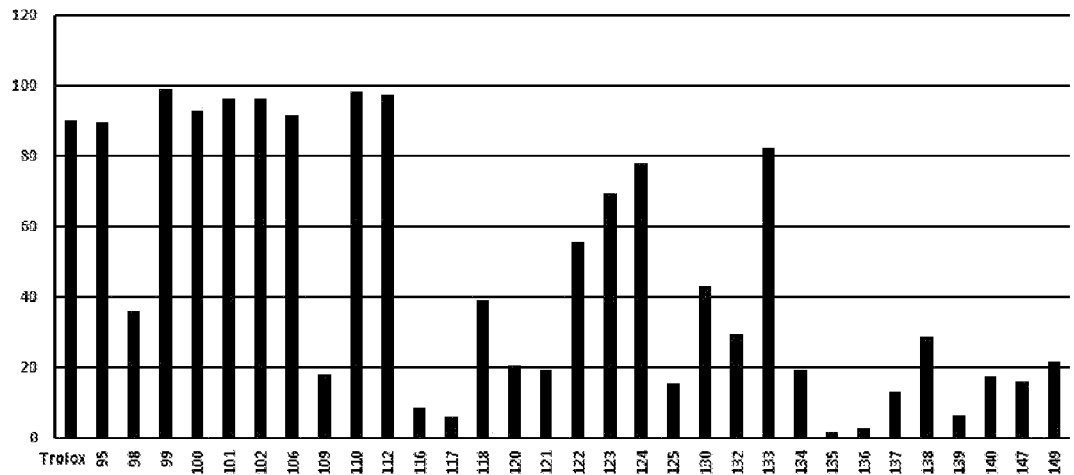

As a result, as shown in FIGS. 1 to 3, Compounds 2, 15, 26, 37, 50, 62, 75, 95, 99, 100, 101, 102, 106, 110, and 112 were screened out as a compound that has as high scavenging effects on ROS generated by vascular endothelial cells as trolox, which was used as a positive control.

Experimental Example 2

Tyrosinase Inhibitory Effect

Mushroom-derived tyrosinase was sued as an enzyme source in the present experiment. Tyrosinase activities were assayed according to a slightly-modified conventionally known method (Life Sci., 1999, 65, 241-246). In detail, 20 μl of a mushroom-derived tyrosinase (1000 units) aqueous solution was added to 96-well microplate (Nunc, Denmark) to prepare 200 μl of the total volume of assay mixture containing 1 mM L-tyrosin solution and 50 mM phosphate buffer solution (pH 6.5). The assay mixture was cultured at a temperature of 25° C. for 30 minutes. After the culturing, an amount of the produced DOPA chrome in the reaction mixture was measured by using a microplate reader (Hewlett Packard) at 492 nm ($OD_{492}$).

Figure 4:
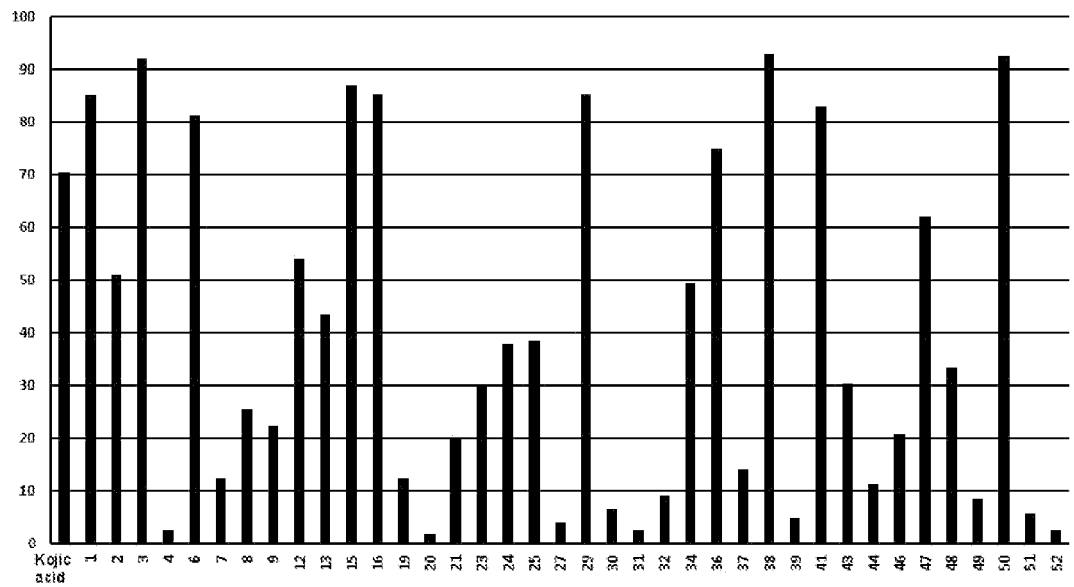
FIGS. 4 to 6 are graphs showing tyrosinase suppression activities of a compound according to the present invention.
Figure 5:
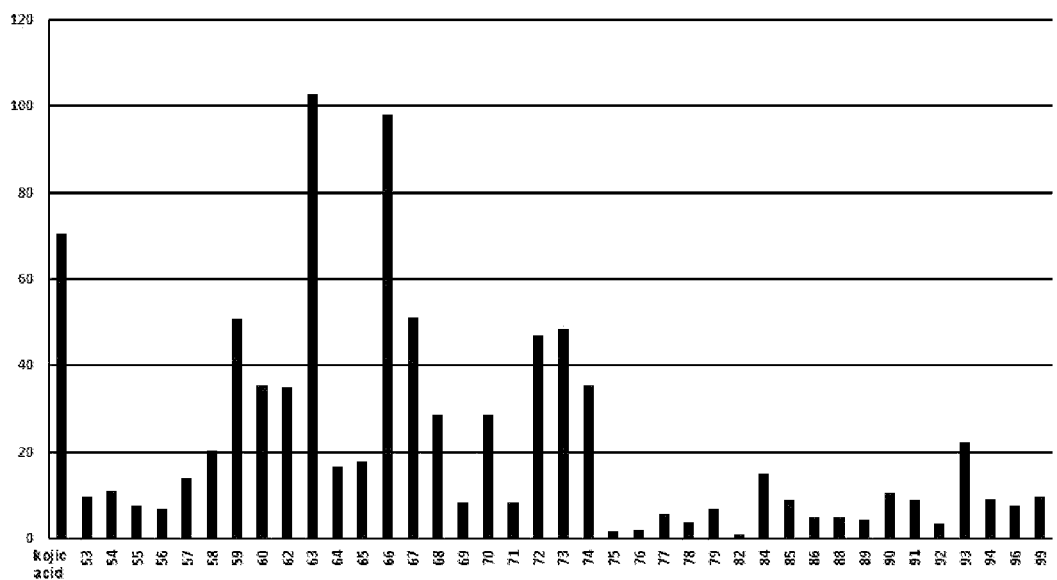
Figure 6:
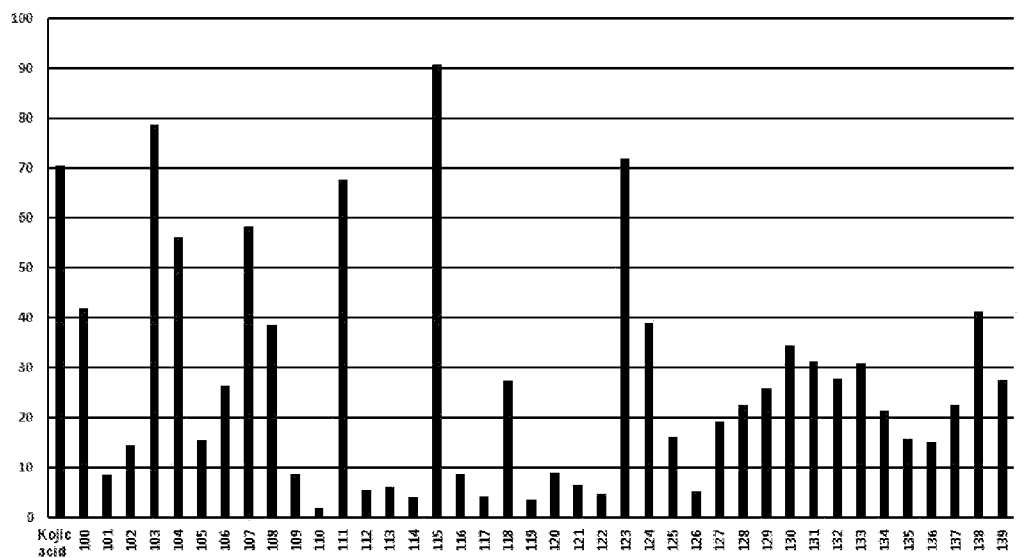

As a result, as shown in FIGS. 4 to 6, Compounds 1, 3, 6, 15, 16, 29, 36, 38, 41, 50, 63, 66, 103, 115, and 123 were screened out as a compound that has better tyrosinase inhibitory activities than a kojic acid, which was used as a positive control.

Experimental Example 3

PPAR Assay

20 μl of a sample and 10 μl of 4× fluormone Pan-PPAR green were spread onto 384 well plates, and 10 μl of 4×PPAR alpha-LBD/Tb-anti-GST antibody or 10 μl of 4×PPAR gamma-LBD/Tb-anti-GST antibody were respectively used in PPAR alpha assay and PPAR gamma assay. In this regard, a sample compound was dissolved in such an amount of DMSO that made a final concentration of the sample to be 100 μM, and the DMSO final concentration was maintained within 1%. The reaction mixture was left at room temperature for 2 to 6 hours, and then, the absorption thereof was measured by using a microplate reader (Hewlett Packard) at an excitation wavelength of 340 nm and at an emission wavelength of 485 nm, and at an exitation wavelength of 340 nm and an emission wavelength of 520 nm to calculate a value of 520 nm/485 nm. In this regard, if a negative control was assumed to have an absorption value of 100, a competitive activation rate was defined as follows: 100 minus an absorption value of each sample. That is, the competitive activation rate indicates a binding ratio of the respective samples with respect to the negative control.

1. PPARα

To evaluate PPARα activities, evaluation values were divided in three scales since the binding activity of fenofibrate, which was used as a positive control, was not high. In detail, a value (3 to 10) that was similar to that of the positive control was indicated as '≈ feno', a value (10 to 25) that was slightly higher than that of the positive control was indicated as '> feno', and a value (25 or more) that was much higher than that of the positive control was indicated as '>> feno', and a material that has a higher value than a negative control during measurement was designated as 'ND'. The presence of ND was due to the fluorescence of sample compounds themselves.

Figure 7:
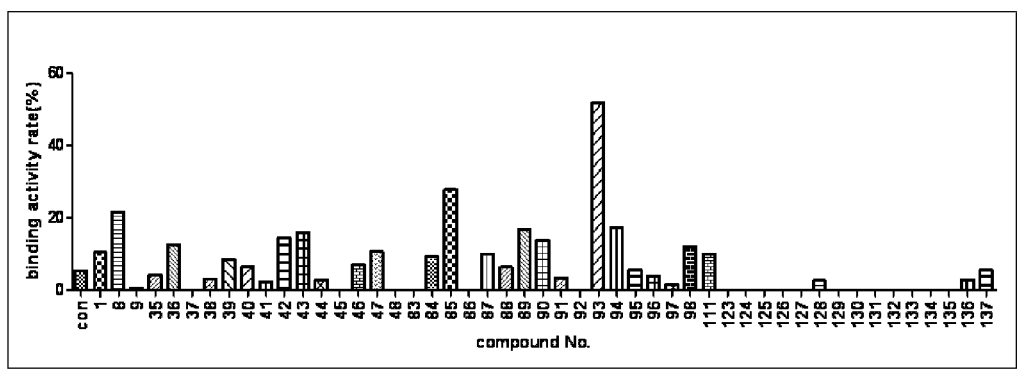
FIG. 7 is a graph showing PPARα enhancement activities of a compound according to the present invention.

As shown in FIG. 7, Compounds 85 and 93 were confirmed as a very excellent PPARα activation agent compared to fenofibrate, which was used as a positive control.

2. PPARγ

To evaluate PPARγ a material that has an activity similar to that of rosiglitazone was indicated as '≈ Rosi', and a material that has a higher activity than that of rosiglitazoneivity was indicated as '> Rosi', and like PPARα, a material that has a higher value than a negative control during measurement was designated as 'ND'.

Figure 8:
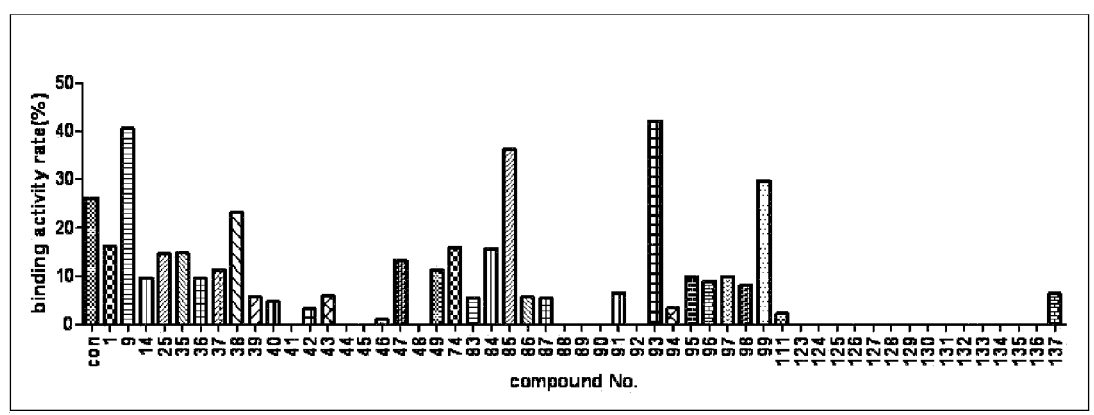
FIG. 8 is a graph showing PPARγ enhancement activities of a compound according to the present invention.

As shown in FIG. 8, Compounds 9, 85, 93, and 99 were confirmed as a better PPARα activation agent than rosiglitazone, which was used as a positive control In particular, Compounds 85 and 93 were identified as an activation agent that simultaneously activates PPARα and PPARγ.

Experimental Example 4

Toxicity Test

A suspension of each of Compound 3, Compound 15, Compound 50, Compound 85, Compound 93, and Compound 115 in a 0.5% methylcellulose solution was orally administered once to a male Balb/c mouse in dosages of 0.5 g/kg, 1 g/kg, and 2 g/kg, and then the survival rate and body weight of the mouse was recorded for 7 days.

After the administration, whether the mouse died, clinical symptoms occurred, and body weight changed were identified and hematologic examination and blood biochemical examination were performed, and autopsy was performed to identify with naked eyes states of abdominal cavity organs and thoracic cavity organs.

As a result, all the animals neither had distinctive clinical symptoms nor died, and even in consideration of body weight change, hematologic examination results, blood biochemical examination results, and autopsy referral, toxicity change was not identified.

As shown in these results, compounds according to the present invention did not have the toxicity change in up to 2 g/kg of rats, and accordingly, it was considered that the compounds were safe in view that a median lethal dose (LD50) thereof for oral administration was 2 g/kg or more.

Hereinafter, preparation examples of a composition including Compound 93 according to the present invention will be described in detail. However, the preparation examples are provided for illustrative purpose only and do not limit the scope of the invention.

Prescription Example 1

Prescription Example of Pharmaceutical Composition

Prescription Example 1-1

Preparation of Powder Formulation 20 mg of Compound 93, 100 mg of lactose, and 10 mg of talc were mixed and then a sealing package was filled therewith to prepare a powder formulation.

Prescription Example 1-2

Preparation of Tablet Formulation 20 mg of Compound 93, 100 mg of corn starch, 100 mg of lactose, and 2 mg of magnesium stearate were mixed, and then, the mixture was tabulated according to a conventional tablet preparation method to prepare a tablet formulation.

Prescription Example 1-3

Preparation of Capsule Formulation 10 mg of Compound 93, 100 mg of corn starch, 100 mg of lactose, and 2 mg of magnesium stearate were mixed according to a conventional capsule preparation method, and then, a gelain capsule was filled with the mixture to prepare a capsule formulation Prescription Example 1-4

Preparation of Injection Formulation 10 mg of Compound 93, an appropriate amount of sterilized distilled water for injection, and an appropriate amount of a pH controller were mixed and then, according to a conventional injection formulation preparation method, an injection preparation was prepared in such a way that one ample (2 ml) has the components in the amounts described above.

Prescription Example 1-5

Preparation of Ointment Formulation 10 mg of Compound 93, 250 mg of PEG-4000, 650 mg of PEG-400, 10 mg of white vaseline, 1.44 mg of methyl p-hydroxybenzoate, 0.18 mg of propyl p-hydroxybenzoate, and the balanced amount of purified water were mixed, and then, the mixture was used to prepare an ointment formulation according to a conventional ointment preparation method.

Prescription Example 2

Prescription Example of Cosmetic Composition

Prescription Example 2-1

Preparation of Nutrition Lotion 3.0 parts by weight of propylene glycol, 0.1 parts by weight of carboxypolymer, a trace of a preservative, and the balanced amount of purified water were mixed by stirring while heating to a temperature of 80 to 85° C. The mixture was loaded into a preparation unit, and then, an emulsifying machine was driven, and 1.0 part by weight of polysolvate 60, 0.5 parts by weight of sorbitan sesquiolate, 10.0 parts by weight of liquid paraffin, 1.0 part by weight of sorbitan stearate, 0.5 parts by weight of lipophilic glyceryl monostearate, 1.5 parts by weight of stearic acid, 1.0 part by weight of glyceryl stearate/PEG-400 stearate, and 0.2 parts by weight of triethanolamine were heated to a temperature of 80 to 85° C., and then, loaded thereinto to perform emulsification. When the emulsifying was completely performed, the mixture was stirred by using an agitator while heat-cooling to a temperature of 50° C., and then, a trace of flavoring agent was added thereto, and after cooling to a temperature of 45° C., a trace of pigment was added thereto, and Compound 93 was added thereto at a temperature of 35° C. and the resultant mixture was cooled to a temperature of 25° C. and aged.

Prescription Example 2-2

Preparation of Nutrition Cream 0.3 parts by weight of carboxypolymer, 5.0 parts by weight of butylene glycol, 3.0 parts by weight of glycerin, and the balanced amount of purified water were mixed by stirring while heating to a temperature of 80 to 85° C., and the mixture was loaded into a preparation unit, and then, an emulsifying machine was driven. Then, 2.0 parts by weight of a stearic acid, 2.0 parts by weight of cetylalcohol, 2.0 parts by weight of glyceryl monostearate, 0.5 parts by weight of polyoxyethylenesorbitanmonostearate, 0.5 parts by weight of sorbitansesquiolate, 1.0 part by weight of wax, 1.0 part by weight of glyceryl monostearate/glyceryl stearate/polyoxyethylenestearate, 4.0 parts by weight of liquid paraffin, 4.0 parts by weight of squalane, and 4.0 parts by weight of caprylic/capric triglyceride were heated to at temperature of 80 to 85° C. and then loaded thereinto, and then, 0.5 parts by weight of triethanolamine was loaded thereinto and emulsifying was performed thereon. When the emulsifying was completely performed, the resultant mixture was stirred by using an agitator while cooling to a temperature of 35° C., and then, Compound 93 was loaded thereinto and cooled to a temperature of 25° C. and aged.

Prescription Example 2-3

Preparation of Washfoam 30.0 parts by weight of TEA-cocoyl glutamate, 10.0 parts by weight of disodium laureth sulfosuccinateglycerin, 10.0 parts by weight of glycerin, 2.0 parts by weight of cocamide DEA, 1.0 part by weight of PEG-120 methylglucose dioliate, 0.5 parts by weight of methyl gluceth-20, 0.5 parts by weight of PEG-150 pentaerythrityl tetra stearate, 0.05 parts by weight of tetrasodium EDTA, and a trace of preservative were sequentially added into a preparation unit, and then, heated to a temperature of 60 to 65° C. and then stirred for 15 minutes. When the stirring was completely performed, some of purified water was added therein and then the resultant mixture was stirred for 30 minutes, and then, some of purified water was slowly added thereinto and then the resultant mixture was stirred for 30 minutes, and then cooled to a temperature of 35° C., and Compound 93 and a flavoring agent were added thereinto, and then, the resultant mixture was cooled to a temperature of 25° C. and aged.

Prescription Example 3

Supplementary Health Food

Prescription Example 3-1

Preparation of Health Foods 1 mg of Compound 93, an appropriate amount of vitamin mixture (including 70 μg of vitamin A acetate, 1.0 mg of vitamin E, 0.13 mg of vitamin B 1, 0.15 mg of vitamin B 2, 0.5 mg of vitamin B 6, 0.2 μg of vitamin B 12, 10 mg of vitamin C, 10 μg of biotin, 1.7 mg of nicotinamide, 50 μg of folate, and 0.5 mg of calcium pantothenate), and an appropriate amount of mineral mixture (1.75 mg of ferrous sulphate, 0.82 mg of zinc oxide, 25.3 mg of magnesium carbonate, 15 mg of potassium phosphate monobasic, 55 mg of calcium phosphate dibasic, 90 mg of potassium citrate, 100 mg of calcium carbonate, and 24.8 mg of magnesium chloride) were mixed, and then, prepared in a granule formulation, and then, a health food was prepared according to a conventional method.

Prescription Example 3-2

Preparation of Health Beverage 1 mg of Compound 93, 1000 mg of a citric acid, 100 g of oligosaccharide, 2 g of plum concentrate, 1 g of taurine, and such an amount of purified water that a total volume of the mixture reached 900 ml were prepared, and these components were mixed according to a conventional health beverage preparation method, and then, the mixture was stirred for about 1 hour while heating at a temperature of 85° C., and then the prepared solution was filtered, and a sterilized 2 L container was filled therewith and then, sealed and sterilized, and then, refrigerated.

The invention claimed is:
1. A skin-whitening method, comprising:
   administering to a subject in need thereof a compound selected from the group consisting of (Z)-5-(4-hydroxybenzylidene)thiazolidine-2,4-dione (Compound 1), (Z)-5-(2,4-dihydroxybenzylidene)thiazolidine-2,4-dione (Compound 3), and (Z)-5-(3-hydroxy-4-methoxybenzylidene)thiazolidine-2,4-dione (Compound 6).

* * * * *